United States Patent [19]

Wilkerson et al.

[11] Patent Number: 5,508,400
[45] Date of Patent: Apr. 16, 1996

[54] PREPARATION OF CYCLIC UREA COMPOUNDS

[75] Inventors: Wendell W. Wilkerson, New Castle, Del.; James D. Rodgers, Landenberg, Pa.

[73] Assignee: The Du Pont Merck Pharmaceutical Company, Wilmington, Del.

[21] Appl. No.: 230,562

[22] Filed: Apr. 20, 1994

[51] Int. Cl.⁶ .................. C07D 243/04; A61K 31/55
[52] U.S. Cl. ............................. 340/460; 540/492
[58] Field of Search .................... 540/460, 492

[56] References Cited

U.S. PATENT DOCUMENTS 4,749,681  6/1988  Evers ........................... 512/8

FOREIGN PATENT DOCUMENTS

| 8910752 | 11/1989 | WIPO | 544/335 |
| 9209297 | 6/1992 | WIPO | 540/531 |
| 9221647 | 12/1992 | WIPO | 549/14 |
| WO9307128 | 4/1993 | WIPO | 540/460 |

OTHER PUBLICATIONS

Moore, et al., *Biochem. Biophys. Res. Comm.* (1989) 159:420–425.
Orszanska and Rulko, *Polish J. Chem.* (1982) 56:1287–1296.
Chenera, et al., *Bioorganic & Med. Chem. Lett.* (1993) 3:2717–2722.
Kempf, et al. *J. Med. Chem.* (1990) 33(10):2687–2689.
Kempf, et al., *J. Org. Chem.* (1992) 57:5692–5700.
Newlander, et al., *J. Med. Chem.* (1993) 36:2321–2331.

*Primary Examiner*—Robert T. Bond

[57] ABSTRACT

This invention relates to the preparation of cyclic urea compounds. More specifically, this invention is directed to methods for selectively alkylating diamines, methods for selectively converting a mixture of alkylated and non-alkylated diamines to cyclic urea compounds, methods to purify cyclic urea compounds having a single N-substitution, methods to convert a cyclic urea compound having a single N-substitution to a cyclic urea compound having either symmetrical or non-symmetrical N,N'-disubstitution, and methods to remove protecting groups from cyclic urea compounds.

83 Claims, No Drawings

PREPARATION OF CYCLIC UREA COMPOUNDS

FIELD OF THE INVENTION

This invention relates to the preparation of cyclic urea compounds. More specifically, this invention is directed to methods for selectively alkylating diamines, methods for selectively converting a mixture of alkylated and non-alkylated diamines to cyclic urea compounds, methods to purify cyclic urea compounds having a single N-substitution, methods to convert a cyclic urea compound having a single N-substitution to a cyclic urea compound having either symmetrical or non-symmetrical N,N'-disubstitution, and methods to remove protecting groups from cyclic urea compounds.

BACKGROUND OF THE INVENTION

PCT Patent Application Publication Number WO 93/07128 ("Jadhav et al.") discloses that N,N'-disubstituted cyclic urea compounds are selective inhibitors of human immunodeficiency virus (HIV) protease, and as such, may be useful in the treatment of acquired immunodeficiency syndrome (AIDS). Jadhav, et al. teach that N,N'-symmetrically disubstituted cyclic urea compounds can be synthesized by reacting an unsubstituted cyclic urea compound with excess strong base and excess alkylating agent. Jadhav, et al. also teach that N,N'-non-symmetrically disubstituted cyclic urea compounds can be synthesized by reacting an unsubstituted cyclic urea compound with less than two equivalents of alkylating agent followed by chromatographic separation of the resulting mixture comprising unsubstituted cyclic urea compound, monosubstituted cyclic urea compound, and symmetrically disubstituted cyclic urea compound, followed by treating the isolated monosubstituted cyclic urea compound with strong base and an alkylating agent.

The present invention provides an improved method for the preparation of N,N'-disubstituted cyclic urea compounds, and is particularly advantageous for the preparation of N,N'-non-symmetrically disubstituted cyclic urea compounds, and precursors and derivatives thereof.

SUMMARY OF THE INVENTION

One aspect of the invention is a method for preparing a cyclic urea compound of Formula (Id) comprising the steps:

(a) converting a compound of Formula (IIa) to a compound of Formula (IIb) by any of direct alkylation, reductive amination, or successive acylation and reduction, (b) converting the compound of Formula (IIb) from step (a) to a product comprising a cyclic urea compound of Formula (Ib), (c) purifying the product of step (b) by
  (i) washing the product of step (b) with an aqueous acid solution, resulting in a washed product, and
  (ii) eluting the washed product of step (c)(i) through a bed of silica gel to produce a substantially pure compound of Formula (Ib), (d) converting the substantially pure compound of Formula (Ib) from step (c)(ii) to a cyclic urea compound of Formula (Ic), and (e) converting the compound of Formula (Ic) from step (d) to a cyclic urea compound of Formula (Id), wherein, the compound of Formula (IIa) has the structure shown in Formula (II) with the proviso that $R^{22}$ and $R^{23}$ are hydrogen, the compound of Formula (IIb) has the structure shown in Formula (II) with the proviso that only one of $R^{22}$ or $R^{23}$ is hydrogen, the compound of Formula (Ib) has the structure shown in Formula (I) with the proviso that only one of $R^{22}$ or $R^{23}$ is hydrogen, the compound of Formula (Ic) has the structure shown in Formula (I) with the proviso that neither $R^{22}$ nor $R^{23}$ is hydrogen, the compound of Formula (Id) has the structure shown in Formula (I) with the provisos that neither $R^{22}$ nor $R^{23}$ is hydrogen and none of the hydroxyl, sulfhydryl or amine groups which may be present in the compound of Formula (Id) are protected by a hydroxyl, sulfhydryl or amine protecting group, compound (I) has a Formula:

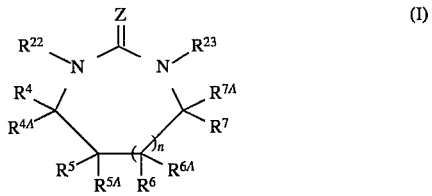

including a pharmaceutically acceptable salt or prodrug form thereof, and compound (II) has a Formula:

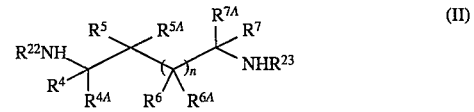

wherein, for each compound of Formula (I) and Formula (II):

each of $R^4$ and $R^7$ is independently:
  hydrogen, —O($R^{13}$), —S($R^{13}$), —C(=O)O($R^{13}$),
  $C_1$–$C_8$ alkyl substituted with 0–3 $R^{11}$,
  $C_2$–$C_8$ alkenyl substituted with 0–3 $R^{11}$,
  $C_2$–$C_8$ alkynyl substituted with 0–3 $R^{11}$,
  a $C_3$–$C_{14}$ carbocyclic ring system substituted with 0–3 $R^{11}$ or 0–3 $R^{12}$, or
  a 5- to 10-membered heterocyclic ring system containing 1 to 4 heteroatoms independently selected from oxygen, nitrogen or sulfur, the heterocyclic ring system being substituted with 0–2 $R^{12}$;

each of $R^{4A}$ and $R^{7A}$ is independently:
  hydrogen, —O($R^{13}$), —S($R^{13}$), —C(=O)O($R^{13}$),
  $C_1$–$C_4$ alkyl unsubstituted or substituted with halogen or $C_1$–$C_2$ alkoxy, or
  phenylmethyl unsubstituted or substituted with halogen or $C_1$–$C_2$ alkoxy;

$R^4$ and $R^{4A}$ can alternatively join to form a 5- to 7-membered carbocyclic ring substituted with 0–2 $R^{12}$;

$R^7$ and $R^{7A}$ can alternatively join to form a 5- to 7-membered carbocyclic ring substituted with 0–2 $R^{12}$;

each of $R^5$ and $R^{5A}$ is independently:
  hydrogen, halogen, —N($R^{20}$)$_2$, —S($R^{20}$), —O($R^{20}$) or $C_1$–$C_6$ alkyl substituted with 0–3 $R^{11}$;

$R^5$ and $R^{5A}$ can alternatively join together to form a =O, =S or a ketal ring;

each of $R^6$ and $R^{6A}$ is independently:
  hydrogen, halogen, —N ($R^{20}$)$_2$, —S ($R^{20}$), —O($R^{21}$) or $C_1$–$C_6$ alkyl substituted with 0–3 $R^{11}$;

$R^6$ and $R^{6A}$ can alternatively join together to form a =O, =S or a ketal ring;

$R^5$ and $R^6$ can alternatively join together to form an epoxide or aziridine ring; —OCH$_2$SCH$_2$O—, —OS(=O)O—, —OC(=O)O—, —OCH$_2$O—, —OC(=S)O—, —OC(=O)C(=O)O—, —OC(CH$_3$)$_2$O—, —OC((CH$_2$)$_3$NH$_2$)(CH$_3$)O—, —OC(OCH$_3$)(CH$_2$CH$_2$CH$_3$)O—, —OS(=O)$_2$O—, —NHC(=O)NH—, —OC(=O)NH—, —NHC(=O)O—, —NHCH$_2$O—, —OCH$_2$NH—, —NHC(=S)O—, —OC(=S)NH—, —OS(=O)NH—, —NHS(=O)O—, —NHC(=O)C(=O)O—, —OC(=O)C(=O)NH—, —NHC(=O)C(=O)NH—, —NHC(CH$_3$)$_2$O—, —OC(CH$_3$)$_2$NH— or any group that, when administered to a mammalian subject as part of a compound of Formula (I), cleaves to form a compound having two free hydroxyl groups, or two free amino groups, or one free hydroxyl group and one free amino group;

each $R^{11}$ is independently:

hydrogen, keto, halogen, cyano, phenylmethyl, phenethyl, methylenedioxy, ethylenedioxy, hydroxamic acid, hydrazide, boronic acid, azido, sulfonamide, formyl, phenoxy, phenylmethoxy, nitro, —CH$_2$N(R$^{13}$)(R$^{14}$), —N(R$^{13}$)(R$^{14}$), —OCH$_2$C(=O)OH, —C(=O)O(R$^{13}$), —OC(=O)(R$^{13}$), —O(R$^{13}$), C$_2$–C$_6$ alkoxyalkyl, —S(=O)$_m$(R$^{13}$), —NHC(=NH)NH(R$^{13}$), —C(=NH)NH(R$_{13}$), —C(=O)N(R$^{13}$)(R$^{14}$), —N(R$^{14}$)C(=O)(R$^{13}$), =N—O(R$^{14}$), —N(R$^{14}$)C(=O)O(R$^{14}$), —OC(=O)N(R$^{13}$)(R$^{14}$), —N(R$^{13}$)C(=O)N(R$^{13}$)(R$^{14}$), —C(R$^{14}$)=N—O(R$^{14}$), —N(R$^{14}$)S(=O)$_2$N(R$^{13}$)(R$^{14}$), —N(R$^{14}$)S(=O)$_2$(R$^{13}$), —S(=O)$_2$N(R$^{13}$)(R$^{14}$), C$_1$–C$_4$ alkyl, C$_2$–C$_4$ alkenyl, C$_3$–C$_{10}$ cycloalkyl, C$_3$–C$_6$ cycloalkylmethylene, C$_7$–C$_{10}$ arylalkyl, C$_3$–C$_6$ cycloalkoxy, C$_1$–C$_4$ alkyl substituted with —N(R$^{13}$)(R$^{14}$), C$_1$–C$_4$ hydroxyalkyl, C$_1$–C$_4$ haloalkyl, C$_1$–C$_4$ haloalkoxy, C$_1$–C$_4$ alkoxycarbonyl, C$_1$–C$_4$ alkylcarbonyloxy, C$_1$–C$_4$ alkylcarbonyl, C$_1$–C$_4$ alkylcarbonylamino, 2-(1-morpholino)ethoxy, -(C$_1$–C$_3$ alkyl) aryl substituted with 0–2 R$^{12}$, a C$_5$–C$_{14}$ carbocyclic residue substituted with 0–3 R$^{12}$, or a 5- to 10-membered heterocyclic ring system containing 1 to 4 heteroatoms independently selected from oxygen, nitrogen or sulfur, the heterocyclic ring system being substituted with 0–3 R$^{12}$; and 1–3 amino acids linked together via amide bonds, and linked to R$^4$, R$^7$, R$^{20}$, or R$^{21}$ via the amine or carboxylate terminus;

m is: 0, 1 or 2;

each $R^{11A}$ is independently:

H, keto, halogen, cyano, —CH$_2$NH$_2$, —NH$_2$, —C(=O)OH, —OC(=O)(C$_1$–C$_3$ alkyl), —OH, C$_2$–C$_6$ alkoxyalkyl, —C(=O)NH$_2$, —OC(=O)NH$_2$, —NHC(=O)NH$_2$, —S(=O)$_2$, NH$_2$, C$_1$–C$_4$ alkyl, C$_2$–C$_4$ alkenyl, C$_3$–C$_{10}$ cycloalkyl, C$_3$–C$_6$ cycloalkylmethylene, benzyl, phenethyl, phenoxy, benzyloxy, nitro, C$_7$–C$_{10}$ arylalkyl, hydroxamic acid, hydrazide, boronic acid, C$_3$–C$_6$ cycloalkoxy, C$_1$–C$_4$ alkyl substituted with —NH$_2$, C$_1$–C$_4$ hydroxyalkyl, methylenedioxy, ethylenedioxy, C$_1$–C$_4$ haloalkyl, C$_1$–C$_4$ haloalkoxy, C$_1$–C$_4$ alkoxycarbonyl, C$_1$–C$_4$ alkylcarbonyloxy, C$_1$–C$_4$ alkylcarbonyl, C$_1$–C$_4$ alkylcarbonylamino, —OCH$_2$C(=O)OH, 2-(1-morpholino) ethoxy, azido, aryl (C$_1$–C$_3$ alkyl), a C$_5$–C$_{14}$ carbocyclic residue, or a 5- to 10-membered heterocyclic ring system containing 1 to 4 heteroatoms independently selected from oxygen, nitrogen or sulfur;

each R$^{12}$, when a substituent on carbon, is independently:

phenyl, phenylmethyl, phenethyl, phenoxy, phenylmethoxy, halogen, hydroxy, nitro, cyano, C$_1$–C$_4$ alkyl, C$_3$–C$_6$ cycloalkyl, C$_3$–C$_6$ cycloalkylmethylene, C$_7$–C$_{10}$ arylalkyl, C$_1$–C$_4$ alkoxy, —C(=O)OH, hydroxamic acid, hydrazide, boronic acid, sulfonamide, formyl, C$_3$–C$_6$ cycloalkoxy, —O(R$^{13}$), C$_1$–C$_4$ alkyl substituted with —N(R$^{13}$)(R$^{14}$), —N(R$^{13}$)(R$^{14}$), C$_2$–C$_6$ alkoxyalkyl, C$_1$–C$_4$ hydroxyalkyl, methylenedioxy, ethylenedioxy, C$_1$–C$_4$ haloalkyl, C$_1$–C$_4$ haloalkoxy, C$_1$–C$_4$ alkoxycarbonyl, C$_1$–C$_4$ alkylcarbonyloxy, C$_1$–C$_4$ alkylcarbonyl, C$_1$–C$_4$ alkylcarbonylamino, —S(=O)$_m$(R$^{13}$), —S(=O)$_2$N(R$^{13}$)(R$^{14}$), —NHS(=O)$_2$(R$^{14}$), —OCH$_2$C(=O)OH, 2-(1-morpholino) ethoxy, —C(R$^{14}$)=N—O(R$^{14}$), a 5-to 10-membered heterocyclic ring containing from 1 to 4 heteroatoms independently selected from oxygen, nitrogen or sulfur, the heterocyclic ring system being substituted with 0–3 R$^{15}$, a 3- or 4-carbon aliphatic chain attached to an adjacent carbon on the ring to which it is appended to form a fused 5- or 6-membered ring, the 5- or 6-membered ring being optionally substituted on any of the aliphatic carbons with halogen, C$_1$–C$_4$ alkyl, C$_1$–C$_4$ alkoxy, hydroxy, —N(R$^{13}$)(R$^{14}$), or when R$^{12}$ is a substituent on a saturated carbon atom, R$^{12}$ may alternatively be =O or =S;

each R$^{12}$, when a substituent on nitrogen, is independently:

phenyl, phenylmethyl, phenethyl, hydroxy, C$_1$–C$_4$ hydroxyalkyl, C$_1$–C$_4$ alkoxy, C$_1$–C$_4$ alkyl, C$_3$–C$_6$ cycloalkyl, C$_3$–C$_6$ cycloalkylmethylene, —CH$_2$N(R$^{13}$)(R$^{14}$), —N(R$^{13}$)(R$^{14}$), C$_2$–C$_6$ alkoxyalkyl, C$_1$–C$_4$ haloalkyl, C$_1$–C$_4$ alkoxycarbonyl, —C(=O)OH, C$_1$–C$_4$ alkylcarbonyloxy, C$_1$–C$_4$ alkylcarbonyl or —C(R$^{14}$)=N—O(R$^{14}$);

each $R^{13}$ is independently:

hydrogen, phenyl substituted with 0–3 R$^{11A}$, phenylmethyl substituted with 0–3 R$^{11A}$, C$_1$–C$_6$ alkyl substituted with 0–3 R$^{11A}$, C$_2$–C$_4$ alkenyl substituted with 0–3 R$^{11A}$, C$_1$–C$_6$ alkylcarbonyl substituted with 0–3 R$^{11A}$, C$_1$–C$_6$ alkoxycarbonyl substituted with 0–3 R$^{11A}$, C$_1$–C$_6$ alkylaminocarbonyl substituted with 0–3 R$^{11A}$, C$_3$–C$_6$ alkoxyalkyl substituted with 0–3 R$^{11A}$, an amine protecting group when R$^{13}$ is bonded to N, or a hydroxy protecting group when R$^{13}$ is bonded to O;

each $R^{14}$ is independently:

hydrogen, hydroxy, trifluoromethyl, C$_1$–C$_6$ alkoxy, C$_2$–C$_6$ alkenyl, phenylmethyl, amino, C$_1$–C$_6$ alkyl substituted with 0–3 groups selected from hydroxy, C$_1$–C$_4$ alkoxy, halogen or amino, an amine protecting group when R$^{14}$ is bonded to N, or a hydroxy protecting group when R$^{14}$ is bonded to O;

R$^{13}$ and R$^{14}$ can alternatively join to form:

—(CH$_2$)$_4$—, —(CH$_2$)$_5$—, —CH$_2$CH$_2$N(R$^{15}$)CH$_2$CH$_2$— or —CH$_2$CH$_2$OCH$_2$CH$_2$—;

R$^{15}$ is: hydrogen or methyl;

each of R$^{20}$ and R$^{21}$ is independently:

hydrogen,

C$_1$–C$_6$ alkyl substituted with 0–3 R$^{11}$, $C_3$–$C_6$ alkoxyalkyl substituted with 0–3 $R^{11}$, $C_1$–$C_6$ alkylcarbonyl substituted with 0–3 $R^{11}$, $C_1$–$C_6$ alkoxycarbonyl substituted with 0–3 $R^{11}$, $C_1$–$C_6$ alkylaminocarbonyl substituted with 0–3 $R^{11}$, benzoyl substituted with 0–3 $R^{12}$, phenoxycarbonyl substituted with 0–3 $R^{12}$, phenylaminocarbonyl substituted with 0–3 $R^{12}$, or any group that, when administered to a mammalian subject as part of a compound of Formula (I), cleaves to form a free hydroxyl, free amino or free sulfhydryl;

each of $R^{22}$ and $R^{23}$ is independently:

hydrogen, $C_1$–$C_8$ alkyl substituted with 0–3 $R^{31}$, $C_2$–$C_8$ alkenyl substituted with 0–3 $R^{31}$, $C_2$–$C_8$ alkynyl substituted with 0–3 $R^{31}$, a $C_3$–$C_{14}$ carbocyclic ring system substituted with 0–5 $R^{31}$ or 0–5 $R^{32}$, or a 5- to 10-membered heterocyclic ring system containing 1 to 4 heteroatoms independently selected from oxygen, nitrogen or sulfur, the heterocyclic ring system being substituted with 0–2 $R^{32}$;

alternatively, $R^{22}$ can join with $R^4$ or $R^{4A}$ to form a 5- or 6-membered fused heterocyclic ring or carbocyclic ring substituted with 0–2 $R^{12}$, the heterocyclic ring containing 1–3 heteroatoms independently selected from nitrogen, sulfur or oxygen;

alternatively, $R^{23}$ can join with $R^7$ or $R^{7A}$ to form a 5- or 6-membered fused heterocyclic ring or carbocyclic ring substituted with 0–2 $R^{12}$, the heterocyclic ring containing 1–3 heteroatoms independently selected from nitrogen, sulfur or oxygen;

alternatively, $R^{22}$ or $R^{23}$ can join with $R^5$ or $R^6$ to form a 0- to 7- membered bridge to form a carbocyclic or heterocyclic ring, said bridge being substituted with 0–2 $R^{12}$ and the bridge containing 0–3 heteroatoms independently selected from nitrogen, sulfur or oxygen (i.e., a 0-membered bridge is formed when a direct bond is formed between $R^{22}$ and $R^5$ or $R^6$ or between $R^{23}$ and $R^5$ or $R^6$);

alternatively, the atoms to which $R^{22}$ and $R^{4A}$ are appended may be joined together with a double bond;

alternatively, the atoms to which $R^{23}$ and $R^{7A}$ are appended may be joined together with a double bond;

Z is: O or S;

each $R^{31}$ is independently:

keto, halogen, cyano, —$CH_2N(R^{13})(R^{14})$, —$N(R^{13})(R^{14})$, —$C(=O)O(R^{13})$, —$C(=O)(R^{11})$, —$OC(=O)(R^{13})$, —$O(R^{13})$, $C_2$–$C_6$ alkoxyalkyl, —$S(=O)_m(R^{13})$, —$NHC(=NH)NH(R^{13})$, —$C(=NH)NH$ ($R^{13}$), —$C(=O)N(R^{13})(R^{14})$, —$N(R^{14})C(=O)(R^{13})$, =$N$—$O(R^{14})$, —$N(R^{14})C(=O)O(R^{14})$, —$OC(=O)N(R^{13})(R^{14})$, —$N(R^{13})C(=O)N(R^{13})(R^{14})$, —$N(R^{14})S(=O)_2N(R^{13})(R^{14})$, —$R^{14}S(=O)_2(R^{13})$, —$S(=O)_2N(R^{13})(R^{14})$, ($C_1$–$C_4$ alkyl, $C_2$–$C_4$ alkenyl, $C_3$–$C_{10}$ cycloalkyl, $C_3$–$C_6$ cycloalkylmethylene, phenylmethyl, phenethyl, phenoxy, phenylmethoxy, nitro, $C_7$–$C_{10}$ arylalkyl, hydroxamic acid, hydrazide, oxime, boronic acid, sulfonamide, formyl, $C_3$–$C_6$ cycloalkoxy, $C_1$–$C_4$ alkyl substituted with —$N(R^{13})(R^{14})$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$OCH_2C(=O)O(R^{13})$, 2-(1-morpholino) ethoxy, azido, —$C(R^{14})=N$—$O(R^{14})$, a $C_5$–$C_{14}$ carbocyclic residue substituted with 0–5 $R^{32}$, a 5- to 10-membered heterocyclic ring system containing 1 to 4 heteroatoms independently selected from oxygen, nitrogen or sulfur, the heterocyclic ring system being substituted with 0–2 $R^{32}$, or 1–3 amino acids, linked together via amide bonds, and linked to $R^{22}$ or $R^{23}$ via the amine or carboxylate terminus;

each $R^{32}$, when a substituent on carbon, is independently:

phenethyl, phenoxy, $C_3$–$C_{10}$ cycloalkyl, $C_3$–$C_6$ cycloalkylmethylene, $C_7$–$C_{10}$ arylalkyl, hydrazide, oxime, $C_2$–$C_6$ alkoxyalkyl, methylenedioxy, ethylenedioxy, $C_1$–$C_4$ alkylcarbonyloxy, —$NHS(=O)_2(R^{14})$, phenylmethoxy, halogen, 2-(1-morpholino)ethoxy, —$C(=O)O(R^{13})$, hydroxamic acid, —$C(=O)N(R^{13})N(R^{13})(R^{14})$, cyano, boronic acid, sulfonamide, formyl, $C_3$–$C_6$ cycloalkoxy, $C_1$–$C_4$ haloalkyl, $C_1$–$C_4$ haloalkoxy, $C_2$–$C_4$ haloalkenyl, $C_2$–$C_4$ haloalkynyl, —$N(R^{13})(R^{14})$, —$C(R^{14})=N$—$O(R^{14})$, —$NO_2$, —$O(R^{13})$, —$N(R^{40})(R^{41})$, —$S(=O)_m(R^{13})$, —$S(=O)_mN(R^{13})(R^{14})$, —$C(=O)N(R^{13})(R^{14})$, —$OC(=O)N(R^{13})(R^{14})$, —$C(=O)(R^{11})$, —$OC(=O)(R^{11})$, —$OC(=O)O(R^{13})$, phenyl, —$C(=O)N(R^{13})$—($C_1$–$C_4$ alkyl)-$N(R^{13})(R^{14})$, —$C(=O)N(R^{40})(R^{41})$, —$C(=O)N(R^{13})C(R^{11})_2N(R^{13})(R^{14})$, —$C(=O)N(R^{13})C(R^{11})_2N(R^{13})NH$ ($R^{14}$), —$C(=O)N(R^{13})C(R^{11})_2N(R^{13})C(=O)O(R^{13})$, —$C(=O)N(R^{13})$—($C_1$–$C_4$ alkyl)-$N(R^{13})C(=O)O(R^{13})$, —$C(=O)N(R^{13})$—($C_1$–$C_4$ alkyl)-$R^{11}$, —$C(=O)C(R^{11})_2N(R^{13})(R^{14})$, —$C(=O)C(R^{11})_2N(R^{13})NH(R^{14})$, —$C(=O)C(R^{11})_2N(R^{13})C(=O)O(R^{13})$, —$C(=O)$—($C_1$–$C_4$ alkyl)—$N(R^{13})(R^{14})$, —$C(=O)$—($C_1$–$C_4$ alkyl)—$N(R^{13})C(=O)O(R^{13})$, $C_1$–$C_4$ alkoxy substituted with 0–4 groups selected from: $R^{11}$, $C_3$–$C_6$ cycloalkyl, —$C(=O)O(R^{13})$, —$C(=O)N(R^{13})(R^{14})$, —$N(R^{13})(R^{14})$ or hydroxyl, $C_1$–$C_4$ alkyl substituted with 0–4 groups selected from: $R^{11}$=$N(R^{14})$, =$NN(R^{13})C(=O)N(R^{13})(R^{14})$ or —$N(R^{13})(R^{14})$, $C_2$–$C_4$ alkenyl substituted with 0–4 $R^{11}$, $C_2$–$C_4$ alkynyl substituted with 0–4 $R^{11}$, a 5- or 6-membered heterocyclic ring containing from 1 to 4 heteroatoms independently selected from oxygen, nitrogen or sulfur, a 3- or 4-carbon aliphatic chain attached to an adjacent carbon on the ring to which it is appended, to form a fused 5- or 6-membered ring, the 5- or 6-membered ring being optionally substituted on the aliphatic carbons with halogen, $C_1$–$C_4$ alkyl, $C_1$–$C_4$ alkoxy, hydroxyl —$N(R^{13})(R^{14})$, or when $R^{32}$ is attached to a saturated carbon atom, $R^{32}$ may be =O or =S;

each $R^{32}$, when a substituent on nitrogen, is independently:

phenyl, phenylmethyl, phenethyl, hydroxyl, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethylene, —$CH_2N(R^{13})(R^{14})$, —$N(R^{13})(R^{14})$, $C_2$–$C_6$ alkoxyalkyl, $C_1$–$C_4$ haloalkyl, $C_1$–$C_4$ alkoxycarbonyl, —$C(=O)OH$, $C_1$–$C_4$ alkylcarbonyloxy, $C_1$–$C_4$ alkylcarbonyl or —$C(R^{14})=N$—$O(R^{14})$;

$R^{40}$ is: hydrogen or $C_1$–$C_3$ alkyl;

$R^{41}$ is: —$C(=O)N(R^{13})(R^{14})$, —$C(=O)N(R^{13})NH(R^{14})$, —$C(=O)C(R^{11})_2N(R^{13})(R^{14})$, —$C(=O)C(R^{11})_2N(R^{13})NH(R^{14})$, —$C(=O)C(R^{11})_2N(R^{13})C(=O)O(R^{13})$, —$C(=O)$ H, —$C(=O)(R^{11})$, —$C(=O)$—($C_1$–$C_4$ alkyl)—$N(R^{13})(R^{14})$, —$C(=O)$—($C_1$–$C_4$ alkyl)

—N($R^{13}$)C(=O)O($R^{13}$) or 1–3 amino acids linked together via amide bonds and linked to the N atom via the carboxylate terminus; and n is: 0, 1 or 2;

provided that:

$R^4$, $R^{4A}$, $R^7$ and $R^{7A}$ are not all hydrogen;

when $R^4$ and $R^{4A}$ are both hydrogen, $R^{22}$ is not hydrogen, and when $R^7$ and $R^{7A}$ are both hydrogen, $R^{23}$ is not hydrogen.

Another aspect of the invention is a method for preparing a cyclic urea compound of Formula (Ic) comprising the steps:

(a) converting a compound of Formula (IIa) to a compound of Formula (IIb) by any of direct alkylation, reductive amination, or successive acylation and reduction, (b) converting the compound of Formula (IIb) from step (a) to a product comprising a cyclic urea compound of Formula (Ib), (c) purifying the product of step (b) by
  (i) washing the product of step (b) with an aqueous acid solution, resulting in a washed product, and
  (ii) eluting the washed product of step (c)(i) through a bed of silica gel to produce a substantially pure compound of Formula (Ib), and (d) converting the substantially pure compound of Formula (Ib) from step (c)(ii) to a cyclic urea compound of Formula (Ic).

Another aspect of the invention is a method for preparing and purifying a cyclic urea compound of Formula (Ib) comprising the steps:

(a) converting a compound of Formula (IIa) to a compound of Formula (IIb) by any of direct alkylation, reductive amination, or successive acylation and reduction, (b) converting the compound of Formula (IIb) from step (a) to a product comprising a cyclic urea compound of Formula (Ib), (c) purifying the product of step (b) by
  (i) washing the product of step (b) with an aqueous acid solution, resulting in a washed product, and
  (ii) eluting the washed product of step (c)(i) through a bed of silica gel to produce a substantially pure compound of Formula (Ib).

Another aspect of the invention is a method for preparing and purifying a cyclic urea compound of Formula (Ib) comprising the steps:

(a) converting a compound of Formula (IIb) to a cyclic urea compound of Formula (Ib), (b) purifying the product of step (a) by
  (i) washing the product of step (a) with an aqueous acid solution, resulting in a washed product, and
  (ii) eluting the product of step (b)(i) through a bed of silica gel to produce a substantially pure compound of Formula (Ib).

Another aspect of the invention is a method for converting a compound of Formula (IIa) to a compound of Formula (IIb) by any of direct alkylation, reductive amination, or successive acylation and reduction.

In all of the various aspects of the present invention, the compounds of Formulas (I), (Ib), (Ic), (Id), (II), (IIa) and (IIb) are as defined previously in this Summary of the Invention.

The compounds of Formula (I) provided by the methods of this invention are useful as standards and reagents in determining the ability of a potential pharmaceutical to inhibit viral replication of HIV protease. These would be provided in commercial kits comprising a compound of Formula (I) as prepared according to the methods of this invention.

DETAILED DESCRIPTION OF THE PREFERRED EMBODIMENTS

DEFINITIONS

As used herein, the following terms and expressions have the indicated meanings.

"Alkenyl" is intended to include hydrocarbon chains of either a straight or branched configuration having one or more carbon-carbon double bonds which may occur at any point along the chain that results in a stable structure.

"Alkoxy" is intended to include an alkyl group of an indicated number of carbon atoms attached through an oxygen atom to the residue of the compound at the designated location.

"Alkoxyalkyl" is intended to include an alkyl group to which is bonded an alkoxy group, where the alkyl group is also bonded to the residue of the compound at the designated location.

"Alkoxycarbonyl" is intended to include an alkoxy group of an indicated number of carbon atoms attached through its oxygen atom to a carbonyl group, where the carbonyl group is attached to the residue of the compound at the designated location.

"Alkyl" is intended to include both branched and straight-chain saturated aliphatic hydrocarbon groups having the specified number of carbon atoms.

"Alkylcarbonyl" is intended to include an alkyl group of an indicated number of carbon atoms attached through a carbonyl group to the residue of the compound at the designated location.

"Alkylcarbonylamino" is intended to include an alkyl group of an indicated number of carbon atoms attached through a carbonyl group to an amino group, where the amino group is attached to the residue of the compound at the designated location.

"Alkylcarbonyloxy" is intended to include an alkyl group of an indicated number of carbon atoms attached to a carbonyl group, where the carbonyl group is attached through an oxygen atom to the residue of the compound at the designated location.

"Alkynyl" is intended to include hydrocarbon chains of either a straight or branched configuration having one or more carbon-carbon triple bonds which may occur at any point along the chain that results in a stable structure.

"Amine protecting group" is intended to include any group known in the art of organic synthesis for the protection of amine groups. Such amine protecting groups include those listed in Greene et al. *Protective Groups in Organic Synthesis*; John Wiley & Sons: New York, 1991 and *The Peptides: Analysis, Synthesis, Biology*; Roberts et al. Eds.; Academic Press; New York, 1981; Vol. 3., the disclosures of which are hereby incorporated herein by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc);

(3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane types such as trimethylsilane; and (7) thiol containing types such as phenylthiocarbonyl and dithiasuccinoyl.

"Amino acid" is intended to include an organic compound containing both a basic amino group and an acidic carboxyl group. Included within this term are natural amino acids, modified and unusual amino acids, and amino acids which are known to occur biologically in free or combined form but usually do not occur in proteins. Among the modified and unusual amino acids are those disclosed in, for example, *The Peptides: Analysis, Synthesis, Biology*; Roberts et al. Eds.; Academic Press: New York, 1983; Vol. 5, p 342, the disclosure of which is hereby incorporated herein by reference. Modified or unusual amino acids which can be used to practice the invention include, but are not limited to, D-amino acids, hydroxylysine, 4-hydroxyproline, an N-Cbz-protected amino acid, ornithine, 2,4-diaminobutyric acid, homoarginine, norleucine, N-methylaminobutyric acid, naphthylalanine, phenylglycine, β-phenylproline, tert-leucine, 4-aminocyclohexylalanine, N-methylnorleucine, 3,4-dehydroproline, N,N-dimethylaminoglycine, N-methylaminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid and 2-benzyl-5-aminopentanoic acid.

"Amino acid residue" is meant to indicate that portion of an amino acid (as defined herein) that is present in a peptide.

"Any group that, when administered to a mammalian subject as part of a compound of Formula (I), cleaves to form a free hydroxyl, free amino or free sulfhydryl" is intended to include an OH, $NH_2$ or SH group wherein a hydrogen atom is replaced with a masking group such that the O—, NH—, or S-masking group combination, when administered to a mammalian subject, cleaves to form a compound having a free hydroxyl (OH), free amino ($NH_2$), or free sulfhydryl (SH) group, respectively. Examples of masking groups include, but are not limited to, $C_1$–$C_6$ alkyl substituted with 0–3 $R^{11}$, $C_3$–$C_6$ alkoxyalkyl substituted with 0–3 $R^{11}$, $C_1$–$C_6$ alkylcarbonyl substituted with 0–3 $R^{11}$, $C_1$–$C_6$ alkoxycarbonyl substituted with 0–3 $R^{11}$, $C_1$–$C_6$ alkylaminocarbonyl substituted with 0–3 $R^{11}$, benzoyl substituted with 0–3 $R^{12}$, phenoxycarbonyl substituted with 0–3 $R^{12}$, phenylaminocarbonyl substituted with 0–3 $R^{12}$, amine protecting groups, hydroxyl protecting groups and sulfhydryl protecting groups, where the masking group is subject to enzymatic cleavage or cleavage by other conditions present within the mammalian subject. "Any group that, when administered to a mammalian subject as part of a compound of Formula (I), cleaves to form a compound having two free hydroxyl groups, or two free amino groups, or one free hydroxyl and one free amino group", and "any group that, when administered to a mammalian subject as part of a compound of Formula (I), cleaves to form a free hydroxyl" includes the O-masking group and NH-masking groups referred to above.

"Aryl" or "aromatic residue" is intended to include phenyl, naphthyl and biphenyl.

"$C_7$–$C_{10}$ arylalkyl" is intended to refer to an aryl group attached through a $C_1$–$C_4$ alkyl group to the residue of the indicated compound.

"($C_1$–$C_3$ alkyl)aryl" is intended to refer to a $C_1$–$C_3$ alkyl group which is attached through an aryl ring to the residue of the indicated compound.

"Aryl ($C_1$–$C_3$ alkyl)" is intended to refer to an aryl group attached through a $C_1$–$C_3$ alkyl group to the residue of the indicated compound.

"Bicycloalkyl" is intended to include saturated bicyclic ring groups such as [3.3.0]bicyclooctane, [4.3.0]bicyclononane, [4.4.0]bicyclodecane (decalin), [2.2.2]bicyclooctane, and the like.

"Carbocycle" or "carbocyclic residue" or "carbocyclic ring system" is intended to include any stable 3- to 7-membered monocyclic or bicyclic ring, or any stable 7- to 14-membered bicyclic or tricyclic ring, or any stable polycyclic carbon ring having up to 26 members, any ring of which may be saturated, partially unsaturated, or aromatic. Examples of such carbocycles include, but are not limited to, cyclopropyl, cyclobutyl, cyclopentyl, cyclohexyl, phenyl, biphenyl, naphthyl, indanyl, adamantyl, and tetrahydronaphthyl (tetralin).

"Counterion" is intended to include small, negatively charged species such as chloride, bromide, hydroxide, acetate, sulfate, and the like.

"Cyclic urea compound" or "cyclic urea compounds" is intended to include all of the compounds encompassed by Formula (I), including urea and thiourea compounds having any of the designated substituents.

"Cycloalkoxy" is intended to include cycloalkyl groups of indicated carbon number attached through an oxygen atom to the designated position.

"Cycloalkyl" is intended to include saturated ring groups, including mono-, bi- and poly-cyclic ring systems, such as cyclopropyl, cyclobutyl, cyclopentyl, cyclohexyl, cycloheptyl, cyclooctyl and adamantyl. "Cycloalkylmethylene" is intended to include cycloalkyl groups of indicated carbon number attached through a methylene group to the designated position.

"Haloalkyl" is intended to include both branched and straight-chain saturated aliphatic hydrocarbon groups having the specified number of carbon atoms, substituted with 1 or more halogen atoms. "Halo" or "halogen" or "halide" is intended to include fluoro, chloro, bromo, and iodo.

"Heterocycle" or "heterocyclic ring" is intended to include stable 5- to 7- membered monocyclic or bicyclic rings and stable 7- to 10-membered bicyclic rings where the heterocycle may be either saturated or unsaturated, and where the heterocycle comprises from 1 to 4 heteroatoms independently selected from the group consisting of N, O and S, wherein the nitrogen and sulfur heteroatoms may optionally be oxidized, and the nitrogen heteroatom may optionally be quaternized, including a bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on a carbon or nitrogen atom if the resulting compound is stable. Examples of such heterocycles include, but are not limited to, acridinyl, azocinyl, benzimidazolyl, benzofuranyl, benzothiophenyl, carbazolyl, 4aH-carbazolyl, β-carbolinyl, chromanyl, chromenyl, cinnolinyl, decahydroquinolinyl, 2H, 6H-1,5,2-dithiazinyl, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindolinyl, isoindolyl, isoquinolinyl, isothiazolyl, isoxazolyl, morpholinyl, naphthyridinyl, octahydroisoquinolinyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, 4-piperidonyl, pteridinyl, purinyl, pyranyl, pyrazinyl, pyrazolidinyl, pyrazolinyl, pyrazolyl, pyridazinyl, pyridinyl, pyridyl, pyrimidinyl, pyrrolidinyl, pyrrolinyl, 2-pyrrolidinyl, pyrrolidonyl, pyrrolinyl, pyrrolyl, 2H-pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, thianthrenyl, thienyl, thiophenyl, triazinyl and xanthenyl. Also included are fused ring and spiro compounds containing, for example, the above heterocycles.

"Hydroxy" and "hydroxyl" are used interchangeably, and both are intended to include the "—OH" group.

"Hydroxyalkyl" is intended to include alkyl group which are bonded both to hydroxyl groups and to the residue of the indicated compound.

"Hydroxy protecting group" is intended to include any group known in the art of organic synthesis for the protection of hydroxyl groups. Such hydroxy protecting groups include those listed in Greene et al. *Protective Groups in Organic Synthesis*; John Wiley & Sons; New York, 1991, the disclosure of which is hereby incorporated herein by reference. Examples of hydroxy protecting groups include, without limitation, acyl types, aromatic carbamate types and alkyl types. Exemplary hydroxy protecting groups include, without limitation, methyl, methoxymethyl, methylthiomethyl, benzyloxymethyl, t-butoxymethyl, 2-methoxyethoxymethyl, 2,2,2-trichloroethoxymethyl, 2-(trimethylsilyl)ethoxymethyl, tetrahydropyranyl, tetrahydrofuranyl, t-butyl, triphenylmethyl, trimethylsilyl, triethylsilyl, t-butyldimethylsilyl, t-butyldiphenylsilyl, pivaloate or N-phenylcarbamate.

"Ketal group" or "ketal ring" is intended to include any ketal protecting group which can be hydrolyzed to form a carbonyl. Such ketal rings or ketal protecting groups are well known in the art of organic synthesis and typically include, for example, substituted or unsubstituted carbocyclic diethers, dithioethers, or mixed ethers. Such ketal protecting groups include those listed in Greene et al. *Protective Groups in Organic Synthesis*; John Wiley & Sons; New York, 1991.

"Leaving group" is meant to include a stable species that can be detached from a molecule during a reaction. More specifically, leaving groups are atoms or atomic groupings that are sufficiently stable in anionic form to detach from a carbon atom in response to nucleophilic attach at that carbon atom by a nitrogen atom. In other words, a nitrogen containing molecule will react with C—L to form a nitrogen-C bond and L in instances where L is a leaving group. Typical leaving groups include halides, such as fluoride, chloride, bromide and iodide. Many hydroxyl derivatives, e.g., derivatives prepared by the conversion of the hydroxyl group into the ester of a relatively strong acid, are leaving groups. Such alcohol derivative leaving groups include the para-toluenesulfonyl ester (tosylate group), methanesulfonyl ester (mesylate group) and acetate ester.

"Peptide" is meant to include a compound that consists of two or more amino acids (as defined herein) that are linked by means of a peptide bond. The term "peptide" also includes compounds containing both peptide and non-peptide components, such as pseudopeptide or peptide mimetic residues or other non-amino acid components. Such a compound containing both peptide and non-peptide components may also be referred to as a "peptide analog".

"Peptide bond" means a covalent amide linkage formed by loss of a molecule of water upon the joining of the carboxyl group of a first amino acid and the amino group of a second amino acid.

"Pharmaceutically acceptable salt" is intended to include all derivatives of the subject compound wherein the compound is modified by formation of its acid or base salt. Examples of pharmaceutically acceptable salts include, but are not limited to, mineral or organic acid salts of basic residues such as amines. Examples of pharmaceutically acceptable salts also include, but are not limited to, alkali or organic salts of acidic residues such as carboxylic acids, and the like. Pharmaceutically acceptable salts of the compounds of the invention can be prepared, for example, by reacting the free acid or base forms of these compounds with a stoichiometric amount of the appropriate base or acid in water or in an organic solvent, or in a mixture of the two. Nonaqueous media like ether, ethyl acetate, ethanol, isopropanol, or acetonitrile are preferred. Lists of suitable salts are found in *Remington's Pharmaceutical Sciences* 1985, 1418 (17th ed., Mack Publishing Company, Easton, Pa.,) the disclosure of which is hereby incorporated herein by reference.

"Prodrugs" are intended to include any covalently bonded carriers which release the active parent drug according to Formula (I) in vivo when such prodrug is administered to a mammalian subject. Prodrugs of a compound of Formula (II) are prepared by modifying functional groups present in the compound in such a way that the modifications are cleaved, either in routine manipulation or in vivo, to the parent compound. Prodrugs include compounds of Formula (II) wherein a hydroxy, amino, or sulfhydryl group is bonded to any group that, when the prodrug or compound of Formula (II) is administered to a mammalian subject, cleaves to form a free hydroxyl, free amino, or free sulfhydryl group, respectively. Examples of prodrugs include, but are not limited to, acetate, formate and benzoate derivatives of alcohol and amine functional groups in the compounds of Formula (II), and the like.

"Stable compound" and "stable structure" are meant to indicate a compound that is sufficiently robust to survive isolation to a useful degree of purity from a reaction mixture, and formulation into an efficacious therapeutic agent.

"Substituted", unless otherwise indicated, is intended to mean that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., $=O$) group, then 2 hydrogens on the atom are replaced.

When used in the context "substituted cyclic urea compound", the word "substituted" refers to the substituents on the urea or thiourea nitrogens.

The compounds described herein may have asymmetric centers. All chiral, diastereomeric, and racemic forms of the compounds of Formulas (I) and (II), or in any other Formula herein including Formulas (Ib), (Ic), (Id), (IIa) and (IIb), are intended. Compounds of the present invention containing an asymmetrically substituted atom may be isolated in optically active or racemic forms. It is well known in the art how to prepare optically active forms, such as by resolution of racemic forms or by synthesis from optically active starting materials.

The compounds described herein may have geometric isomers. All stable forms of geometric isomers of the compounds of Formulas (I) and (II), or in any other Formula herein including Formulas (Ib), (Ic), (Id), (IIa) and (IIb), are intended. Geometric isomers include the geometric isomers of carbon-carbon double bonds, carbon-nitrogen double bonds, rings, and the like, including both cis and trans isomers. All chiral, diastereomeric, racemic forms and all geometric isomeric forms of a structure are intended, unless the specific stereochemistry or isomeric form is specifically indicated.

When any variable (e.g., $R^4$ through $R^{41}$, $R^{44}$ through $R^{11A}$, etc.) occurs more than one time in any substituent or in Formulas (I) or (II), or in any other Formula herein including Formulas (Ib), (Ic), (Id), (IIa) and (IIb), its definition on each occurrence is independent of its definition at any other occurrence. Thus, for example, if a group is substituted with 0–3 $R^{11}$, then said group may optionally be substituted with up to three $R^{11}$ atoms or groups, and $R^{11}$ at each occurrence is selected independently from the defined list of possible $R^{11}$. Also, for example, in —N($R^{20}$)$_2$, each of the $R^{20}$ substituents may be independently selected from the list of possible $R^{20}$ groups defined. Also, combinations of substituents and/or variables are permissible only if such combinations result in stable compounds.

SYNTHETIC METHODS

The present invention provides an improved method for the preparation of N,N'-disubstituted cyclic urea compounds, and is particularly advantageous for the preparation of N,N'-non-symmetrically disubstituted cyclic urea compounds, and precursors thereof.

As used in this Section, the term "alkylated" or "alkylation" broadly refers to any method, or the product of such method, by which any substituent is placed onto a nitrogen atom of either the urea group of a cyclic urea compound or a terminal amino group of an acyclic amine precursor to a cyclic urea compound. The term "substituted" refers exclusively to a compound having substituents on the nitrogen atom of the urea group of a cyclic urea compound, or a substituent on the nitrogen atom of an acyclic amine precursor to a cyclic urea compound. The abbreviations "Bn" and "OMEM", as used in the structural formula within this section, refer to benzyl (—CH$_2$C$_6$H$_5$) and methoxyethoxymethoxy (—OCH$_2$OCH$_2$CH$_2$OCH$_3$) respectively.

According to one aspect of the invention, a diamine compound having two primary amine groups is selectively alkylated to provide a diamine compound having one primary and one secondary amine group. The mono-substituted diamine compound so prepared is then cyclized to a monosubstituted cyclic urea or thiourea compound, and subjected to a purification regime that removes by-products that may form during the alkylation or cyclization steps. The purified, monosubstituted cyclic urea compound is then alkylated at a nitrogen atom to provide an N,N'-disubstituted cyclic urea compound, where the substitution on the nitrogen atoms may be symmetrical or non-symmetrical. As a final step, the disubstituted cyclic urea compound is exposed to conditions sufficient to remove any protecting group that may be present.

A presently preferred method according to the invention to selectively alkylate a diamine compound having two primary amine groups is direct alkylation, as illustrated in SCHEME 1.

SCHEME 1

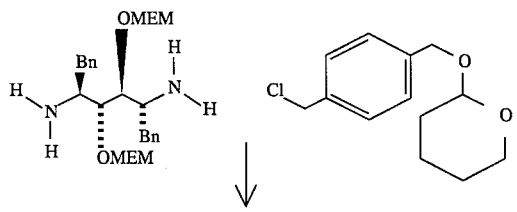

↓

-continued
SCHEME 1

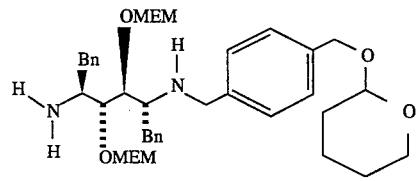

To achieve direct alkylation according to the invention, a diamine compound of Formula (IIa), e.g., (2R-(2R*,3S*,4S*,5R*))-3,4-bis((2-methoxyethoxy)methoxy)- 1,6-diphenyl-2,5-hexanediamine, is reacted with an alkylating agent of Formula $R^{16}X^1$. $R^{16}$ encompasses all the groups previously defined as $R^{22}$ or $R^{23}$, with the proviso that $R^{16}$ cannot be hydrogen. $X^1$ is a leaving group subject to nucleophilic displacement by a nitrogen of the diamine compound, where typical $X^1$ groups include halide, acetate, tosylate and mesylate. A non-limiting, suitable example of an alkylating agent includes 4-((((tetrahydro-2H-pyran-2-yl)oxy)methyl)phenyl)chloromethyl. The reaction of the diamine compound of Formula (IIa) with an alkylating agent yields an alkylated diamine of Formula (IIb), e.g., (2R-(2R*,3S*,4S*,5R*))-3,4-bis(( 2-methoxyethoxy)methoxy)-1,6-diphenyl-2—N-((4-(((tetrahydro- 2H-pyran-2-yl)oxy)methyl)phenyl)methyl)-2,5-hexanediamine.

Preferably, the diamine of Formula (IIa) and the alkylating agent are reacted in a diamine:alkylating agent molar ratio of about 1.0:1.0 to about 1.0:1.5, in the presence of an appropriate base, in an appropriate solvent and under an inert atmosphere. The reaction may optionally be conducted in the additional presence of a phase transfer reagent, where the presence of such a reagent is particularly preferred in those instances where the alkylating agent does not have a methylene group (—CH$_2$—) immediately adjacent to the leaving group $X^1$. The reaction is preferably conducted at room temperature, however may be conducted at temperatures as low as about 0° C. and up to and including the reflux temperature of the reaction and solvent mixture. Suitable inert atmospheres include atmospheres comprising mainly dry nitrogen or dry argon.

The reaction is preferably monitored by an appropriate analytical method, e.g., mass spectroscopy or high pressure liquid chromatography, so that the reaction period can be terminated when the starting diamine has been nearly consumed and before a substantial amount of di-alkylated diamine compound has begun to form. Monitoring also provides an indication that additional alkylating agent should be added. The reaction time is very dependent on the identity of the diamine of Formula (IIa) and the alkylating agent of Formula $R^{16}X^1$.

Exemplary solvents for the direct alkylation reaction include, without limitation, acetonitrile, water, tetrahydrofuran, N,N'-dimethylformamide, dimethoxyethane, dioxane, methylene chloride, chloroform, benzene and toluene.

Exemplary bases for the direct alkylation reaction include, without limitation, potassium carbonate (K$_2$CO$_3$), sodium carbonate (Na$_2$CO$_3$), lithium carbonate (Li$_2$CO$_3$), cesium carbonate (Cs$_2$CO$_3$), potassium bicarbonate (KHCO$_3$) and sodium bicarbonate (NaHCO$_3$).

Exemplary reagents and reagent systems to establish phase transfer conditions for the direct alkylation reaction include, without limitation, tetrabutylammonium iodide (TBAI) with potassium iodide (KI).

Under a preferred set of reaction conditions, the diamine of Formula (IIa) is dissolved at a concentration of about 0.03 to about 3.0 molar in acetonitrile, and about two equivalents of potassium carbonate ($K_2CO_3$) is used as the alkylation base.

Reductive amination is another presently preferred method according to the invention to selectively mono-alkylate a diamine compound having two primary amine groups. Reductive amination entails an amination reaction followed by a reduction reaction, as illustrated in SCHEME 2.

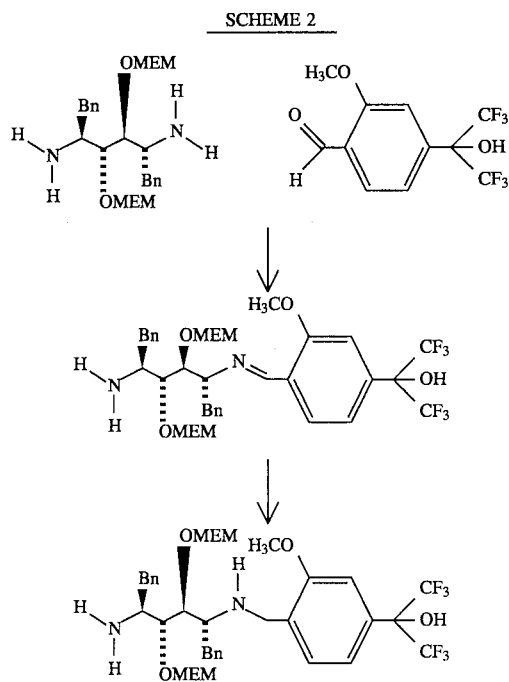

To achieve reductive amination according to the invention, a diamine compound of Formula (IIa), e.g., (2R-(2R*, 3S*,4S*,5R*))-3,4-bis((2-methoxyethoxy)methoxy)- 1,6-diphenyl-2,5-hexanediamine, is reacted with a carbonyl compound of a type as defined hereinafter, e.g., 4-(2,2,2-trifluoro- 1-hydroxy-1-(trifluoromethyl)ethyl)-2-methoxy-benzaldehyde, to provide an intermediate oxime compound. The intermediate oxime compound is reduced to yield an alkylated diamine of Formula (IIb), e.g., (2R-(2R*,3S*,4S*, 5R*))-3,4-bis((2-methoxyethoxy)methoxy)- 1,6-diphenyl-2-N-((2-methoxy- 4-(2,2,2-trifluoro-1-hydroxy-1-(trifluoromethyl)ethyl)phenyl)methyl)-2,5-hexanediamine.

Amination according to the invention is preferably achieved through reacting the diamine of Formula (IIa) with a carbonyl compound selected from the group consisting of $C_1$–$C_8$ alkane substituted with 0–3 $R^{31}$, $C_2$–$C_8$ alkene substituted with 0–3 $R^{31}$, $C_2$–$C_8$ alkyne substituted with 0–3 $R^{31}$, a $C_3$–$C_{14}$ carbocyclic ring substituted with 0–5 $R^{31}$ or 0–5 $R^{32}$, and a 5- to 10-membered heterocyclic ring containing 1 to 4 heteroatoms independently selected from oxygen, nitrogen or sulfur, the heterocyclic ring being substituted with 0–2 $R^{32}$, with the proviso that the carbonyl compound has at least one methylene group (—$CH_2$—) replaced with one carbonyl group (—C(=O)—).

The ratio of diamine:carbonyl compound is preferably in a molar ratio of about 1.0:1.0 to about 1.0:1.5. The amination reaction is preferably conducted in a solvent which provides for the azeotropic distillation of water, e.g., benzene. Other suitable techniques to achieve amide formation include reacting an amine compound and a carbonyl compound in the presence of anhydrous sodium sulfate, anhydrous potassium carbonate, molecular sieves, or titanium (IV) chloride.

Reduction of the imino group according to the invention is preferably achieved by reacting the product of an amination reaction with a reducing agent, where exemplary reducing agents include, without limitation, $NaBH_4$, lithium aluminum hydride ($LiAlH_4$), sodium cyanoborohydride ($NaBH_3CN$), borane complexes including $BH_3$.THF, $BH_3$.$SMe_2$, $BH_3$.amine including pyridine, and other borane compounds including $BH(OAc)_3$, $BH(O_2CCF_3)_2$, $NaBH(OAc)_3$, (t-butyl)NH $_2BH_3$, $LiBH(Et)_3$, $LiBH(t-butyl)_3$, $NaAlH_2(O(CH_2)_2OCH_3)$, LiBH (sec-butyl)$_3$ or $Zn(BH_3CN)_2$. Reduction of the imino group may also be achieved by heterogeneous catalytic hydrogenation, where suitable, non-limiting catalysts include Raney nickel, rhodium on alumina and $PtO_2$. Metal reductions may be accomplished with sodium or zinc-sodium hydroxide in alcohol.

The reaction is preferably monitored by an appropriate analytical technique, e.g., infrared spectroscopy, so that the reaction period can be terminated when essentially no carbonyl compound remains unreacted.

Acylation followed by reduction is yet another presently preferred method according to the invention to selectively mono-alkylate a diamine compound having two primary amine groups, as illustrated in SCHEME 3.

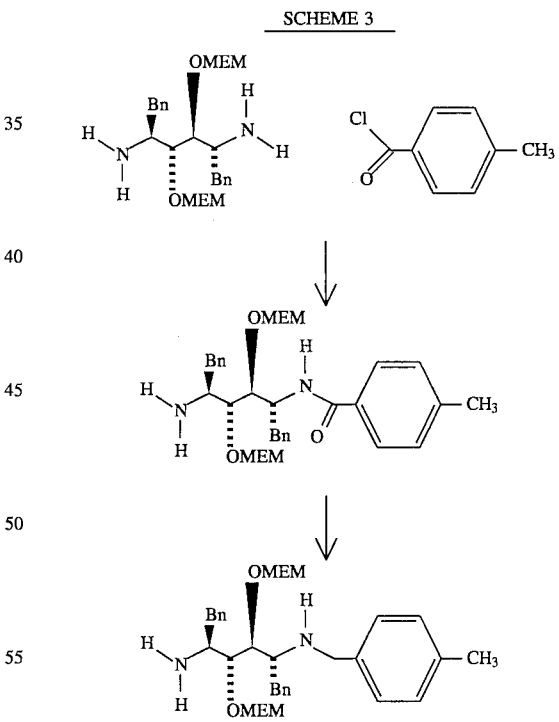

To achieve acylation followed by reduction according to the invention, a diamine compound of Formula (IIa), e.g., (2R-(2R*,3S*,4S*,5R*))-3,4-bis(( 2-methoxyethoxy)methoxy)-1,6-diphenyl-2,5-hexanediamine, is reacted with an acylating agent of Formula $R^{17}$ (C=O)$X^2$, as defined hereinafter, e.g., p-toluoyl chloride, to provide an intermediate amide compound. The intermediate amide compound is reduced with a reducing agent to yield an alkylated diamine of Formula (IIb), e.g., (2R-(2R*,3S*,4S*, 5R*))-3,4-bis(( 2-methoxyethoxy)methoxy)-1,6-diphenyl-2-N-(((4-methyl)phenyl)methyl)- 2,5-hexanediamine.

The acylating agent, $R^{17}(C=O)X^2$, is selected from compounds wherein:

(a) $R^{17}$ is selected from the group consisting of:
$C_1$-$C_7$ alkyl substituted with 0–3 $R^{31}$,
$C_2$-$C_7$ alkenyl substituted with 0–3 $R^{31}$, or
$C_2$-$C_7$ alkynyl substituted with 0–3 $R^{31}$; and (b) $X^2$ is a leaving group selected from the group consisting of halide, —O($R^{17}$) and —O(C=O)($R^{17}$).

Preferably, the diamine of Formula (IIa) and the acylating agent are reacted in a diamine:acylating agent molar ratio of about 1.0:1.0 to about 1.0:1.5. Preferably, the acylation reaction is conducted in an inert solvent, such as tetrahydrofuran, and under an inert atmosphere, such as an atmosphere comprising mainly dry nitrogen or dry argon.

The reduction reaction is achieved through use of a reducing agent, where preferred reducing agents include, without limitation, lithium aluminum hydride ($LiAlH_4$), $BH_3$.THF, $BH_3$.$SMe_2$, $B_2H_6$, $NaBH_4$ and $MeSO_3H$ in DMSO, $(Bu)_4NBH_4$ in methylene chloride, $NaBH_4$—$TiCl_4$ in dimethoxyethane, $NiCl_2$ in methanol, heterogeneous catalytic hydrogenation with Cu chromite, Ba/Cu chromite, Raney nickel, Raney cobalt, or rhenium on carbon. The reaction temperature for the reduction reaction is preferably between about room temperature and the reflux temperature of the reaction mixture.

Another aspect of the present invention are methods for preparing and purifying a cyclic urea compound of Formula (Ib), as illustrated in SCHEME 4.

SCHEME 4

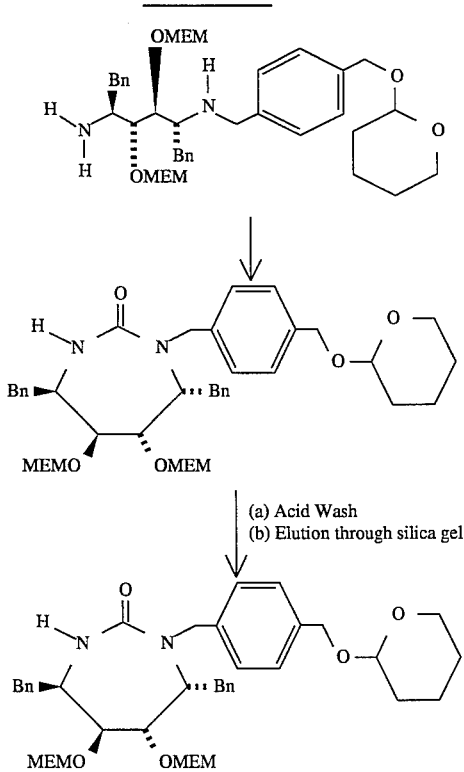

According to the invention, and as outlined in SCHEME 4, a diamine of Formula (IIb), e.g., (2R-( 2R*,3S*,4S*, 5R*))-3,4-bis((2-methoxyethoxy)methoxy)- 1,6-diphenyl-2-N-((4-(((tetrahydro-2H-pyran-2-yl)oxy)methyl)phenyl)methyl)-2,5-hexanediamine, having one primary amine group and one secondary amine group, is treated with carbonyl diimidazole to provide a cyclic urea of Formula (Ib), e.g., (4R-( 4a,5a,6b,7b))-hexahydro-5,6-bis((2-methoxyethoxy)methoxy)- 4,7-bis(phenylmethyl)-1-((4-(((tetrahydro- 2H-pyran-2-yl)oxy)methyl)phenyl)methyl)- 2H-1, 3-diazepin-2-one.

The cyclic urea of Formula (Ib) is purified by a regime comprising washing with an aqueous acid solution, followed by elution through a column or bed of silica gel. Washing is accomplished by combining a compound of Formula (Ib), and any associated impurities, with an aqueous acid solution, and agitating the combined solutions to allow partitioning between the aqueous and organic phases. Impurities that are more basic, i.e., have a smaller $pK_b$, than the compound of Formula (Ib), or that have a larger number of basic moieties, will preferentially partition into the aqueous phase. The partitioning is typically accomplished after only a few minutes of agitation. After the partitioning is complete, the aqueous phase is separated from the organic phase. After washing, the organic phase comprises the compound of Formula (Ib) in a purified form. If desired, the organic solvent may be removed from the compound of Formula (Ib), according to standard methods.

Further purification is achieved by eluting a compound of Formula (Ib), and associated impurities, through a column or bed of silica gel. Standard silica gels, as available from many commercial supply houses, may be used. In a preferred embodiment, the silica gel sits on a porous frit, where liquid can flow through the frit. The compound of Formula (Ib), and any associated impurities, are placed on top of a bed of silica gel, and eluted through the silica gel bed with one or more solvents. As the compounds elute through the silica gel, they will interact to various extents with the silica gel. Compounds which interact more strongly with the silica gel will elute more slowly through the silica gel. Compounds which interact slightly if at all with the silica gel will elute quickly, and can be collected free from the more strongly interacting compounds. In this way, compounds of Formula (Ib) can be separated from associated impurities.

In preparing the cyclic urea compounds according to the invention, the molar ratio of the diamine and either carbonyl diimidazole or thiocarbonyl diimidazole is approximately 1:1, although a slight excess of the diimidazole is preferred. The reaction with diimidazole is preferable conducted in a temperature range of between about 0° C. and about 38° C. It has been discovered that compounds having two secondary amine groups and no primary amine groups will not cyclize to form a cyclic urea compound under the preferred reaction conditions. A non-proteolytic solvent such as methylene chloride, chloroform, ethyl acetate, diethyl ether, tetrahydrofuran, dimethoxyethane, benzene, toluene or acetonitrile may also be present.

The aqueous acid solution used for the washing step preferably comprises a weak acid, such as citric acid. The concentration of acid can vary over a wide range, but is preferably about 10 weight percent. While stronger acids may frequently be employed in the washing step, their use may cause the deprotection or other undesirable transformation of the cyclic urea compound.

The elution through silica gel can be accomplished using any silica gel known in the art. A wide variety of elution solvents can be employed, with mixtures of hexanes and ethyl acetate (1:1), chloroform and ethyl acetate (3:2) and methylene chloride and ethyl acetate (3:2) being preferred.

Yet another aspect of the invention combines the alkylation chemistry illustrated in SCHEMES 1 through 3, with the cyclization chemistry and purification regime illustrated in SCHEME 4, where the sequential alkylation, cyclization and purification methods are generically illustrated in SCHEME 5.

secondary amine group, and will leave uncyclized a diamine compound having two secondary amine groups and no

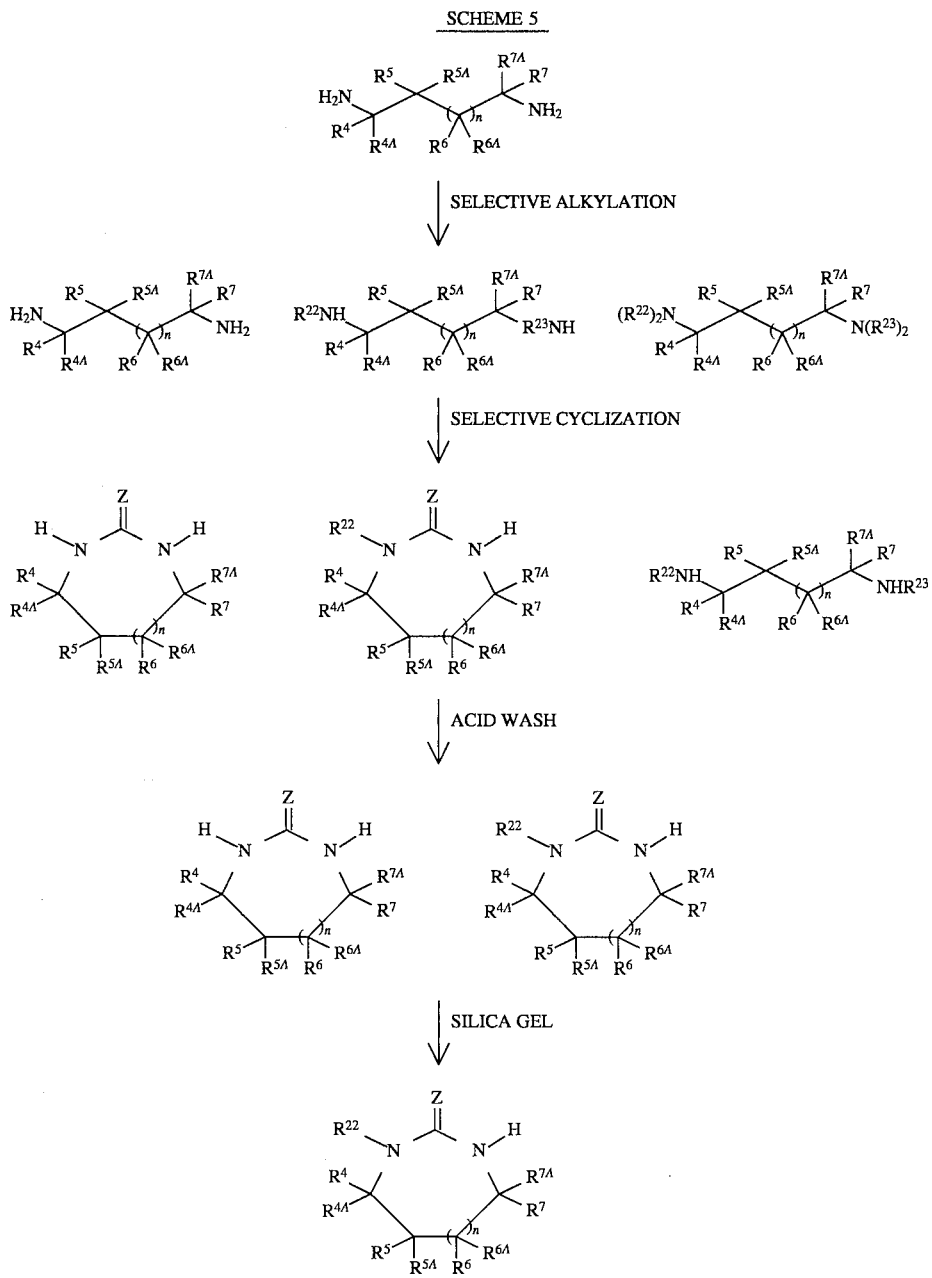

While the methodology of SCHEMES 1 through 3 will typically produce mono-alkylated diamine in surprisingly high yield, the mono-alkylated diamine will typically be present with some unreacted diamine and some di-alkylated diamine, i.e., starting material diamine and diamine in which both primary amine groups have been alkylated to provide a compound having two secondary amine groups, as shown in SCHEME 5.

The cyclization of a diamine mixture prepared according to any of SCHEMES 1 through 3, and according to the reaction conditions described herein, with carbonyl diimidazole or thiocarbonyl diimidazole, has been found to selectively cyclize diamine compounds having two primary amine groups, or having one primary amine group and one primary amine group. Thus, as shown in SCHEME 5, the cyclization chemistry according to the invention, when acting on the product mixture prepared according to any of the alkylation chemistries illustrated in SCHEMES 1 through 3, will provide cyclic ureas or thioureas having either no N-substitution, or N-substitution at only one of the urea or thiourea nitrogens.

The purification regime illustrated in SCHEME 4 is particularly advantageous when acting upon the product mixture obtained according to the chemistry illustrated in any of SCHEMES 1, 2 or 3. It has been found that during the wash with aqueous acid solution, the diamine having two secondary amine groups is preferentially solubilized in the aqueous phase, and the cyclic ureas or thioureas are preferentially solubilized in the organic phase. By separating the aqueous and organic phases after agitation, the di-alkylated diamine is separated from the cyclic urea compounds.

It has been found that unsubstituted cyclic urea compounds and mono-substituted cyclic urea compounds interact to different extents with silica gel, and will elute through a silica gel bed or column at different rates. It has been found that eluting a mixture of unsubstituted and mono-substituted cyclic urea compounds through silica gel allows for the separation of the unsubstituted cyclic urea compounds from the substituted cyclic urea compounds. The methodology according to the invention, and as illustrated in SCHEME 5, thus provides for a means by which a diamine having two primary amine groups can be converted to a purified form of a cyclic urea compound having N-substitution at only a single urea or thiourea nitrogen atom.

Still another aspect of the invention is a method for alkylating a cyclic urea compound having a substituent on one of the urea nitrogens, as obtained by the method illustrated in SCHEME 5, to provide a cyclic urea compound having a substituent at each of the urea nitrogens.

According to the invention, a cyclic urea compound having substitution at each of the urea nitrogens, and comprising at least one protected hydroxy, sulfhydryl or amino group, as prepared according to the methodology illustrated in SCHEME 6, is treated to reaction conditions sufficient to remove the protecting group(s) which may be present.

SCHEME 7

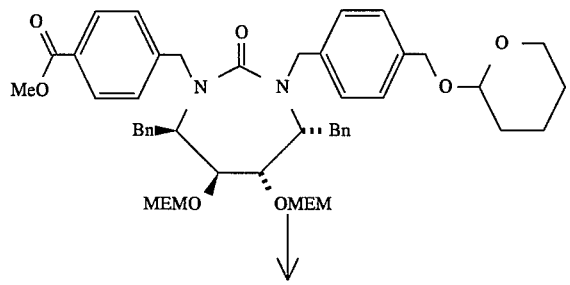

SCHEME 6

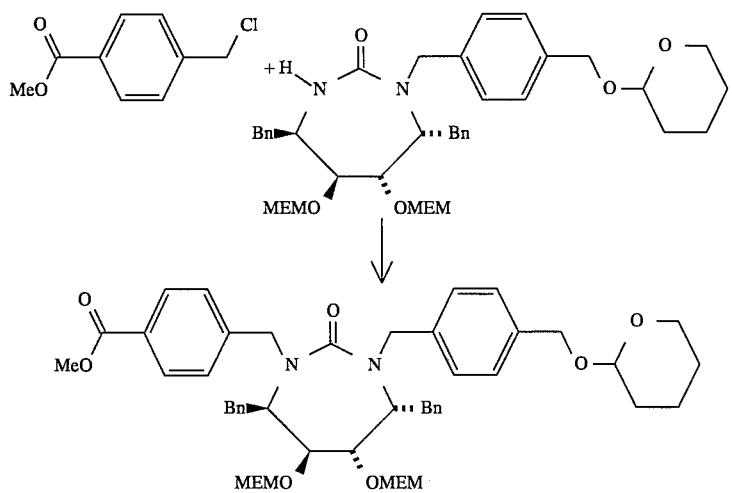

According to the invention, and as illustrated in SCHEME 6, a diamine of Formula (Ib), e.g., (4R-( 4α,5α,6β,7β))-hexahydro-5,6-bis((2-methoxyethoxy)methoxy)- 4,7-bis(phenylmethyl)-1-((4-(((tetrahydro- 2H-pyran-2-yl)oxy)methyl)phenyl)methyl)- 2H-1,3-diazepin-2-one, is treated with an alkylating agent of Formula $R^{16}X^1$, e.g., methyl (4-bromoethyl)benzoate, to provide a cyclic urea with substitution at both urea nitrogens, e.g., (4R-(4α,5α, 6β,7β))-methyl 4-((hexahydro-5,6-bis(( 2-methoxyethoxy)methoxy)-2-oxo-4,7-bis(phenylmethyl)- 3-((4-(((tetrahydro-2H-pyran-2-yl)oxy)methyl)phenyl)methyl)- 1H-1,3-diazepin-1-yl)methyl)benzoate. The method according to this aspect of the invention is particularly advantageous for the preparation of cyclic ureas having a substituent at each of the urea nitrogens where the substituents are not identical.

The alkylation may be conducted with a molar ratio of alkylating agent to cyclic urea compound of approximately 1:1, although a slight excess of alkylating agent is preferred. The alkylation is preferably conducted in the presence of a strong base, such as sodium hydride. The alkylation reaction is conveniently conducted at room temperature or at slightly elevated temperatures.

Compounds of Formula (Ic) include compounds having protected hydroxyl, sulfhydryl and/or amine groups.

-continued
SCHEME 7

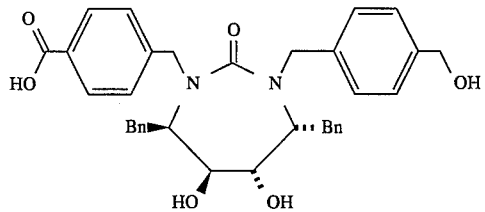

According to the invention, and as illustrated in SCHEME 7, a cyclic urea of Formula (Ic), e.g., (4R-(4α,5α,6β,7β))-methyl 4-((hexahydro-5,6-bis((2-methoxyethoxy)methoxy)-2-oxo-4,7-bis(phenylmethyl)-3-((4-(((tetrahydro-2H-pyran-2-yl)oxy)methyl)phenyl)methyl)- 1H-1,3-diazepin-1-yl)methyl)benzoate, is exposed to conditions sufficient to remove hydroxyl, sulfhydryl or amino protecting groups, and so provide a cyclic urea compound of Formula (Id), e.g., (4R-(4α,5α,6β,7β))-4-((hexahydro- 5,6-dihydroxy-3-((4-(hydroxymethyl)phenyl)methyl)- 2-oxo-4,7-bis(phenylmethyl)-1H-1,3-diazepin-1-yl) methyl) benzoic acid.

Protecting group removal is preferably accomplished by treating a protected cyclic urea compound with acid or base, depending on the susceptibility of the protecting group. Hydrochloric acid in either methanol or diethyl ether is a preferred acid. The deprotection is preferably run at room temperature, although temperatures above and below room temperatures may also be employed, depending on the reactivity of the cyclic urea compound and its stability to elevated temperatures.

EXAMPLES

The procedures of the invention are described in further detail with reference to the following specific, but non-limiting examples.

Abbreviations used in the Examples are defined as follows: "Bn" for benzyl, "brine" for saturated aqueous sodium chloride solution, "c" for concentration in grams per 100 mL, "CDI" for carbonyl diimidazole (CAS No. 13551-83-2), "cm" for centimeter, "d" for doublet, "dd" for doublet of doublets, "DMF" for N,N-dimethylformamide (CAS No. 68-12-2), "EtOAc" for ethyl acetate (CAS No. 141-78-6), "Et$_2$O" for ether (CAS No. 60-29-7), EtOH for ethanol (CAS No. 64-17-5), "g" for gram or grams, "h" for hour or hours, "HPLC" for high pressure liquid chromatography, "IR" for infrared spectroscopy, "m" for multiplet, "M" for molar, "Me" for methyl, "MeOH" for methyl alcohol (CAS No. 67-56-1), "MEM" for 2-methoxyethoxymethoxy, "MHz" for megahertz, "min" for minute or minutes, "mL" for milliliter or milliliters, "mmol" for millimole or millimoles, "mp" for melting point range, "MS" for mass spectroscopy, "MW" for molecular weight, "N" for normal or normality, when N is not used in a chemical formula as nitrogen, n-BuCl for n-butyl chloride (CAS No. 109-69-3) "nm" for nonometer, "NMR" for nuclear magnetic resonance spectroscopy, 'q' for quartet, "s" for singlet or singlets, 't' for triplet, "TBAI" for tetrabutylammonium iodide (CAS No. 311-28-4), "TFA" for trifluoroacetic acid (CAS No. 76-05-1), "THF" for tetrahydrofuran (CAS No. 109-99-9), "TLC" for thin layer chromatography, "TMS" for tetramethylsilane (CAS No. 75-76-3), "TMSC" for trimethylsilylchloride (CAS No. 75-77-4),and "v/v" for volume to volume ratio.

In the following Examples, and unless otherwise indicated, all reactions were conducted under a dry nitrogen atmosphere. The diamines of Formula (IIa) having n equal to 0, including (2R-( 2R*,3S*,4S*,5R*))-3,4-bis((2-methoxyethoxy)methoxy)- 1,6-diphenyl-2,5-hexanediamine and (4α(S),5β(S))- 2,2-dimethyl-α,α'-bis(phenylmethyl)-1,3-dioxolane-4,5-dimethanamine, may be prepared as described in copending commonly assigned U.S. patent application Ser. No. 07/714,042 ("Jadhav et al. "), filed May 31, 1991. Alternatively, synthetic methodology for preparing the diamines of Formula (IIa) is found in U.S. Pat. Nos. 4,837, 204 and 5,142,056, Canadian Patent Application No. 2,026, 832 and in Baker et al. *J. Org. Chem.* 1993, 58, 3277. The diamines of Formula (IIa) having n equal to 1 or 2 are conveniently prepared as described in Baker et al. *J. Org. Chem.* 1993, 58, 3277.

EXAMPLE 1

A. (2R-(2R*,3S*,4S*,5R*))-3,4-Bis ((2-methoxyethoxy)methoxy)-1,6-diphenyl-2-N-((4-(((tetrahydro-2H-pyran-2-yl)oxy)methyl)phenyl)methyl)-2,5-hexanediamine

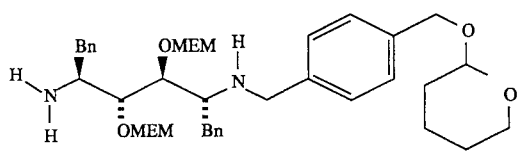

A mixture of (2R-(2R*,3S*,4S*,5R*))-3,4-bis((2-methoxyethoxy)methoxy)- 1,6-diphenyl-2,5-hexanediamine (15.9 g, 33.36 mmol) and 4-((((tetrahydro-2H-pyran-2-yl)oxy)methyl)phenyl)chloromethyl (8.03 g, 33.36 mmol) in 200 mL THF was treated with KHCO$_3$ (3.34 g, 33.36 mmol), KI (1 g, 6.02 mmol), and TBAI (1 g, 2.71 mmol). The reaction mixture was stirred until mass spectral analysis indicated no additional formation of the titled mono-alkylated diamine product (M+1=681) and the initial appearance of di-alkylated byproduct (M+1=885). The mixture was diluted with 300 mL water and 500 mL CH$_2$Cl$_2$. The organic phase was separated, dried over MgSO$_4$ and filtered to provide a filtrate containing the titled mono-alkylated diamine compound in greater than 72% yield.

B. (4R-(4α,5α,6β,7β))-Hexahydro-5, 6-bis((2-methoxyethoxy)methoxy)- 4,7-bis(phenylmethyl)-1-((4-(((tetrahydro-2H-pyran-2-yl)oxy)methyl)phenyl)methyl)-2H-1,3-diazepin-2-one

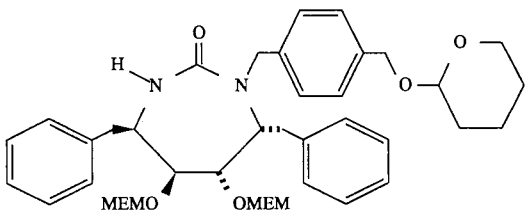

The filtrate from Example 1A was treated with CDI (6 g, 37 mmol) and stirred at room temperature until mass spectral analysis indicated that no mono-alkylated diamine starting material (M+1=681) remained in the reaction mixture. The mixture was diluted with 200 mL of 5% aqueous NaHCO$_3$ solution, and the organic phase was washed successively with water, 10% aqueous citric acid solution and brine. The organic phase was then dried over MgSO$_4$, filtered and concentrated to a viscous oil. The crude product was further purified by dissolving the oil in 100 mL hexanes/ EtOAc (1:1 v/v) and filtering the solution through a bed of silica gel. Appropriate fractions of the filtrate were combined and concentrated to an oil of constant weight, providing the titled mono-alkylated cyclic urea in 72% yield (based on the mass of (2R-(2R*,3S*,4S*,5R*))-3,4-bis((2-methoxyethoxy)methoxy)- 1,6-diphenyl-2,5-hexanediamine used in Example 1A). $^1$H NMR (300 MHz, CDCl$_3$, TMS) δ1.4–1.9 (m, 6H), 2.74 (dd, 1H), 3.04 (d, 2H), 3.24 (dd, 1H), 3.36 (2 S, 6H, CH$_3$), 3.39–3.80 (m, 12H), 3.8–4.0 (m, 3H), 4.45 (d, 1H), 4.58–4.9 (m, 8H), 7.1–7.35 (m, 14H, Ar); IR (CHCl$_3$ film) 1661 (C=O) cm$^{-1}$; MS (NH$_3$-CI) m/e 707 (M+1).

C. (4R-(4α,5α,6β,7β))-Hexahydro-5,6-dihydroxy-1-((4-(hydroxymethyl)phenyl)methyl)- 4,7-bis(phenylmethyl)-2H-1,3-diazepin-2-one

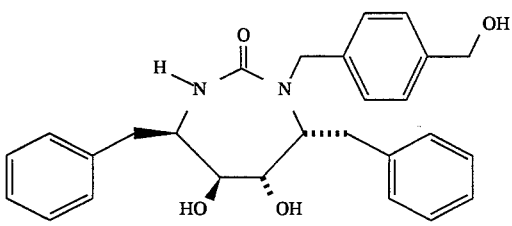

A solution of (4R-(4α,5α,6β,7β))-hexahydro-5,6-bis((2-methoxyethoxy)methoxy)-4,7-bis(phenylmethyl)- 1-((4-(((tetrahydro-2H-pyran-2-yl)oxy)methyl)phenyl)methyl)-2H-1,3-diazepin-2-one (1.43 g, 2.02 mmol, from Example 1B) in 25 mL MeOH was treated with 25 mL 1N HCl/Et$_2$O and stirred at room temperature for 16 h. The mixture was concentrated in vacuo, and the residue was recrystallized from MeOH/H$_2$O to give 0.90 g (99.6%) of the titled deprotected mono-alkylated cyclic urea. mp 198°–199° C.; $^1$H NMR (300 MHz, CDCl$_3$, D$_2$O, TMS) δ(2.74 (dd, 1H), 2.89 (d, 1H), 3.08 (m, 3H), 3.47 (m, 2H), 3.81 m, 1H), ArCH$_2$CHCHCHCHCH$_2$Ar), 3.55 (d, 1H, ArCHN ), 4.56 (s, 2H, ArCH$_2$O), 4.84 (d, 1H, ArCHN), (7.01 (d, 2H), 7.1–7.36 (m, 12H), Ar); IR (nujol) 3657–3100 (OH), 3427 (NH), 1610 (C=O) cm$^{-1}$; MS(NH$_3$-CI) m/e 447 (M+1); Analysis calc'd for C$_{27}$H$_{30}$N$_2$O$_4$ MW 446.55: C, 72.62; H, 6.77; N, 6.27; found: C, 71.91; H, 6.84; N, 6.23.

D. (4R-(4α,5α,6β,7β))-Methyl 4-((hexahydro-5,6-bis((2-methoxyethoxy)methoxy)-2-oxo-4,7-bis(phenylmethyl)- 3-((4-(((tetrahydro-2H-pyran-2-yl)oxy)methyl)phenyl)methyl)- 1H-1,3-diazepin-1-yl)methyl)benzoate

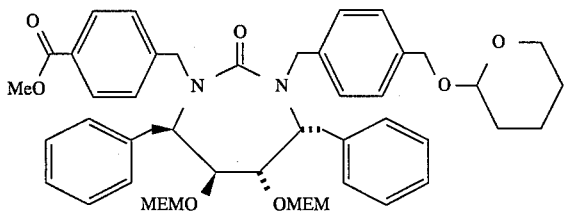

A solution of (4R-(4α,5α,6β,7β))-hexahydro-5,6-bis((2-methoxyethoxy)methoxy)-4,7-bis(phenylmethyl)- 1-((4-(((tetrahydro-2H-pyran-2-yl)oxy)methyl)phenyl)methyl)-2H-1,3-diazepin-2-one (6.0 g, 8.49 mmol, from Example 1B) in 50 mL dry DMF was treated with NaH (0.22 g, 9.3 mmol) and stirred at room temperature for 30 min. The mixture was then treated with methyl (4-bromoethyl)benzoate (1.94 g, 8.49 mmol) and stirred for 24 h. The mixture was poured into 300 mL 5% aqueous citric acid solution, and extracted with 200 mL CH$_2$C$_{12}$. The organic layer was washed with water and brine, dried over MgSO$_4$, filtered, and concentrated in vacuo to a gum. The gum was purified by flash chromatography over silica gel eluting with CHCl$_3$/EtOAc (3:2 v/v). Appropriate fractions were combined and concentrated to give 6.4 g (88%) of the titled unsymmetrically N,N'-disubstituted cyclic urea as an oil: MS(NH$_3$-CI) m/e 855 (M+1).

E. (4R-(4α,5α,6β,7β))-4-((Hexahydro-5,6-dihydroxy-3-(( 4-(hydroxymethyl)phenyl)methyl)-2-oxo-4,7-bis(phenylmethyl)- 1H-1,3-diazepin-1-yl)methyl)benzoic acid

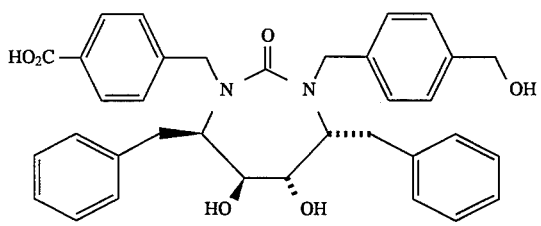

A solution of (4R-(4α,5α,6β,7β))-methyl 4-((hexahydro-5,6-bis((2-methoxyethoxy)methoxy)-2-oxo- 4,7-bis(phenylmethyl)-3-((4-(((tetrahydro-2H-pyran-2-yl)oxy)methyl)phenyl)methyl)- 1H-1,3-diazepin-1-yl)methyl)benzoate (2.4 g, 2.85 mmol, from Example 1D) in 25 mL dioxane and 10 mL water was treated with NaOH (1.14 g, 28.5 mmol) and stirred at room temperature for 24 h. The mixture was treated with concentrated HCl (6 mL) and stirred an additional 24 h before being concentrated in vacuo. The residue was triturated with 25 mL 1N HCl, and the resulting solid was collected by filtration, washed with water and Et$_2$O, and dried to give 1.60 g (96.7%) of the titled deprotected nonsymmetrically N,N'-disubstituted cyclic urea, which was shown to be about 97% pure according to analytical HPLC.

The titled compound (1.0 g, 97% pure) was further purified by preparative HPLC. Appropriate fractions were combined and concentrated in vacuo. The titled compound was isolated by trituration with water, collected by filtration, and dried at room temperature in vacuo to give 0.89 g (89% recovery) of the product which was determined by analytical HPLC to be greater than 98% pure. mp 128.0°–130.0° C.; R$_F$ 0.31 (CHCl$_3$/MeOH, 4:1 v/v); $^1$H NMR (300 MHz, DMSO-d6, D$_2$O, TMS) δ2.71–2.86 (m, 3H, CHCH$_2$), 2.86–3.06 (m, 3H, CHCH$_2$), 3.45 (m, 4H, CH$_2$O and 2 HCO), 4.44 (s, 2H, NCH$_2$), 4.65 (d, 2H, NCH$_2$), (6.95 (d, 2H), 7.04 (m, 4H), 7.26 (m, 10H), 7.87 (d, 2H), Ar); IR (KBr) 3390 (OH), 1698 (C=O) cm$^{-1}$; MS(NH$_3$-CI) m/e calc'd for C$_{35}$H$_{36}$N$_2$O$_6$+H (M+1): 581.265162, found 581.263623; 581 (M+1); [α]$_D^{20}$+96.00° (c=0.010, MeOH); Analysis calc'd for C$_{35}$H$_{36}$N$_2$O$_6$·0.5H$_2$O MW 589.69: C, 71.29; H, 6.32; N, 4.75; found: C, 71.58; H, 6.27; N, 4.78. Preparative HPLC was achieved by eluting with 0.1% TFA in CH$_3$CN/H$_2$O, 1/1 v/v, through a 5×25 cm ZORBAX C8 column, using a flow rate of 40→60 mL/min and detection at 230 nm @0.64 AUFS. Analytical HPLC was achieved by eluting with 0.1% TFA in CH$_3$CN/H$_2$O, 1:1 v/v, through a ZORBAX PRO-10 C8 column, using a flow rate of 1.0 mL/min and detection at 230 nm.

F. (4R-(4α,5α,6β,7β))-4-((3-((4-Formylphenyl)methyl) hexahydro-5,6-dihydroxy-4,7-bis(phenylmethyl)-1H-1,3-diazepin- 1-yl)methyl)benzoic acid

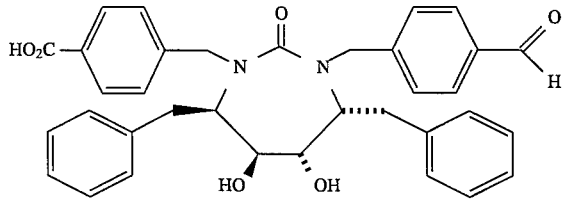

A solution of (4R-(4α,5α,6β,7β))-4-((hexahydro- 5,6-dihydroxy-3-((4-(hydroxymethyl)phenyl) methyl)-2-oxo-4,7-bis(phenylmethyl)-1H-1,3-diazepin-1-yl)methyl)benzoic acid (1.5 g, 2.58 mmol, from Example 1E) in 75 mL dioxane was treated with MnO$_2$ (11.22 g, 129.0 mmol) and stirred at room temperature for 24 h. Inspection by TLC(CHCl$_3$/MeOH, 8:2 v/v) showed remaining starting alcohol, and so an additional 4.3 g MnO₂ were added and stirring was continued for an additional 24 h. The mixture was filtered through Celite™, and the MnO₂-Celite™ bed was washed with 25 mL MeOH. The combined filtrate and washings were concentrated in vacuo to provide 1.05 g crude product as a foam. The foam was fractionally precipitated with EtOH/n-BuCl to give 0.202 g (13.6% yield) of the titled compound (>97% pure by analytical HPLC) and a filtrate solution.

The EtOH/n-BuCl filtrate solution was concentrated in vacuo and subjected to preparative HPLC. Appropriate fractions were combined and concentrated in vacuo. Fraction #1 contained 0.071 g starting alcohol, fraction #2 contained 0.500 g of the desired oxidized product, and fraction #3 contained 0.049 g of an unidentified material. Fraction #2 was triturated with water, and the resulting white solid was collected by filtration, washed with water, and dried at room temperature in vacuo to give 0.420 g of the titled aldehyde (greater than 98.5% pure by HPLC). Total yield of product having greater than 97% purity was 0.622 g (41.7%): mp 149.0°–151.0° C.; $R_F$ 0.37 (CHCl₃/MeOH (4: 1 v/v)); ¹H NMR (300 MHz, DMSO-d₆) δ2.76 (dd, 2H, CH₂Ph), 2.98 (d, 2H, CH₂-Ph), 3.04 (m, 2H, 2 NCH), 3.50 (m, 4H, CH₂N and 2 HCO), 4.1 (broad s, 1H, OH), 4.63 (d, 2H, NCH₂), 5.0 (broad s, 1H, OH), (6.94 (m, 4H), 7.24 (m, 8H), 7.35 (d, 2H), 7.87 (m, 4H), At), 9.97 (s, 1H, CHO), 12.85 (broad s, 1H, CO₂H); IR (KBr) 1700 (C=O) cm⁻¹; MS (NH₃-CI/DDIP) m/e calc'd for C₃₅H₃₄N₂O₆+NH₄(M+NH₄): 596.276061, found: 596.276656; 579(M+1), 596(M+NH₄); $[\alpha]_D^{20}$+109.00° (c=0.010, MeOH); Analysis calc'd for C₃₅H₃₄N₂O₆·H₂O, MW 596.68: C, 70.45; H, 6.08; N, 4.69; found: C, 70.44; H, 5.69; N, 4.69; analytical HPLC was conducted on a ZORBAX PRO—10 C₈ column (4.6× 250 mm) using 0.1% TFA in CH₃CN/H₂O, 1:1 v/v, as the solvent at a flow rate of 1.0 mL/min and detection at 230 nm; preparative HPLC was conducted on a 5×25 cm ZORBAX C8 column eluting with 0.1% TFA in CH₃CN/H₂O, 1:1 v/v, using a flow rate of 40→60 mL/min and detection at 230 nm @0.64 AUFS.

EXAMPLE 2

A. (2R-(2R*, 3S*, 4S*, 5R*))-3,4-Bis ((2-methoxyethoxy)methoxy)- 1,6-diphenyl-2-N-((2-methoxy-4-(2,2,2-trifluoro-1-hydroxy-1-(trifluoromethyl)ethyl)phenyl)methyl)- 2,5-hexanediamine

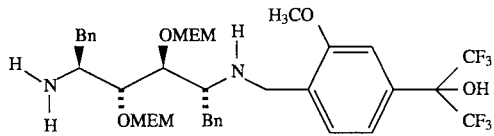

A mixture of (2R-(2R*, 3S*, 4S*, 5R*))-3,4-bis((2-methoxyethoxy)methoxy)- 1,6-diphenyl-2,5-hexanediamine (4.7 g, 9.96 mmol) and 2-methoxy-4-((2,2,2-trifluoro- 1-hydroxy-1-(trifluoromethyl)ethyl) benzaldehyde (2.98 g, 9.86 mmol, which may be prepared according to U.S. Pat. No. 4,727,180) in 100 g benzene were refluxed under Dean-Stark conditions for 3 h. The mixture was concentrated in vacuo, and the resulting oil was dissolved in THF and treated with NaBH₄ (0.38 g, 10.04 mmol). The mixture was stirred at room temperature for 1 h, refluxed for 16 h, then treated with 5 g MeOH and concentrated in vacuo. The residue was partitioned between 200 mL CH₂Cl₂ and 100 mL 5% aqueous NaHCO₃ solution. The organic phase was washed with brine, dried over MgSO₄, filtered, and concentrated to an oil. The oil was dissolved in 100 g CCl₄ and left standing at room temperature overnight to provide the disubstituted byproduct as a solid which was removed by filtration. The filtrate was concentrated in vacuo to a gum, and the gum was inspected by TLC and MS, and found to contain the titled mono-substituted diamine (m/e 763(M+1)) and a small amount of unreacted diamine (m/e 477(M+1)). The titled monosubstituted amine was formed in over 62 % yield.

B. (4R-(4α,5α,6β,7β))-Hexahydro-1-((2-methoxy-4-(2,2,2-trifluoro-1-hydroxy-1-(trifluoromethyl)ethyl)phenyl)methyl)-5,6-bis((2-methoxyethoxy)methoxy)- 4,7-bis(phenylmethyl)- 2H-1,3-diazepin-2-one

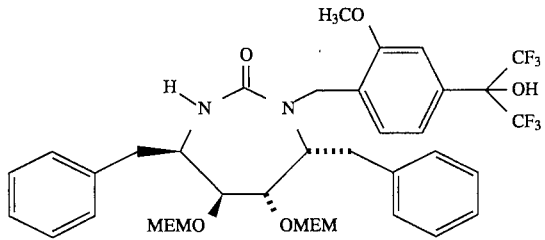

The product gum from Example 2A was dissolved in 150 g CH₂Cl₂, cooled to 0° C., and reacted with CDI (1.8 g, 11.1 mmol). The mixture was stirred at about 0° C. for 1 h, and then at room temperature for 16 h. The reaction mixture was sucessively washed with water, 5% aqueous NaHCO₃ solution, water, 10% aqueous citric acid solution, and brine, then dried over MgSO₄, filtered through a bed of 25 g silica gel and concentrated in vacuo to yield 4.8 g of the titled monosubstituted cyclic urea as a pure oil (TLC, CHCl₃/MeOH, 9:1 v/v, m/e 789 (M+1)), (62% yield based on the mass of (2R-(2R*, 3S*, 4S*, 5R*))-3,4-bis((2-methoxyethoxy)methoxy)- 1,6-diphenyl-2,5-hexanediamine used in Example 2A).

C. (4R-(4α,5α,6β,7β))-Hexahydro-1-((2-methoxy-4-(2,2,2-trifluoro-1-hydroxy-1-(trifluoromethyl)ethyl)phenyl)methyl)-3-((4-(((tetrahydro-2H-pyran-2-yl)oxy)methyl)phenyl)methyl)- 5,6-bis((2-methoxyethoxy)methoxy)- 4,7-bis(phenylmethyl)-2H-1,3-diazepin-2-one

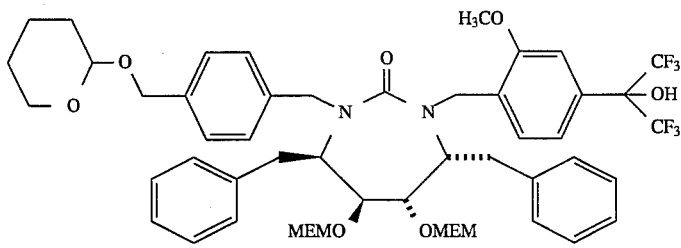

A solution of (4R-(4α,5α,6β,7β))-hexahydro-1-((2-methoxy-4-(2,2,2-trifluoro-1-hydroxy-1-(trifluoromethyl)ethyl)phenyl)methyl)- 5,6-bis((2-methoxyethoxy)methoxy)- 4,7-bis(phenylmethyl)-2H-1,3-diazepin-2-one (4.8 g, 6.085 mmol, from Example 2B) in 50 mL dry DMF was treated with NaH (0.16 g, 6.69 mmol) and stirred at room temperature for 30 min. The mixture was then treated with one equivalent of TMSC and stirred for 3 h. The mixture was then treated with an additional equivalent of NaH, stirred for 1 h, and treated with 4-(((((tetrahydro-2H-pyran- 2-yl)oxy)methyl)phenyl)chloromethyl (3.32 g, 13.8 mmol). The mixture was stirred for 72 h, then partitioned between 200 mL CH$_2$Cl$_2$ and 100 mL water. The organic phase was washed with water and brine, dried over MgSO$_4$, filtered and concentrated in vacuo to give the titled N,N'-unsymmetrically disubstituted cyclic urea compound as an oil. MS m/e 993 (M+1-TMS).

D. (4R-(4α,5α,6β,7β))-Hexahydro-5,6-dihydroxy-1-((4-(hydroxymethyl)-phenyl)methyl)- 4,7-bis(phenylmethyl)- 3-((2-methoxy-4-(2,2,2-trifluoro-1-hydroxy-1-(trifluoromethyl)ethyl)phenyl)methyl)- 2H-1,3-diazepin-2-one

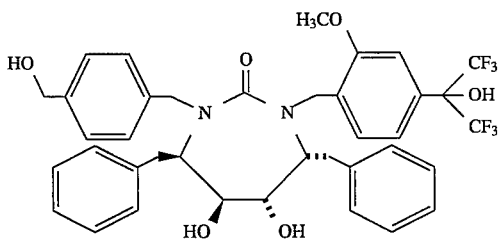

The oil prepared in Example 2C was dissolved in 50 mL MeOH, treated with 50 mL 1N HCl/Et$_2$O and stirred for 16 h at room temperature. The product solution was then concentrated in vacuo to give 2.0 g of crude product. The crude product was purified by preparative HPLC to give 0.467 g of the titled, deprotected, unsymmetrically N,N'-disubstituted cyclic urea as a foam. $^1$H NMR (300 MHz, CDCl$_3$, D$_2$O, TMS) δ2.53 (dd, 1H), 2.90 (d, 1H), 3.07 (d, 2H), 3.28 (m, 2H), 3.55 (s, 3H, OCH$_3$), 3.7–3.9 (m, 3H), 4.2–4.6 (m, 3H), 4.78 (d, 1H, ArCH$_2$N), (6.86 (d, 2H), 7.1–7.4 (m, 16H), Ar); $^{19}$F NMR (376.29 MHz, CDCl$_3$) δ–71.602 (q), –70.477 (q), collapses on heating; IR (KBr) 3388 (NH), 1634 (C=O) cm$^{-1}$; MS(NH$_3$-CI) m/e calc'd for C$_{38}$H$_{39}$F$_6$N$_2$O$_6$ (M+1): 733.272087 (M+1), found: 733.271232 (M+1); 733 (M+1); [α]$_D^{20}$+132.04° (c=0.206, MeOH). Preparative HPLC was conducted on a ZORBAX PRO-10 C8 column, at a flow rate of 1.0 mL/min, at 210 nm, using a solvent system of 49% EtOH, 49% H$_2$O, and 2% CH$_2$Cl$_2$.

EXAMPLE 3

A. (2R-(2R, 3S, 4S, 5R))-3,4-Bis((2-methoxyethoxy)methoxy)- 1,6-diphenyl-2—N-((3-nitrophenyl)methyl)- 2,5-hexanediamine

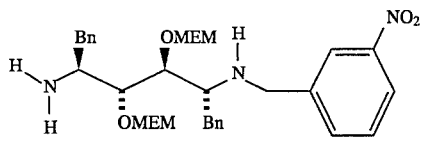

A solution of (2R-(2R*, 3S*, 4S*, 5R*))-3,4-bis((2-methoxyethoxy)methoxy)- 1,6-diphenyl-2,5-hexanediamine (3.2 g, 6.7 mmol) dissolved in 100 mL THF was treated with 3-nitrobenzyl bromide (1.15 g, 6.7 mmol), KI (1.08 g, 6.5 mmol), K$_2$CO$_3$ (0.9 g, 6.5 mmol) and TBAI (0.24 g, 0.65 mmol). The mixture was stirred at room temperature until mass spectral analysis indicated the formation of dialkylated material (m/e=747 (M+1)). The mixture was treated with additional 3-nitrobenzyl bromide (0.57 g, 3.25 mmol) and stirred for 24 h. The mixture was concentrated in vacuo, and the residue was partitioned between 200 mL CH$_2$Cl$_2$ and 100 mL water. The organic layer was washed with water and brine, dried over MgSO$_4$ and filtered to yield a solution containing the titled monosubstituted diamine formed in over 82% yield.

B. (4R-(4α,5α,6β,7β))-Hexahydro-5,6-bis((2-methoxyethoxy)methoxy)- 1-((3-nitrophenyl)methyl)- 4,7-bis(phenylmethyl)-2H-1,3-diazepin-2-one

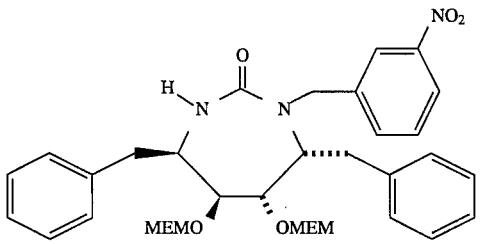

The filtrate solution from Example 3A was combined with CDI (1.09 g, 6.7 mmol) and the mixture stirred at room temperature for 24 h. The reaction mixture was then poured into 100 mL 10% aqueous citric acid solution. The organic layer was washed successively with 100 mL 10% aqueous citric acid solution, water and brine, then dried over MgSO$_4$ and filtered through silica gel (30 g). The filtrate was found to contain unreacted 3-nitrobenzyl bromide, and was discarded. The silica gel was washed with CHCl$_3$/EtOAc (3:2 v/v), and two fractions were collected.

Fraction #1 was concentrated in vacuo to an oil (2.1 g) which was homogenous (TLC, CHCl$_3$/EtOAc, 3:2 v/v) and identified by analytical methods to be the titled monosubstituted cyclic urea (49% yield): $^1$H NMR (300 MHz, CDCl$_3$, TMS) δ1.72 (broad s, 1H, NH), 2.66 (m, 1H), 3.07 (m, 2H), 3.21 (m, 1H), 3.34 (s, 3H, CH$_3$), 3.36 (s, 3H, CH$_3$), 3.4–4.0 (m, 12H), 4.64 (m, 1H), 4.7–4.9 (m, 5H), 7.1–7.35 (m, 10H, Ph), (7.42 (dd, 1H), 7.55 (d, 1H), 8.07 (m, 2H, 1,3-Ph)); IR (neat) 3340 (NH), 1662 (C=O) cm$^{-1}$; MS(NH$_3$-CDI)m/e 638 (M+1).

Fraction #2 was concentrated in vacuo to an oil (1.58 g) which was determined to contain greater than 90% of the titled monosubstituted cyclic urea and less than 10% of unsubstituted cyclic urea.

In total, the titled monosubstituted cyclic urea was prepared in 82% yield based on the mass of (2R-( 2R*, 3S*, 4S*, 5R*))-3,4-bis((2-methoxyethoxy)methoxy)- 1,6-diphenyl-2,5-hexanediamine used in Example 3A.

EXAMPLE 4

A. (2R-(2R*, 3S*, 4S*, 5R*))-3,4-Bis((2- methoxyethoxy)methoxy)- 1,6-diphenyl-2-N-((4-nitrophenyl)methyl)-2,5-hexanediamine

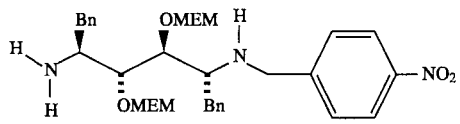

A solution of (2R-(2R*, 3S*, 4S*, 5R*))-3,4-bis((2-methoxyethoxy)methoxy)- 1,6-diphenyl-2,5-hexanediamine (3.2 g, 6.7 mmol), 4-nitrobenzyl bromide (1.15 g, 6.7 mmol), KI (1.08 g, 6.5 mmol), $K_2CO_3$ (0.9 g, 6.5 mmol) and TBAI (0.24 g, 0.65 mmol) in 50 mL THF was stirred at room temperature until mass spectral analysis indicated the initial formation of di-alkylated material (m/e=747 (M+1)). The mixture was treated with additional 4-nitrobenzyl bromide (0.57 g, 3.25 mmol) and stirred for 24 h. The mixture was concentrated in vacuo, and the residue partitioned between 200 mL $CH_2Cl_2$ and 100 mL water. The organic layer was washed with water and brine, dried over $MgSO_4$ and filtered to provide a solution containing the titled mono-alkylated diamine, formed in over 77% yield.

B. (4R-(4α,5α,6β,7β))-Hexahydro-5,6-bis((2-methoxyethoxy)methoxy)- 1-((4-nitrophenyl)methyl)-4,7-bis(phenylmethyl)-2H-1,3-diazepin-2-one

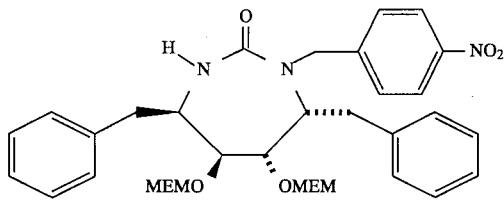

The filtrate solution from Example 4A was treated with CDI (1.09 g,.6.7 mmol) and the mixture stirred at room temperature for 24 h. The $CH_2Cl_2$ solution was washed successively with water, 10% aqueous citric acid solution, water and brine, then dried over $MgSO_4$ followed by filtration through silica gel (60 g). The filtrate was discarded, and the silica gel was washed with 300 mL $CHCl_3$/EtOAc (3:2 v/v). The washings were concentrated to an oil of constant weight to give 3.3 g of the titled mono-substituted cyclic urea ($C_{34}H_{43}N_3O_9$, MW 637.73), (77% yield based on the mass of (2R-(2R*, 3S*, 4S*, 5R*))-3,4-bis((2-methoxyethoxy)methoxy)- 1,6-diphenyl-2,5-hexane diamine used in Example 4A). $^1H$ NMR (300 MHz, $CDCl_3$, TMS) δ1.75 (broad s, 1H, NH), 2.5–2.9 (m, 2H), 3.3 (m, 1H), 3.36 (s, 3H, $CH_3$), 3.39 (s, 3H, $CH_3$), 3.5–4.2 (m, 13H), 4.64 (m, 1H), 4.7–5.15 (m, 5H), (7.0–7.4 (m, 12H), 8.04 (d, 2H, Ar)); IR (neat) 3332 (NH), 1719 (C=O) cm$^{-1}$; MS($NH_3$-CI) m/e 638(M+1).

EXAMPLE 5

A. (2R-(2R*, 3S*, 4S*, 5R*))-3,4-Bis((2-methoxyethoxy)methoxy)- 1,6-diphenyl-2-N-(3,3,3-trifluoropropyl)-2,5-hexanediamine

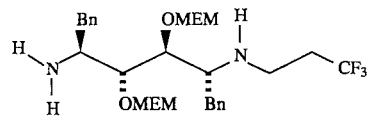

A solution of (2R-(2R*, 3S*, 4S*, 5R*))-3,4-bis((2-methoxyethoxy)methoxy)- 1,6-diphenyl-2,5-hexanediamine (3.19 g, 6.7 mmol) in 100 mL THF was treated with 3,3,3-trifluoro-1-iodopropane (1.5 g, 6.7 mmol), $K_2CO_3$ (0.93 g, 6.7 mmol) and refluxed for 4 h. The mixture was concentrated in vacuo, and the residue was partitioned between 150 mL $CH_2Cl_2$ and 100 mL water. The organic layer was washed with water and brine, dried over $MgSO_4$ and filtered to obtain a filtrate solution of the titled monosubstituted diamine, formed in over 83% yield. $^{19}F$ NMR (282.20 MHz, $CDCl_3$) δ–64.774 (t); MS($NH_3$-CI) m/e 477 (M+1)(starting material, diamine with two primary amine groups), 573 (M+1)(product, titled monosubstituted diamine), 611 (unknown).

B. (4S-(4α,5α,6β,7β))-Hexahydro-5,6-bis((2- methoxyethoxy)methoxy)-4,7-bis(phenylmethyl)-1-( 3,3,3-trifluoropropyl)-2H-1,3-diazepin-2-one

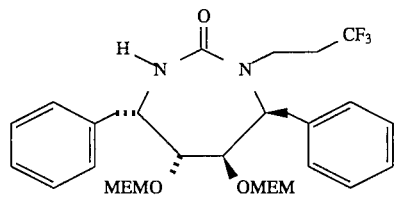

The $CH_2Cl_2$ filtrate solution from Example 5A was treated with CDI (1.1 g, 6.8 mmol) and stirred at room temperature for 3 h. The reaction mixture was poured into 100 mL 10% aqueous citric acid solution. The organic phase was isolated and washed with 100 mL 10% aqueous citric acid solution and brine, dried over $MgSO_4$, filtered, and concentrated in vacuo to an oil. The oil was flash chromatographed on silica gel eluting with $CHCl_3$/EtOAc (3:2 v/v), and appropriate fractions were combined and concentrated to give 3.32 g of the titled monosubstituted cyclic urea as an oil (83% yield based on the mass of (2R-( 2R*,3S*,4S*, 5R*))-3,4-bis((2-methoxyethoxy)methoxy)- 1,6-diphenyl-2,5-hexanediamine used in Example 5A). $^1H$ NMR (300 MHz, $CDCl_3$, TMS) δ1.78 (s, 1H, NH), 2.7–2.9 (m, 4H), 3.36 (s, 6H, $CH_3$), 3.5–4.3 (m, 12H), 4.65–5.15 (m, 8H), 7.05–7.4 (m, 10H, Ar); $^{19}F$ NMR (282.20 MHz, $CDCl_3$) δ–65.734 (t); IR (neat) 3330 (NH), 1658 (C=O) cm$^{-1}$; MS($NH_3$-CI) m/e 599(M+1).

EXAMPLE 6

A. (2R-(2R*,3S*,4S*,5R*))-3,4-Bis((2-methoxyethoxy)methoxy)- 1,6-diphenyl-2-N-phenylmethyl-2, 5-hexanediamine

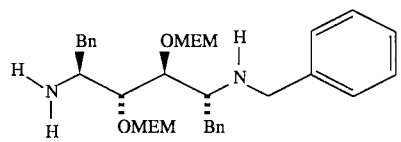

(2R-(2R,3S,4S,5R))-3,4-Bis ((2-methoxyethoxy)methoxy)- 1,6-diphenyl-2,5-hexanediamine (3.2 g, 6.7 mmol), $K_2CO_3$ (0.90 g, 6.5 mmol), KI (1.08 g, 6.5 mmol), benzyl chloride (0.82 g, 6.5 mmol) and TBAI (0.24 g, 0.65 mmol) were dissolved in 50 g THF. The mixture was stirred at room temperature until the desired monosubstituted diamine had ceased to form as evidenced by mass spectral analysis. The reaction mixture was treated with additional benzyl chloride (0.41 g, 3.25 mmol) and stirred for an additional 24 h. The mixture was concentrated in vacuo, and the residue was partitioned between 200 mL CH$_2$Cl$_2$ and 100 mL water. The organic layer was washed with brine, dried over MgSO$_4$ and filtered. The resultant filtrate solution contained the titled monosubstituted diamine in over 75% yield.

B. (4R-(4α,5α,6β,7β))-Hexahydro-5, 6-bis((2-methoxyethoxy)methoxy)- 1,4,7-tris (phenylmethyl)-2H-1,3-diazepine-2-thione

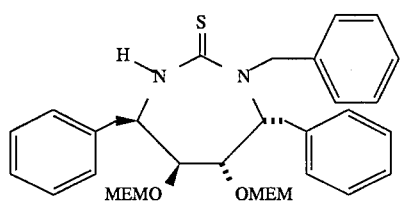

The filtrate solution from Example 6A was treated with thiocarbonyl diimidazole (1.19 g, 6.7 mmol) and stirred at room temperature for 24 h. The reaction mixture was washed with water, washed two times with 100 mL 10% aqueous citric acid solution, and then washed with brine. The solution was dried over MgSO$_4$, filtered and concentrated to an oil. The oil was flash chromatographed on silica gel eluting with CHCl$_3$/EtOAc (6:4 v/v), and appropriate fractions were concentrated in vacuo to provide 3.09 g of the titled monosubstituted cyclic thiourea as a homogeneous oil (75.8% yield based on the mass of (2R*, 3S*, 4S*, 5R*)-3, 4-bis((2-methoxyethoxy)methoxy)- 1,6-diphenyl-2,5-hexanediamine used in Example 6A).

$^1$H NMR (300 MHz, CDCl$_3$, TMS) δ1.63 (broad s, 1H, NH), 2.7–3.25 (3 m, 4H), 3.3–3.7 (m, 16H), 3.75–4.0 (2 m, 3H), 4.50 (dd, 1H), 4.72 (dd, 1H), 4.81 (m, 2H), 5.74 (m, 1H), 7.1–7.45 (m, 15H, Ar); IR (neat) 3378 (NH) cm$^{-1}$; MS(NH$_3$-CI) m/e 609 (M+1).

EXAMPLE 7

A (2R-(2R*, 3S*, 4S*, 5R*))-3,4-Bis((2-methoxyethoxy)methoxy)- 1,6-diphenyl-2-N-((3-benzonitrile)methyl)- 2,5-hexanediamine

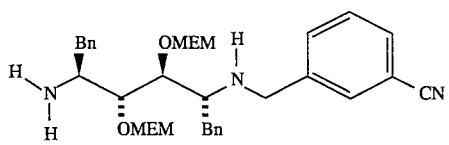

A solution of (2R-(2R*, 3S*, 4S*, 5R*))-3,4-bis((2-methoxyethoxy)methoxy)- 1,6-diphenyl-2,5-hexanediamine (3.2 g, 6.7 mmol), α-bromo-m-tolunitrile (1.31 g, 6.7 mmol) and K$_2$CO$_3$ (0.93 g, 6.7 mmol) in 150 mL acetonitrile was stirred at room temperature for 16 h. The insoluble material was removed by filtration to provide a filtrate solution of the titled mono-alkylated diamine in over 90% yield.

B. (4R-(4α,5α,6β,7β))-3-((Hexahydro-5,6-bis((2-methoxyethoxy)methoxy)- 2-oxo-4,7-bis(phenylmethyl)-1H-1,3-diazepin-1-yl) methyl)benzonitrile

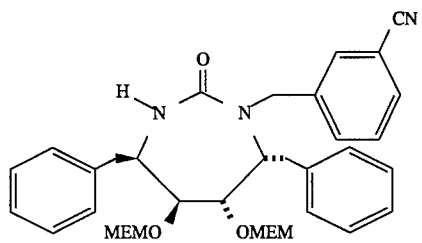

The filtrate solution from Example 7A was treated with CDI (1.1 g, 6.8 mmol) and stirred at room temperature for 24 h. The reaction mixture was washed with water, 10% aqueous citric acid solution, and brine, then dried over MgSO$_4$, filtered and concentrated in vacuo to an oil (3.90 g). The oil was dissolved in CHCl$_3$/EtOAc (3:2 v/v) and filtered through 60 g silica gel. The silica gel was washed with additional CHCl$_3$/EtOAc (3:2 v/v) until TLC indicated no additional product was eluting off the column. Appropriate fractions were combined and concentrated to give 3.75 g of the titled monosubstituted cyclic urea as an oil (90.6% yield based on the mass of (2R-(2R*, 3S*, 4S*, 5R*))-3, 4-bis((2-methoxyethoxy)methoxy)-1,6-diphenyl-2,5-hexanediamine used in Example 7A). $^1$H NMR (300 MHz, CDCl$_3$, TMS) δ2.6 (m, 1H), 3.03 (m, 2H), 3.2 (m, 1H), 3.36 (s, 6H, CH$_3$), 3.4–4.2 (m, 13H), 4.5–4.85 (m, 6H), 7.1–7.56 (m, 14H, Ar); IR (neat) 3338 (NH), 2229 (CN), 1662 (C=O) cm$^{-1}$; MS(NH$_3$-CI) m/e 618 (M+1).

EXAMPLE 8

A. (2R-(2R*, 3S*, 4S*, 5R*))-3,4-Bis((2-methoxyethoxy)methoxy)- 1,6-diphenyl-2-N-(((4-methyl)phenyl)methyl)- 2,5-hexanediamine

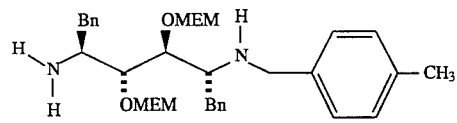

A solution of (2R-(2R*, 3S*, 4S*, 5R*))-3,4-bis((2-methoxyethoxy)methoxy)- 1,6-diphenyl-2,5-hexanediamine (3.19 g, 6.7 mmol) in 100 mL THF was acylated by stirring for 48 h at room temperature in contact with p-toluoyl chloride (1.14 g, 7.4 mmol). The resultant intermediate amide was concentrated in vacuo, and the residue partitioned between 150 mL CH$_2$Cl$_2$ and 100 mL 5% aqueous NaHCO$_3$ solution. The organic phase was washed with water and brine, dried over MgSO$_4$, filtered and concentrated in vacuo to provide 4.19 g of an oily mixture containing the intermediate amide. IR (neat) 3457 and 3328 (NH), 1643 (C=O) cm$^{-1}$; MS (NH$_3$-CI) m/e 595 (M+1).

Reduction of the intermediate amide was achieved by treating the oily mixture with excess 1M BH$_3$.THF, stirring at room temperature for 1 h and refluxing for 6 h. The mixture was cooled to room temperature and treated with 50 mL MeOH, refluxed for 1 h and concentrated in vacuo. The residue was added to 200 mL Et$_2$O and 100 mL 1 N NaOH, and stirred at room temperature for 24 h. The entire mixture was filtered through Celite™, and the organic layer was separated, washed with brine, dried over MgSO$_4$, filtered and concentrated to provide 3.66 g of an oil containing the titled monosubstituted diamine compound formed in over 32% yield.

B. (4R-(4α,5α,6β,7β))-Hexahydro-5,6-bis((2-methoxyethoxy)methoxy)- 1-((4-methylphenyl)methyl)- 4,7- bis(phenylmethyl)-2H-1,3-diazepin-2-one

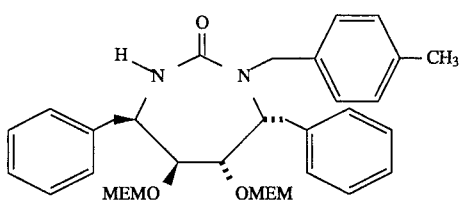

The product oil (3.66 g) from Example 8A and CDI (1.2 g, 7.4 mmol) were dissolved in 100 mL CH$_2$Cl$_2$ and stirred for 24 h at room temperature. The reaction mixture was washed with water, 10% aqueous citric acid solution, and brine, then dried over MgSO$_4$, filtered and concentrated in vacuo. The residue was purified by column chromatography (CHCl$_3$/EtOAc, 3:2 v/v) to give 1.30 g of the titled monosubstituted cyclic urea (32% yield based on the mass of (2R-( 2R, 3S, 4S, 5R))-3,4-bis((2-methoxyethoxy)methoxy)-1,6-diphenyl- 2,5-hexanediamine used in Example 8A). R$_F$ 0.78 (CHCl$_3$-MeOH, 9:1); $^1$H NMR (300 MHz, CDCl$_3$, TMS) δ2.40 (s, 3H, CH$_3$), 2.5–3.2 (m, 6H), 3.34 (s, 3H, CH$_3$), 3.38 (s, 3H, CH$_3$), 3.45–4.0 (m, 10H), 4.60 (m, 1H), 4.7–4.95 (m, 6H), 5.35 (s, 1H), (7.05–7.45 (m, 12H), 7.58 (d, 2H, Ar)); IR (neat) 3363 (NH), 1656 (C=O) cm$^{-1}$; MS(NH$_3$-CI) m/e 607 (M+1).

EXAMPLE 10

A. (2R-(2R*, 3S*, 4S*, 5R*))-3,4-Bis((2-methoxyethoxy)methoxy)- 1,6- diphenyl-2-N-(3-(2-(4-fluorophenyl)- 5,5-dimethyl-1,3-dioxane-2-yl) propyl)-5 2,5-hexanediamine

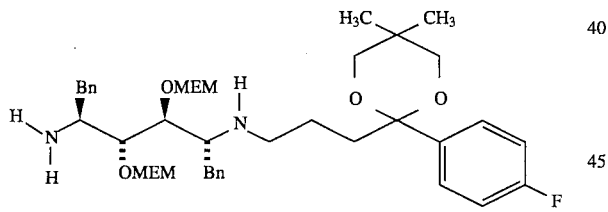

A solution of (2R-(2R*, 3S*, 4S*, 5R*))-3, 4-bis((2-methoxyethoxy)methoxy)- 1,6-diphenyl-2,5-hexanediamine (12.8 g, 26.85 mmol), 3-(2-(4-fluorophenyl)-5,5-dimethyl-1,3-dioxane-2-yl)-1-chloropropane (7.7 g, 26.85 mmol, prepared by conventional methods from the commercially available ketone), KI (4.46 g) and K$_2$CO$_3$ (3.7 g, mmol) in 150 mL acetonitrile was refluxed for 48 h and then concentrated in vacuo. The residue was partitioned between 200 mL CH$_2$Cl$_2$ and 100 mL water. The organic layer was washed with additional water and brine, dried over MgSO$_4$ and filtered to provide the titled monosubstituted diamine in over 55% yield.

B. (4R-(4α,5α,6β,7β))-1-(3-(2-(4-Fluorophenyl)-5,5-dimethyl- 1,3-dioxan-2-yl)propyl)hexahydro-5,6-bis((2-methoxyethoxy)methoxy)- 4,7-bis-(phenylmethyl)-2H-1,3-diazepin-2-one

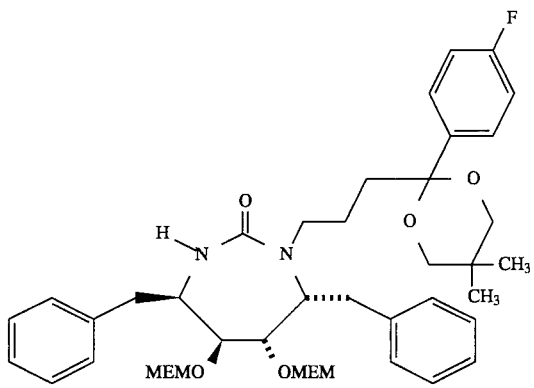

The reaction product from Example 10A was treated with 1.1 equivalents of CDI, and stirred at room temperature until no starting amine was evidenced by TLC(CH$_2$Cl$_2$-EtOAc, 3:2). The mixture was partitioned with 100 mL 10% aqueous citric acid solution, and the organic layer was washed with water and brine, dried over MgSO$_4$, filtered and concentrated to an oil. The oil was column chromatographed on silica gel eluting with CHCl$_3$/EtOAc (3:1 v/v), and appropriate fractions were combined and concentrated in vacuo to give 11.16 g of the titled monosubstituted cyclic urea as an oil (55% yield based on the mass of (2R-(2R* 3S* 4S* 5R*))-3,4-bis(( 2-methoxyethoxy)methoxy)-1,6-diphenyl-2, 5-hexanediamine used in Example 10A). $^1$H NMR (300 MHz, CDCl$_3$, TMS) δ0.52 (s, 3H, CH$_3$), 1.16 (s, 3H, CH$_3$), 1.45–1.7 (2 m, 4H, CH$_2$CH$_2$), 1.95 (s, 1H), 2.77 (m, H), 3.04 (m, 2H), 3.26 (m, 1H), 3.29 (s, 4H), 3.33 (m, 1H), 3.38 (s, 6H, CH$_3$), 3.57 (m, 6H), 3.73 (m, 2H), 3.85 (m, 3H), 3.98 (m, 1H), 4.55 (m, 1H), 4.87 (m, 4H), (6.96 (dd, 2H), 7.1–7.35 (m, 12H), Ar); $^{19}$F NMR (282 MHz, CDCl$_3$) δ114.99; IR (neat) 3343 (NH), 1663 (C=O) cm$^{-1}$; MS(NH$_3$-CI) m/e 753(M+1).

C. (4R-(4α,5α,6β,7β))-1-(4-(4-Fluorophenyl)-4-oxobutyl)hexahydro- 5,6-dihydroxy-4,7-bis(phenylmethyl)-2H-1,3-diazepin-2-one

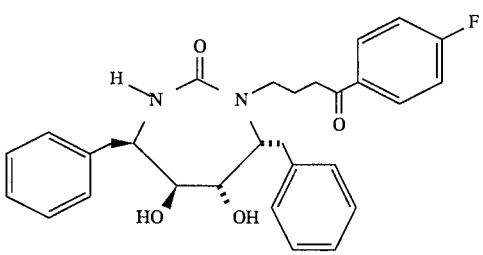

The monosubstituted cyclic urea oil of Example 10B (1.21 g, 1.61 mmol) in 5 mL MeOH was treated with 5 mL 10% HCl in MeOH and stirred at room temperature for 16 h. The mixture was diluted to 100 mL with 1N HCl, and the resulting precipitate was collected by filtration, washed with water, dried, washed with hexanes, recrystallized from CHCl$_3$, and dried to give 0.69 g (87%) of the titled deprotected monosubstituted cyclic urea as a solid. mp 171°–172° C.; $^1$H NMR (300 MHz, CDCl$_3$, TMS) δ1.8 (m, 2H), 2.4 (m, 1H), 2.7 (m, 3H), 3.15 (m, 3H), 3.5 (m, 4H), 3.75 (m, 1H), 3.96 (m, 2H), 5.13 (m, 1H), (7.06 (dd, 2H), 7.85 (m, 2H), 4-F-Ph), 7.26 (m, 10H, Ph); $^{19}$F NMR (282 MHz, CDCl$_3$) δ–105.52; IR (nujol) 3352 (OH), 1686 (C=O), 1630 (C=O) cm$^{-1}$; MS(NH$_3$-CI) m/e 491(M+1); [α]$_D^{20}$+107.92° (c=0.202, MeOH); Analysis calc'd for C$_{29}$H$_{31}$FN$_2$O$_4$ MW 490.58: C, 71.00; H, 6.37; N, 5.71; found: C, 70.96; H, 6.67; N, 5.70.

D. (4R-(1(R,S),4α,5α,6β,7β))-1-(4-(4-Fluorophenyl)-4-hydroxybutyl)-hexahydro-5,6-dihydroxy-4,7-bis(phenylmethyl)- 2H-1,3-diazepin-2-one

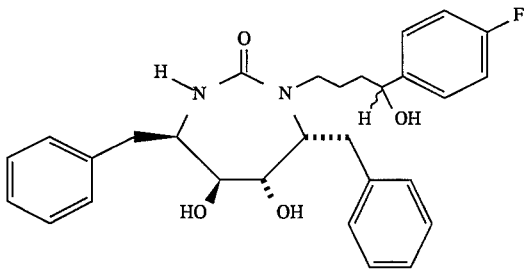

A solution of (4R-(4α,5α,6β,7β))-1-(4-(4-fluorophenyl)-4-oxobutyl)hexahydro-5,6-dihydroxy-4,7-bis(phenylmethyl)- 2H-1,3-diazepin-2-one (0.300 g, 0.61 mmol, from Example 10C) in 10 mL isopropanol was treated with NaBH$_4$ until no starting ketone was evidenced by TLC(CHCl$_3$/MeOH, 9:1 v/v). The mixture was treated with 10 mL 1N HCl, stirred for 30 min and concentrated in vacuo. The residue was partitioned between 20 mL CHCl$_3$ and 25 mL 1N HCl, and the organic layer was washed with water and brine, dried over MgSO$_4$, filtered, and concentrated to an amorphous solid. The crude product was recrystallized from CHCl$_3$/hexanes to give 0.286 g of the desired titled alcohols (95% yield. mp 168°–172° C.; $^1$H NMR (300 MHz, DMSO-d$_6$, TMS) δ(1.03–1.5 (m, 3H), 1.84 (m, 1H), CH$_2$CH$_2$C*), 2.65 (m, 1H, CH), 2.96 (m, 3H, ARCH$_2$+CH), 3.24 (m, 1H, CH), 3.39 (m, 2H, NCH$_2$), 3.66 (m, 2H, OCH), 4.40 (t, 1H, OCH), 5.2 (broad s, 3H, OH), 6.00 (s, 1H, NH), 7.0–7.3 (m, 14H, Ar); $^{19}$F NMR (282 MHz, DMSO-d$_6$) δ–116.34 (m), –116.37 (m); IR (nujol) 3345 (OH), 1622 (C=O) cm$^{-1}$; MS(NH$_3$-CI)m/e 493(M+1); $[α]_D^{20}$ +121.17° (c=0.222, MeOH); Analysis calc'd for C$_{29}$H$_{33}$FN$_2$O$_4$, MW 492.59: C, 70.71; H, 6.75; N, 5.69; found: C, 70.66; H, 6.83; N, 5.60.

E. (4α,5α,6β,7β)-1-(4-(4-fluorophenyl)-4-(hydroxyimino)butyl)hexahydro- 5,6-dihydroxy-4,7-bis(phenylmethyl)-2H-1,3-diazepin-2-one

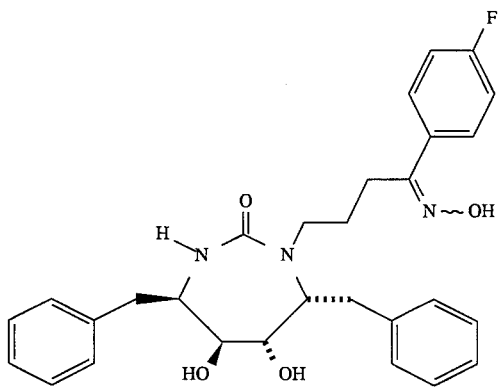

A mixture Of (4R-(4α,5α,6β,7β))-1-(4-(4-fluorophenyl)-4-oxobutyl)hexahydro-5,6-dihydroxy-4,7-bis(phenylmethyl)- 2H-1,3-diazepin-2-one (0.85 g, 1.73 mmol) in 20 mL absolute EtOH and 20 mL pyridine was treated with hydroxylamine hydrochloride (0.24 g, 3.46 mmol), stirred at room temperature for 1 h, and refluxed for 3 h. The reaction mixture was concentrated in vacuo, and the residue was triturated with cold water. The resulting white solid was collected by filtration, washed with water, and dried in vacuo to give the titled cyclic urea as a pyridine solvate. The solid was partitioned between 50 mL EtOAc and 25 mL saturated aqueous NaHCO$_3$ solution. The organic layer was washed with brine, dried over MgSO$_4$, filtered, and concentrated to a glass which was recrystallized from EtOAc-hexanes to give 0.69 g (70% yield) of the titled oxime. m.p. 148° C.(dec.); $^1$H NMR (300 MHz, DMSO-d$_6$ TMS) δ1.4 (m, 2H, CH$_2$), 2.0 (m, 1H), 2.6–2.9 (m, 2H), 3.0 (m, 3H), 3.25 (m, 1H), 3.4 (m, 2H), 3.70–3.73 (2m, 2H), 5.12 (s, 1H, OH), 5.21 (s, 1H, OH), 6.02 (s, 1H, NH), (7.05–7.35 (m, 12H), 7.56 (m, 2H, Ar)), 10.62 (s, 0.11 H), 11.15 (s, 0.89 H), mixture of syn and anti NOH); $^{19}$F NMR (282 MHz, DMSO-d$_6$) δ–113.936; IR (nujol) 3290 (OH) cm$^{-1}$, no ketone C=O; MS(NH$_3$-CI) m/e 506(M+1); $[α]_D^{20}$+122.55° (c=0.204, MeOH); Analysis calc'd for C$_{29}$H$_{32}$FN$_3$O$_4$ MW 505.59: C, 68.89; H, 6.38; N, 8.31; found: C, 68.81; H, 6.42; N, 8.20.

Utility

The N,N'-disubstituted cyclic urea compounds of Formula (I), prepared according to the methods of this invention, have been disclosed to be selective inhibitors of HIV protease, and as such, may be useful in the treatment of acquired immunodeficiency syndrome (AIDS). See, e.g., PCT Patent Application Publication No. WO 93/07128. The N,N'-disubstituted cyclic urea compounds of Formula (I), prepared according to the methods of this invention, are also useful as standards and reagents in determining the ability of a potential pharmaceutical to inhibit viral replication and/or human immunodeficiency virus protease. These compounds in the form of standards and reagents would be provided as a commercial kit comprising a compound of Formula (I) made by the methods of this invention. The methods of this invention also provide for the preparation of precursors to the compounds of Formula (I).

We claim:

1. A method for preparing a cyclic urea compound of Formula (Id) comprising the steps:

(a) converting a compound of Formula (IIa) to a compound of Formula (IIb) by any of direct alkylation, reductive amination, or successive acylation and reduction, (b) converting the compound of Formula (IIb) from step (a) to a product comprising a cyclic urea compound of Formula (Ib), (c) purifying the product of step (b) by
   (i) washing the product of step (b) with an aqueous acid solution, resulting in a washed product, and
   (ii) eluting the washed product of step (c)(i) through a bed of silica gel to produce a substantially pure compound of Formula (Ib), (d) converting the substantially pure compound of Formula (Ib) from step (c)(ii) to a cyclic urea compound of Formula (Ic), and (e) converting the compound of Formula (Ic) from step (d) to a cyclic urea compound of Formula (Id), wherein, the compound of Formula (IIa) has the structure shown in Formula (II) with the proviso that R$^{22}$ and R$^{23}$ are hydrogen, the compound of Formula (IIb) has the structure shown in Formula (II) with the proviso that only one of R$^{22}$ or R$^{23}$ is hydrogen, the compound of Formula (Ib) has the structure shown in Formula (I) with the proviso that only one of R$^{22}$ or R$^{23}$ is hydrogen, the compound of Formula (Ic) has the structure shown in Formula (I) with the proviso that neither $R^{22}$ nor $R^{23}$ is hydrogen, the compound of Formula (Id) has the structure shown in Formula (I) with the provisos that neither $R^{22}$ nor $R^{23}$ is hydrogen and none of the hydroxyl, sulfhydryl or amine groups which may be present in the compound of Formula (Id) are protected by a hydroxyl, sulhydryl or amine protecting group, compound (I) has a Formula:

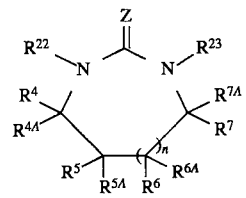

(I)

including a pharmaceutically acceptable salt or prodrug form thereof, and compound (II) has a Formula:

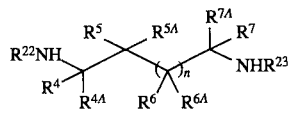

(II)

wherein, for each compound of Formula (I) and Formula (II):

each of $R^4$ and $R^7$ is independently:

hydrogen, $-O(R^{13})$, $-S(R^{13})$, $-C(=O)O(R^{13})$, $C_1-C_8$ alkyl substituted with 0–3 $R^{11}$, $C_2-C_8$ alkenyl substituted with 0–3 $R^{11}$, $C_2-C_8$ alkynyl substituted with 0–3 $R^{11}$, a $C_3-C_{14}$ carbocyclic ring system substituted with 0–3 $R^{11}$ or 0–3 $R^{12}$ or a 5- to 10-membered heterocyclic ring system containing 1 to 4 heteroatoms independently selected from oxygen, nitrogen or sulfur, the heterocyclic ring system being substituted with 0–2 $R^{12}$;

each of $R^{4A}$ and $R^{7A}$ is independently:

hydrogen, $-O(R^{13})$, $-S(R^{13})$, $-C(=O)O(R^{13})$, $C_1-C_4$ alkyl unsubstituted or substituted with halogen or $C_1-C_2$ alkoxy, or phenylmethyl unsubstituted or substituted with halogen or $C_1-C_2$ alkoxy;

$R^4$ and $R^{4A}$ can alternatively join to form a 5- to 7-membered carbocyclic ring substituted with 0–2 $R^{12}$;

$R^7$ and $R^{7A}$ can alternatively join to form a 5- to 7-membered carbocyclic ring substituted with 0–2 $R^{12}$;

each of $R^5$ and $R^{5A}$ is independently:

hydrogen, halogen, $-N(R^{20})_2$, $-S(R^{20})$, $-O(R^{20})$ or $C_1-C_6$ alkyl substituted with 0–3 $R^{11}$;

$R^5$ and $R^{5A}$ can alternatively join together to form a =O, =S or a ketal ring;

each of $R^6$ and $R^{6A}$ is independently:

hydrogen, halogen, $-N(R^{20})_2$, $-S(R^{20})$, $-O(R^{21})$ or $C_1-C_6$ alkyl substituted with 0–3 $R^{11}$;

$R^6$ and $R^{6A}$ can alternatively join together to form a =O, =S or a ketal ring;

$R^5$ and $R^6$ can alternatively join together to form an epoxide or aziridine ring; $-OCH_2SCH_2O-$, $-OS(=O)O-$, $-OC(=O)O-$, $-OCH_2O-$, $-OC(=S)O-$, $-OC(=O)C(=O)O-$, $-OC(CH_3)_2O-$, $-OC((CH_2)_3NH_2)(CH_3)O-$, $-OC(OCH_3)(CH_2CH_2CH_3)O-$, $-OS(=O)_2O-$, $-NHC(=O)NH-$, $-OC(=O)NH-$,
$-NHC(=O)O-$, $-NHCH_2O-$, $-OCH_2NH-$,
$-NHC(=S)O-$, $-OC(=S)NH-$,
$-OS(=O)NH-$, $-NHS(=O)O-$,
$-NHC(=O)C(=O)O-$, $-OC(=O)C(=O)NH-$,
$-NHC(=O)C(=O)NH-$, $-NHC(CH_3)_2O-$,
$-OC(CH_3)_2NH-$ or any group that, when administered to a mammalian subject as part of a compound of Formula (I), cleaves to form a compound having two free hydroxyl groups, or two free amino groups, or one free hydroxyl group and one free amino group;

each $R^{11}$ is independently:

hydrogen, keto, halogen, cyano, phenylmethyl, phenethyl, methylenedioxy, ethylenedioxy, hydroxamic acid, hydrazide, boronic acid, sulfonamide, azido, formyl, phenoxy, phenylmethoxy, nitro, $-CH_2^N(R^{13})(R^{14})$, $-N(R^{13})(R^{14})$, $-OCH_2C(=O)OH$, $-C(=O)O(R^{13})$, $-OC(=O)(R^{13})$, $-O(R^{13})$, $C_2-C_6$ alkoxyalkyl, $-S(=O)_m(R^{13})$, $-NHC(=NH)NH(R^{13})$, $-C(=NH)NH(R^{13})$, $-C(=O)N(R^{13})(R^{14})$, $-N(R^{14})C(=O)(R^{13})$, $=N-O(R^{14})$, $-N(R^{14})C(=O)O(R^{14})$, $-OC(=O)N(R^{13})(R^{14})$, $-N(R^{13})C(=O)N(R^{13})(R^{14})$, $-C(R^{14})=N-O(R^{14})$, $-N(R^{14})S(=O)_2N(R^{13})(R^{14})$,
$-N(R^{14})S(=O)_2(R^{13})$, $-S(=O)_2N(R^{13})(R^{14})$, $C_1-C_4$ alkyl, $C_2-C_4$ alkenyl, $C_3-C_{10}$ cycloalkyl, $C_3-C_6$ cycloalkylmethylene, $C_7-C_{10}$ arylalkyl, $C_3-C_6$ cycloalkoxy, $C_1-C_4$ alkyl substituted with $-N(R^{13})(R^{14})$, $C_1-C_4$ hydroxyalkyl, $C_1-C_4$ haloalkyl, $C_1-C_4$ haloalkoxy, $C_1-C_4$ alkoxycarbonyl, $C_1-C_4$ alkylcarbonyloxy, $C_1-C_4$ alkylcarbonyl, $C_1-C_4$ alkylcarbonylamino, 2-(1-morpholino)ethoxy, $-(C_1-C_3$ alkyl)aryl substituted with 0–2 $R^{12}$, a $C_5-C_{14}$ carbocyclic residue substituted with 0–3 $R^{12}$ or a 5- to 10-membered heterocyclic ring system containing 1 to 4 heteroatoms independently selected from oxygen, nitrogen or sulfur, the heterocyclic ring system being substituted with 0–3 $R^{12}$; and 1–3 amino acids linked together via amide bonds, and linked to $R^4$, $R^7$, $R^{20}$, or $R^{21}$ via the amine or carboxylate terminus;

m is: 0, 1 or 2;

each $R^{11A}$ is independently:

H, keto, halogen, cyano, $-CH_2NH_2$, $-NH_2$, $-C(=O)OH$, $-OC(=O)(C_1-C_3$ alkyl), $-OH$, $C_2-C_6$ alkoxyalkyl, $-C(=O)NH_2$, $-OC(=O)NH_2$, $-NHC(=O)NH_2$, $-S(=O)_2NH_2$, $C_1-C_4$ alkyl, $C_2-C_4$ alkenyl, $C_3-C_{10}$ cycloalkyl, $C_3-C_6$ cycloalkylmethylene, benzyl, phenethyl, phenoxy, benzyloxy, nitro, $C_7-C_{10}$ arylalkyl, hydroxamic acid, hydrazide, boronic acid, $C_3-C_6$ cycloalkoxy, $C_1-C_4$ alkyl substituted with $-NH_2$, $C_1-C_4$ hydroxyalkyl, methylenedioxy, ethylenedioxy, $C_1-C_4$ haloalkyl, $C_1-C_4$ haloalkoxy, $C_1-C_4$ alkoxycarbonyl, $C_1-C_4$ alkylcarbonyloxy, $C_1-C_4$ alkylcarbonyl, $C_1-C_4$ alkylcarbonylamino, $-OCH_2C(=O)OH$, 2-(1-morpholino) ethoxy, azido, aryl ($C_1-C_3$ alkyl), a $C_5-C_{14}$ carbocyclic residue, or a 5- to 10-membered heterocyclic ring system containing 1 to 4 heteroatoms independently selected from oxygen, nitrogen or sulfur;

each $R^{12}$, when a substituent on carbon, is independently:

phenyl, phenylmethyl, phenethyl, phenoxy, phenylmethoxy, halogen, hydroxy, nitro, cyano, $C_1-C_4$ alkyl, $C_3-C_6$ cycloalkyl, $C_3-C_6$ cycloalkylmethylene, $C_7-C_{10}$ arylalkyl, $C_1-C_4$ alkoxy, $-C(=O)OH$, hydroxamic acid, hydrazide, boronic acid, sulfonamide, formyl, $C_3$–$C_6$ cycloalkoxy, —O($R^{13}$), $C_1$–$C_4$ alkyl substituted with —N($R^{13}$)($R^{14}$), —N($R^{13}$)($R^{14}$), $C_2$–$C_6$ alkoxyalkyl, $C_1$–$C_4$ hydroxyalkyl, methylenedioxy, ethylenedioxy, $C_1$–$C_4$ haloalkyl, $C_1$–$C_4$haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —S(=O)$_m$($R^{13}$), —S(=O)$_2$N($R^{13}$)($R^{14}$), —NHS(=O)$_2$ ($R^{14}$), —OCH$_2$C(=O)OH, 2-(1-morpholino) ethoxy, —C($R^{14}$)=N—O($R^{14}$), a 5- to 10-membered heterocyclic ring containing from 1 to 4 heteroatoms independently selected from oxygen, nitrogen or sulfur, the heterocyclic ring system being substituted with 0–3 $R^{15}$, a 3- or 4-carbon aliphatic chain attached to an adjacent carbon on the ring to which it is appended to form a fused 5- or 6-membered ring, the 5- or 6-membered ring being optionally substituted on any of the aliphatic carbons with halogen, $C_1$–$C_4$ alkyl, $C_1$–$C_4$ alkoxy, hydroxy, —N($R^{13}$)($R^{14}$), or when $R^{12}$ is a substituent on a saturated carbon atom, $R^{12}$ may alternatively be =O or =S;

each $R^{12}$, when a substituent on nitrogen, is independently:
phenyl, phenylmethyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethylene, —CH$_2$N($R^{13}$)($R^{14}$), —N($R^{13}$)($R^{14}$), $C_2$–$C_6$ alkoxyalkyl, $C_1$–$C_4$ haloalkyl, $C_1$–$C_4$alkoxycarbonyl, —C(=O)OH, $C_1$–$C_4$ alkylcarbonyloxy, $C_1$–$C_4$ alkylcarbonyl or —C($R^{14}$)=N—O($R^{14}$);

each $R^{13}$ is independently:
hydrogen,
phenyl substituted with 0–3 $R^{11A}$,
phenylmethyl substituted with 0–3 $R^{11A}$,
$C_1$–$C_6$ alkyl substituted with 0–3 $R^{11A}$,
$C_2$–$C_4$ alkenyl substituted with 0–3 $R^{11A}$,
$C_1$–$C_6$ alkylcarbonyl substituted with 0–3 $R^{11A}$,
$C_1$–$C_6$ alkoxycarbonyl substituted with 0–3 $R^{11A}$,
$C_1$–$C_6$ alkylaminocarbonyl substituted with 0–3 $R^{11A}$,
$C_3$–$C_6$ alkoxyalkyl substituted with 0–3 $R^{11A}$,
an amine protecting group when $R^{13}$ is bonded to N, or
a hydroxy protecting group when $R^{13}$ is bonded to O;

each $R^{14}$ is independently:
hydrogen, hydroxy, trifluoromethyl, $C_1$–$C_6$ alkoxy, $C_2$–$C_6$ alkenyl, phenylmethyl, amino,
$C_1$–$C_6$ alkyl substituted with 0–3 groups selected from hydroxy, $C_1$–$C_4$ alkoxy, halogen or amino,
an amine protecting group when $R^{14}$ is bonded to N, or
a hydroxy protecting group when $R^{14}$ is bonded to O;

$R^{13}$ and $R^{14}$ can alternatively join to form: —(CH$_2$)$_4$—, —(CH$_2$)$_5$—, —CH$_2$CH$_2$N($R^{15}$)CH$_2$CH$_2$— or —CH$_2$CH$_2$OCH$_2$CH$_2$—;

$R^{15}$ is: hydrogen or methyl;

each of $R^{20}$ and $R^{21}$ is independently:
hydrogen,
$C_1$–$C_6$ alkyl substituted with 0–3 $R^{11}$,
$C_3$–$C_6$ alkoxyalkyl substituted with 0–3 $R^{11}$,
$C_1$–$C_6$ alkylcarbonyl substituted with 0–3 $R^{11}$,
$C_1$–$C_6$ alkoxycarbonyl substituted with 0–3 $R^{11}$,
$C_1$–$C_6$ alkylaminocarbonyl substituted with 0–3 $R^{11}$
benzoyl substituted with 0–3 $R^{12}$,
phenoxycarbonyl substituted with 0–3 $R^{12}$,
phenylaminocarbonyl substituted with 0–3 $R^{12}$, or any group that, when administered to a mammalian subject as part of a compound of Formula (I), cleaves to form a free hydroxyl, free amino or free sulfhydryl;

each of $R^{22}$ and $R^{23}$ is independently:
hydrogen,
$C_1$–$C_8$ alkyl substituted with 0–3 $R^{31}$,
$C_2$–$C_8$ alkenyl substituted with 0–3 $R^{31}$,
$C_2$–$C_8$ alkynyl substituted with 0–3 $R^{31}$,
a $C_3$–$C_{14}$ carbocyclic ring system substituted with 0 5 $R^{31}$ or 0–5 $R^{32}$ or
a 5- to 10-membered heterocyclic ring system containing 1 to 4 heteroatoms independently selected from oxygen, nitrogen or sulfur, the heterocyclic ring system being substituted with 0–2 $R^{32}$;

alternatively, $R^{22}$ can join with $R^4$ or $R^{4A}$ to form a 5- or 6-membered fused heterocyclic ring or carbocyclic ring substituted with 0–2 $R^{12}$ the heterocyclic ring containing 1–3 heteroatoms independently selected from nitrogen, sulfur or oxygen;

alternatively, $R^{23}$ can join with $R^7$ or $R^{7A}$ to form a 5- or 6-membered fused heterocyclic ring or carbocyclic ring substituted with 0–2 $R^{12}$ the heterocyclic ring containing 1–3 heteroatoms independently selected from nitrogen, sulfur or oxygen;

alternatively, $R^{22}$ or $R^{23}$ can join with $R^5$ or $R^6$ to form a 0- to 7- membered bridge to form a carbocyclic or heterocyclic ring, said bridge being substituted with 0–2 $R^{12}$ and the bridge containing 0–3 heteroatoms independently selected from nitrogen, sulfur or oxygen;

alternatively, the atoms to which $R^{22}$ and $R^{4A}$ are appended may be joined together with a double bond;

alternatively, the atoms to which $R^{23}$ and $R^{7A}$ are appended may be joined together with a double bond;

Z is: O or S;

each $R^{31}$ is independently:
keto, halogen, cyano, —CH$_2$N($R^{13}$)($R^{14}$), —N($R^{13}$)($R^{14}$), —C(=O)O($R^{13}$), —C(=O)($R^{11}$), —OC(=O)($R^{13}$), —O($R^{13}$), $C_2$–$C_6$ alkoxyalkyl, —S(=O)$_m$($R^{13}$), —NHC(=NH)NH($R^{13}$), —C(=NH)NH($R^{13}$), —C(=O)N($R^{13}$)($R^{14}$), —N($R^{14}$)C(=O)($R^{13}$), =N—O($R^{14}$), —N($R^{14}$)C(=O)O($R^{14}$), —OC(=O)N($R^{13}$)($R^{14}$), —N($R^{13}$)C(=O)N($R^{13}$)($R^{14}$), —N($R^{14}$)S(=O)$_2$N($R^{13}$)($R^{14}$), —N($R^{14}$)S(=O)$_2$($R^{13}$), —S(=O)$_2$N($R^{13}$)($R^{14}$), $C_1$–$C_4$ alkyl, $C_2$–$C_4$ alkenyl, $C_3$–$C_{10}$ cycloalkyl, $C_3$–$C_6$ cycloalkylmethylene, phenylmethyl, phenethyl, phenoxy, phenylmethoxy, nitro, $C_7$–$C_{10}$ arylalkyl, hydroxamic acid, hydrazide, oxime, boronic acid, sulfonamide, formyl, $C_3$–$C_6$ cycloalkoxy, $C_1$–$C_4$ alkyl substituted with —N($R^{13}$)($R^{14}$), $C_1$–$C_4$ hydroxyalkyl, methylenedioxy, ethylenedioxy, $C_1$–$C_4$ haloalkyl, $C_1$–$C_4$haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —OCH$_2$C(=O)O($R^{13}$), 2-(1-morpholino)ethoxy, azido, —C($R^{14}$)=N— O($R^{14}$), a $C_5$–$C_{14}$ carbocyclic residue substituted with 0–5 $R^{32}$, a 5- to 10-membered heterocyclic ring system containing 1 to 4 heteroatoms independently selected from oxygen, nitrogen or sulfur, the heterocyclic ring system being substituted with 0–2 $R^{32}$, or 1–3 amino acids, linked together via amide bonds, and linked to $R^{22}$ or $R^{23}$ via the amine or carboxylate terminus;

each $R^{32}$, when a substituent on carbon, is independently:

phenethyl, phenoxy, $C_3$–$C_{10}$ cycloalkyl, $C_3$–$C_6$ cycloalkylmethylene, $C_7$–$C_{10}$ arylalkyl, hydrazide, oxime, $C_2$–$C_6$ alkoxyalkyl, methylenedioxy, ethylenedioxy, $C_1$–$C_4$ alkylcarbonyloxy, —NHS(=O)$_2$ ($R^{14}$), phenylmethoxy, halogen, 2-(1-morpholino)ethoxy, —C(=O)O($R^{13}$), hydroxamic acid, —C(=O)N($R^{13}$)N($R^{13}$)($R^{14}$), cyano, boronic acid, sulfonamide, formyl, $C_3$–$C_6$ cycloalkoxy, $C_1$–$C_4$ haloalkyl, $C_1$–$C_4$ haloalkoxy, $C_2$–$C_4$ haloalkenyl, $C_2$–$C_4$ haloalkynyl, —N($R^{13}$)($R^{14}$), —C($R^{14}$)=N—O($R^{14}$), —NO$_2$, —O($R^{13}$), —N($R^{40}$)($R^{41}$), —S(=O)$_m$($R^{13}$), —S(=O)$_m$N($R^{13}$)($R^{14}$), —C(=O)N($R^{13}$)($R^{14}$), —OC(=O)N($R^{13}$)($R^{14}$), —C(=O)($R^{11}$), —OC(=O)($R^{11}$), —OC(=O)O($R^{13}$), phenyl, —C(=O)N($R^{13}$)—($C_1$–$C_4$ alkyl)-N($R^{13}$)($R^{14}$), —C(=O)N($R^{40}$)($R^{41}$), —C(=O)N($R^{13}$)C($R^{11}$)$_2$N($R^{13}$)($R^{14}$), —C(=O)N($R^{13}$)C($R^{11}$)$_2$N($R^{13}$)NH($R^{14}$), —C(=O)N($R^{13}$)C($R^{11}$)$_2$N($R^{13}$)C(=O)O($R^{13}$), —C(=O)N($R^{13}$)—($C_1$–$C_4$ alkyl)-N($R^{13}$)C(=O)O($R^{13}$), —C(=O)N($R^{13}$)—($C_1$–$C_4$ alkyl)-$R^{11}$, —C(=O)C($R^{11}$)$_2$N($R^{13}$)($R^{14}$), —C(=O)C($R^{11}$)$_2$N($R^{13}$)NH($R^{14}$), —C(=O)C($R^{11}$)$_2$N($R^{13}$)C(=O)O($R^{13}$), —C(=O)—($C_1$–$C_4$ alkyl) —N($R^{13}$)($R^{14}$), —C(=O)—($C_1$–$C_4$ alkyl)—N($R^{13}$)C(=O)O($R^{13}$), $C_1$–$C_4$ alkoxy substituted with 0–4 groups selected from: $R^{11}$, $C_3$–$C_6$ cycloalkyl, —C(=O)O($R^{13}$), —C(=O)N($R^{13}$)($R^{14}$), —N($R^{13}$)($R^{14}$) or hydroxyl, $C_1$–$C_4$ alkyl substituted with 0–4 groups selected from: $R^{11}$, =N($R^{14}$), =NN($R^{13}$)C(=O)N($R^{13}$)($R^{14}$) or —N($R^{13}$)($R^{14}$), $C_2$–$C_4$ alkenyl substituted with 0–4 $R^{11}$, $C_2$–$C_4$ alkynyl substituted with 0–4 $R^{11}$, a 5- or 6-membered heterocyclic ring containing from 1 to 4 heteroatoms independently selected from oxygen, nitrogen or sulfur, a 3- or 4-carbon aliphatic chain attached to an adjacent carbon on the ring to which it is appended, to form a fused 5- or 6-membered ring, the 5- or 6-membered ring being optionally substituted on the aliphatic carbons with halogen, $C_1$–$C_4$ alkyl, $C_1$–$C_4$ alkoxy, hydroxyl—N($R^{13}$)($R^{14}$), or when $R^{32}$ is attached to a saturated carbon atom, $R^{32}$ may be =O or =S;

each $R^{32}$, when a substituent on nitrogen, is independently:
phenyl, phenylmethyl, phenethyl, hydroxyl, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethylene, —CH$_2$N($R^{13}$)($R^{14}$), —N($R^{13}$)($R^{14}$), $C_2$–$C_6$ alkoxyalkyl, $C_1$–$C_4$ haloalkyl, $C_1$–$C_4$ alkoxycarbonyl, —C(=O)OH, $C_1$–$C_4$ alkylcarbonyloxy, $C_1$–$C_4$ alkylcarbonyl or —C($R^{14}$)=N—O($R^{14}$);

$R^{40}$ is: hydrogen or $C_1$–$C_3$ alkyl;

$R^{41}$ is: —C(=O)N($R^{13}$)($R^{14}$), —C(=O)N($R^{13}$)NH($R^{14}$), —C(=O)C($R^{11}$)$_2$N($R^{13}$)($R^{14}$), —C(=O)C($R^{11}$)$_2$N($R^{13}$)NH($R^{14}$), —C(=O)C($R^{11}$)$_2$N($R^{13}$)C(=O)O($R^{13}$), —C(=O) H, —C(=O)($R^{11}$), —C(=O)—($C_1$–$C_4$ alkyl)—N($R^{13}$)($R^{14}$), —C(=O)—($C_1$–$C_4$ alkyl)—N($R^{13}$)C(=O)O($R^{13}$) or 1–3 amino acids linked together via amide bonds and linked to the N atom via the carboxylate terminus; and n is: 0, 1 or 2;

provided that:

$R^4$ $R^{4A}$ $R^7$ and $R^{7A}$ are not all hydrogen;

when $R^4$ and $R^{4A}$ are both hydrogen, $R^{22}$ is not hydrogen, and when $R^7$ and $R^{7A}$ are both hydrogen, $R^{23}$ is not hydrogen.

2. The method according to claim 1, wherein the direct alkylation of step (a) comprises treating a compound of Formula (IIa) with a base and an alkylating agent, where the alkylating agent has the Formula $R^{16}X^1$, wherein $R^{16}$ is:

$C_1$–$C_8$ alkyl substituted with 0–3 $R^{31}$, $C_2$–$C_8$ alkenyl substituted with 0–3 $R^{31}$, $C_2$–$C_8$ alkynyl substituted with 0–3 $R^{31}$, a $C_3$–$C_{14}$ carbocyclic ring system substituted with 0–5 $R^{31}$ or 0–5 $R^{32}$ or a 5- to 10-membered heterocyclic ring system containing 1 to 4 heteroatoms independently selected from oxygen, nitrogen or sulfur, the heterocyclic ring system being substituted with 0–2 $R^{32}$; and $X^1$ is a leaving group susceptible to displacement with an amino nitrogen.

3. The method according to claim 2, wherein the leaving group is halide, tosylate, mesylate or acetate.

4. The method according to claim 2, wherein the compound of Formula (IIa) and the alkylating agent of Formula $R^{16}X^1$ are contacted in a molar ratio of between about 1:0.9 and about 1:1.5

5. The method according to claim 2, wherein the base is potassium carbonate, sodium carbonate, lithium carbonate, cesium carbonate, potassium bicarbonate or sodium bicarbonate.

6. The method according to claim 2, wherein the direct alkylation is conducted in the presence of a phase transfer agent.

7. The method according to claim 6, wherein the phase transfer agent is tetrabutylammonium iodide and potassium iodide.

8. The method according to claim 2, wherein the direct alkylation is conducted in a solvent selected from the group consisting of acetonitrile and tetrahydrofuran, and wherein the compound of Formula (IIa) is present in the solvent at a concentration of about 0.03 molar to about 3.0 molar, and wherein the base is potassium carbonate, and wherein about two equivalents of base are present for each equivalent of the compound of Formula (IIa).

9. The method according to claim 1, wherein the reductive amination of step (a) comprises reacting a compound of Formula (IIa) with a carbonyl compound to form an intermediate oxime, and reacting the intermediate oxime with a reducing agent to form a compound of Formula (IIb), wherein the carbonyl compound is $C_1$–$C_8$ alkane substituted with 0–3 $R^{31}$, $C_2$–$C_8$ alkene substituted with 0–3 $R^{31}$, $C_2$–$C_8$ alkyne substituted with 0–3 $R^{31}$, a $C_3$–$C_{14}$ carbocyclic ring substituted with 0–5 $R^{31}$ or 0–5 $R^{32}$ and a 5- to 10-membered heterocyclic ring containing 1 to 4 heteroatoms independently selected from oxygen, nitrogen or sulfur, the heterocyclic ring being substituted with 0–2 $R^{32}$, with the proviso that at least one methylene group (—CH$_2$—) is replaced with a carbonyl group (—C(=O)—).

10. The method according to claim 9, wherein the reducing agent is NaBH$_4$, lithium aluminum hydride (LiAlH$_4$), sodium cyanoborohydride (NaBH$_3$CN), borane complexes including BH$_3$.THF, BH$_3$.SMe$_2$, BH$_3$.amine including pyridine, and other borane compounds including $BH(OAc)_3$, $BH(O_2CCF3)_2$, $NaBH(OAc)_3$, $(t\text{-butyl})NH_2BH_3$, $LiBH(Et)_3$, $LiBH(t\text{-butyl})_3$, $NaAlH_2(O(CH_2)_2OCH_3)$, $LiBH(sec\text{-butyl})_3$ or $Zn(BH_3CN)_2$.

11. The method according to claim 9, wherein the molar ratio of the carbonyl compound to the compound of Formula (IIa) is about 1:1.

12. The method according to claim 1, wherein the successive acylation and reduction of step (a) comprises reacting a compound of Formula (IIa) with an acylating agent of Formula $R^{17}$ $(C=O)X^2$ to form an amide compound, and the amide compound is reacted with a reducing agent to form a compound of Formula (IIb), wherein $R^{17}$ is:

$C_1$–$C_7$ alkyl substituted with 0–3 $R^{31}$, $C_2$–$C_7$ alkenyl substituted with 0–3 $R^{31}$, $C_2$ $C_7$ alkynyl substituted with 0–3 $R^{31}$, or —$R^{31}$; and $X^2$ is a leaving group.

13. The method according to claim 12 wherein the leaving group $X^2$ is halide, —$OR^{17}$ or —$OC(=O)R^{17}$.

14. The method according to claim 12 wherein the molar ratio of the acylating agent to the compound of Formula (IIa) is about 1:1.

15. The method according to claim 12, wherein the reducing agent is lithium aluminum hydride ($LiAlH_4$), $BH_3.THF$, $BH_3.SMe_2$, $B_2H_6$, $NaBH_4$ and $MeSO_3^H$ in DMSO, $(Bu)_4NBH_4$ in methylene chloride, $NaBH_4$—$TiCl_4$ in dimethoxyethane, $NiCl_2$ in methanol, heterogeneous catalytic hydrogenation with Cu chromite, Ba/Cu chromite, Raney nickel, Raney cobalt, or rhenium on carbon.

16. The method according to claim 1, wherein step (b) comprises reacting a compound of Formula (IIb) with either carbonyl diimidazole, thereby forming a cyclic urea of Formula (Ib) having Z=O, or thiocarbonyl diimidazole, thereby forming a cyclic urea of Formula (Ib) having Z=S.

17. The method according to claim 1, wherein the aqueous acid solution of step (c)(i) is an aqueous hydrochloric acid, nitric acid, phosphoric acid or citric acid solution.

18. The method according to claim 1, wherein the aqueous acid solution of step (c)(i) is an aqueous citric acid solution.

19. The method according to claim 1, wherein step (d) comprises treating the product of step (c)(ii) with an alkylating agent of Formula $R^{16}X^1$ in the presence of a base, wherein $R^{16}$ is:

$C_1$–$C_8$ alkyl substituted with 0–3 $R^{31}$, $C_2$–$C_8$ alkenyl substituted with 0–3 $R^{31}$, $C_2$–$C_8$ alkynyl substituted with 0–3 $R^{31}$, a $C_3$–$C_{14}$ carbocyclic ring system substituted with 0–5 $R^{31}$ or 0–5 $R^{32}$ or a 5- to 10-membered heterocyclic ring system containing 1 to 4 heteroatoms independently selected from oxygen, nitrogen or sulfur, the heterocyclic ring system being substituted with 0–2 $R^{32}$; and $X^1$ is a leaving group.

20. The method according to claim 19, wherein the leaving group $X^1$ is halide, mesylate, tosylate or acetate.

21. The method according to claim 19, wherein the base is sodium hydride.

22. The method according to claim 19, wherein the molar ratio of the product of step (c)(ii) to the alkylating agent is about 1:1.

23. The method according to claim 1, wherein step (e) comprises subjecting the cyclic urea compound of Formula (Ic) as produced in step (d) to an acidic or basic condition, so as to remove at least one protecting group if such a protecting group is present.

24. The method according to claim 23, wherein the acidic condition comprises subjecting the product of step (d) to aqueous hydrochloric acid.

25. A method for preparing a cyclic urea compound of Formula (Ic) comprising the steps:

(a) converting a compound of Formula (IIa) to a compound of Formula (IIb) by any of direct alkylation, reductive amination, or successive acylation and reduction, (b) converting the compound of Formula (IIb) from step (a) to a product comprising a cyclic urea compound of Formula (Ib), (c) purifying the product of step (b) by
 (i) washing the product of step (b) with an aqueous acid solution, resulting in a washed product, and
 (ii) eluting the washed product of step (c)(i) through a bed of silica gel to produce a substantially pure compound of Formula (Ib), and (d) converting the substantially pure compound of Formula (Ib) from step (c)(ii) to a cyclic urea compound of Formula (Ic), wherein, the compound of Formula (IIa) has the structure shown in Formula (II) with the proviso that $R^{22}$ and $R^{23}$ are hydrogen, the compound of Formula (IIb) has the structure shown in Formula (II) with the proviso that only one of $R^{22}$ or $R^{23}$ is hydrogen, the compound of Formula (Ib) has the structure shown in Formula (I) with the proviso that only one of $R^{22}$ or $R^{23}$ is hydrogen, the compound of Formula (Ic) has the structure shown in Formula (I) with the proviso that neither $R^{22}$ nor $R^{23}$ is hydrogen;

compound (I) has a Formula:

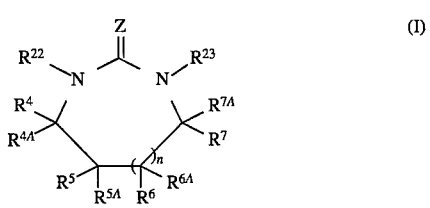

including a pharmaceutically acceptable salt or prodrug form thereof, and compound (II) has a Formula:

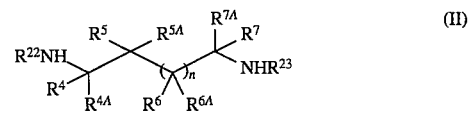

wherein, for each compound of Formula (I) and Formula (II):

each of $R^4$ and $R^7$ is independently:

hydrogen, —$O(R^{13})$, —$S(R^{13})$, —$C(=O)O(R^{13})$, $C_1$–$C_8$ alkyl substituted with 0–3 $R^{11}$, $C_2$–$C_8$ alkenyl substituted with 0–3 $R^{11}$, $C_2$–$C_8$ alkynyl substituted with 0–3 $R^{11}$, a $C_3$–$C_{14}$ carbocyclic ring system substituted with 0–3 $R^{11}$ or 0–3 $R^{12}$, or a 5- to 10-membered heterocyclic ring system containing 1 to 4 heteroatoms independently selected from oxygen, nitrogen or sulfur, the heterocyclic ring system being substituted with 0–2 $R^{12}$;

each of $R^{4A}$ and $R^{7A}$ is independently:

hydrogen, —O($R^{13}$), —S($R^{13}$), —C(=O)O($R^{13}$),
$C_1$–$C_4$ alkyl unsubstituted or substituted with halogen or $C_1$–$C_2$ alkoxy, or
phenylmethyl unsubstituted or substituted with halogen or $C_1$–$C_2$ alkoxy;

$R^4$ and $R^{4A}$ can alternatively join to form a 5- to 7-membered carbocyclic ring substituted with 0–2 $R^{12}$;

$R^7$ and $R^{7A}$ can alternatively join to form a 5- to 7-membered carbocyclic ring substituted with 0–2 $R^{12}$;

each of $R^5$ and $R^{5A}$ is independently:
hydrogen, halogen, —N($R^{20}$)$_2$, —S($R^{20}$), —O($R^{20}$) or $C_1$–$C_6$ alkyl substituted with 0–3 $R^{11}$;

$R^5$ and $R^{5A}$ can alternatively join together to form a =O, =S or a ketal ring;

each of $R^6$ and $R^{6A}$ is independently:
hydrogen, halogen, —N($R^{20}$)$_2$, —S($R^{20}$), —O($R^{21}$) or $C_1$–$C_6$ alkyl substituted with 0–3 $R^{11}$;

$R^6$ and $R^{6A}$ can alternatively join together to form a =O, =S or a ketal ring;

$R^5$ and $R^6$ can alternatively join together to form an epoxide or aziridine ring; —OCH$_2$SCH$_2$O—, —OS(=O)O—, —OC(=O)O—, —OCH$_2$O—, —OC(=S)O—, —OC(=O)C(=O)O—, —OC(CH$_3$)$_2$O—, —OC((CH$_2$)$_3$NH$_2$)(CH$_3$)O—, —OC(OCH$_3$)(CH$_2$CH$_2$CH$_3$)O—, —OS(=O)$_2$O—, —NHC(=O)NH—, —OC(=O)NH—, —NHC(=O)O—, —NHCH$_2$O—, —OCH$_2$NH—, —NHC(=S)O—, —OC(=S)NH—, —OS(=O)NH—, —NHS(=O)O—, —NHC(=O)C(=O)O—, —OC(=O)C(=O)NH—, —NHC(=O)C(=O)NH—, —NHC(CH$_3$)$_2$O—, —OC(CH$_3$)$_2$NH— or any group that, when administered to a mammalian subject as part of a compound of Formula (I), cleaves to form a compound having two free hydroxyl groups, or two free amino groups, or one free hydroxyl group and one free amino group;

each $R^{11}$ is independently:
hydrogen, keto, halogen, cyano, phenylmethyl, phenethyl, methylenedioxy, ethylenedioxy, hydroxamic acid, hydrazide, boronic acid, sulfonamide, azido, formyl, phenoxy, phenylmethoxy, nitro, —CH$_2$N($R^{13}$)($R^{14}$), —N($R^{13}$)($R^{14}$), —OCH$_2$C(=O)OH, —C(=O)O($R^{13}$), —OC(=O)($R^{13}$), —O($R^{13}$), $C_2$–$C_6$ alkoxyalkyl, —S(=O)$_m$($R^{13}$), —NHC(=NH)NH($R^{13}$), —C(=NH)NH($R^{13}$), —C(=O)N($R^{13}$)($R^{14}$), —N($R^{14}$)C(=O)($R^{13}$), =N—O($R^{14}$), —N($R^{14}$)C(=O)O($R^{14}$), —OC(=O)N($R^{13}$)($R^{14}$), —N($R^{13}$)C(=O)N($R^{13}$)($R^{14}$), —C($R^{14}$)=N—O($R^{14}$), —N($R^{14}$)S(=O)$_2$N($R^{13}$)($R^{14}$), —N($R^{14}$)S(=O)$_2$($R^{13}$), —S(=O)$_2$N($R^{13}$)($R^{14}$), $C_1$–$C_4$ alkyl, $C_2$–$C_4$ alkenyl, $C_3$–$C_{10}$ cycloalkyl, $C_3$–$C_6$ cycloalkylmethylene, $C_7$–$C_{10}$ arylalkyl, $C_3$–$C_6$ cycloalkoxy, $C_1$–$C_4$ alkyl substituted with —N($R^{13}$)($R^{14}$), $C_{1-4}$ hydroxyalkyl, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, 2-(1-morpholino)ethoxy, -($C_1$–$C_3$ alkyl)aryl substituted with 0–2 $R^{12}$, a $C_5$–$C_{14}$ carbocyclic residue substituted with 0–3 $R^{12}$, or
a 5- to 10-membered heterocyclic ring system containing 1 to 4 heteroatoms independently selected from oxygen, nitrogen or sulfur, the heterocyclic ring system being substituted with 0–3 $R^{12}$; and 1–3 amino acids linked together via amide bonds, and linked to $R^4$, $R^7$, $R^{20}$, or $R^{21}$ via the amine or carboxylate terminus;

m is: 0, 1 or 2;

each $R^{11A}$ is independently:
H, keto, halogen, cyano, —CH$_2$NH$_2$, —NH$_2$, —C(=O)OH, —OC(=O)($C_1$–$C_3$ alkyl), —OH, $C_2$–$C_6$ alkoxyalkyl, —C(=O)NH$_2$, —OC(=O)NH$_2$, —NHC(=O)NH$_2$, —S(=O)$_2$NH$_2$, $C_1$–$C_4$ alkyl, $C_2$–$C_4$ alkenyl, $C_3$–$C_{10}$ cycloalkyl, $C_3$–$C_6$ cycloalkylmethylene, benzyl, phenethyl, phenoxy, benzyloxy, nitro, $C_7$–$C_{10}$ arylalkyl, hydroxamic acid, hydrazide, boronic acid, $C_3$–$C_6$ cycloalkoxy, $C_1$–$C_4$ alkyl substituted with —NH$_2$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —OCH$_2$C(=O)OH, 2-(1-morpholino)ethoxy, azido, aryl($C_1$–$C_3$ alkyl), a $C_5$–$C_{14}$ carbocyclic residue, or a 5- to 10-membered heterocyclic ring system containing 1 to 4 heteroatoms independently selected from oxygen, nitrogen or sulfur;

each $R^{12}$ when a substituent on carbon, is independently:
phenyl, phenylmethyl, phenethyl, phenoxy, phenylmethoxy, halogen, hydroxy, nitro, cyano, $C_1$–$C_4$ alkyl, $C_3$–$C_6$ cycloalkyl, $C_3$–$C_6$ cycloalkylmethylene, $C_7$–$C_{10}$ arylalkyl, $C_1$–$C_4$ alkoxy, —C(=O)OH, hydroxamic acid, hydrazide, boronic acid, sulfonamide, formyl, $C_3$–$C_6$ cycloalkoxy, —O($R^{13}$), $C_1$–$C_4$ alkyl substituted with —N($R^{13}$)($R^{14}$), —N($R^{13}$)($R^{14}$), $C_2$–$C_6$ alkoxyalkyl, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —S(=O)$_m$($R^{13}$), —S(=O)$_2$N($R^{13}$)($R^{14}$), —NHS(=O)$_2$($R^{14}$), —OCH$_2$C(=O)OH, 2-(1-morpholino)ethoxy, —C($R^{14}$)=N—O($R^{14}$), a 5- to 10-membered heterocyclic ring containing from 1 to 4 heteroatoms independently selected from oxygen, nitrogen or sulfur, the heterocyclic ring system being substituted with 0–3 $R^{15}$ a 3- or 4-carbon aliphatic chain attached to an adjacent carbon on the ring to which it is appended to form a fused 5- or 6-membered ring, the 5- or 6-membered ring being optionally substituted on any of the aliphatic carbons with halogen, $C_1$–$C_4$ alkyl, $C_1$–$C_4$ alkoxy, hydroxy, —N($R^{13}$)($R^{14}$), or when $R^{12}$ is a substituent on a saturated carbon atom, $R^{12}$ may alternatively be =O or =S;

each $R^{12}$ when a substituent on nitrogen, is independently:
phenyl, phenylmethyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethylene, —CH$_2$N($R^{13}$)($R^{14}$), —N($R^{13}$)($R^{14}$), $C_2$–$C_6$ alkoxyalkyl, $C_1$–$C_4$ haloalkyl, $C_1$–$C_4$ alkoxycarbonyl, —C(=O)OH, $C_1$–$C_4$ alkylcarbonyloxy, $C_1$–$C_4$ alkylcarbonyl or —C($R^{14}$)=N—O($R^{14}$);

each $R^{13}$ is independently:
hydrogen,
phenyl substituted with 0–3 $R^{11A}$,
phenylmethyl substituted with 0–3 $R^{11A}$,
$C_1$–$C_6$ alkyl substituted with 0–3 $R^{11A}$,
$C_2$–$C_4$ alkenyl substituted with 0–3 $R^{11A}$,
$C_1$–$C_6$ alkylcarbonyl substituted with 0–3 $R^{11A}$,
$C_1$–$C_6$ alkoxycarbonyl substituted with 0–3 $R^{11A}$,
$C_1$–$C_6$ alkylaminocarbonyl substituted with 0–3 $R^{11A}$,
$C_3$–$C_6$ alkoxyalkyl substituted with 0–3 $R^{11A}$, an amine protecting group when $R^{13}$ is bonded to N, or
a hydroxy protecting group when $R^{13}$ is bonded to O;

each $R^{14}$ is independently:
  hydrogen, hydroxy, trifluoromethyl, $C_1$–$C_6$ alkoxy, $C_2$–$C_6$ alkenyl, phenylmethyl, amino,
  $C_1$–$C_6$ alkyl substituted with 0–3 groups selected from hydroxy, $C_1$–$C_4$ alkoxy, halogen or amino,
  an amine protecting group when $R^{14}$ is bonded to N, or
  a hydroxy protecting group when $R^{14}$ is bonded to O;

$R^{13}$ and $R^{14}$ can alternatively join to form:
  —$(CH_2)_4$—, —$(CH_2)_5$—, —$CH_2CH_2N(R^{15})CH_2CH_2$— or —$CH_2CH_2OCH_2CH_2$—;

$R^{15}$ is: hydrogen or methyl;

each of $R^{20}$ and $R^{21}$ is independently:
  hydrogen,
  $C_1$–$C_6$ alkyl substituted with 0–3 $R^{11}$,
  $C_3$–$C_6$ alkoxyalkyl substituted with 0–3 $R^{11}$,
  $C_1$–$C_6$ alkylcarbonyl substituted with 0–3 $R^{11}$,
  $C_1$–$C_6$ alkoxycarbonyl substituted with 0–3 $R^{11}$,
  $C_1$–$C_6$ alkylaminocarbonyl substituted with 0–3 $R^{11}$
  benzoyl substituted with 0–3 $R^{12}$,
  phenoxycarbonyl substituted with 0–3 $R^{12}$,
  phenylaminocarbonyl substituted with 0–3 $R^{12}$,
  or any group that, when administered to a mammalian subject as part of a compound of Formula (I), cleaves to form a free hydroxyl, free amino or free sulfhydryl;

each of $R^{22}$ and $R^{23}$ is independently:
  hydrogen,
  $C_1$–$C_8$ alkyl substituted with 0–3 $R^{31}$,
  $C_2$–$C_8$ alkenyl substituted with 0–3 $R^{31}$,
  $C_2$–$C_8$ alkynyl substituted with 0–3 $R^{31}$,
  a $C_3$–$C_{14}$ carbocyclic ring system substituted with 0–5 $R^{31}$ or 0–5 $R^{32}$ or
  a 5- to 10-membered heterocyclic ring system containing 1 to 4 heteroatoms independently selected from oxygen, nitrogen or sulfur, the heterocyclic ring system being substituted with 0–2 $R^{32}$;

alternatively, $R^{22}$ can join with $R^4$ or $R^{4A}$ to form a 5- or 6- membered fused heterocyclic ring or carbocyclic ring substituted with 0–2 $R^{12}$, the heterocyclic ring containing 1–3 heteroatoms independently selected from nitrogen, sulfur or oxygen;

alternatively, $R^{23}$ can join with $R^7$ or $R^{7A}$ to form a 5- or 6- membered fused heterocyclic ring or carbocyclic ring substituted with 0–2 $R^{12}$, the heterocyclic ring containing 1–3 heteroatoms independently selected from nitrogen, sulfur or oxygen;

alternatively, $R^{22}$ or $R^{23}$ can join with $R^5$ or $R^6$ to form a 0- to 7- membered bridge to form a carbocyclic or heterocyclic ring, said bridge being substituted with 0–2 $R^{12}$ and the bridge containing 0–3 heteroatoms independently selected from nitrogen, sulfur or oxygen;

alternatively, the atoms to which $R^{22}$ and $R^{4A}$ are appended may be joined together with a double bond;

alternatively, the atoms to which $R^{23}$ and $R^{7A}$ are appended may be joined together with a double bond;

Z is: O or S;

each $R^{31}$ is independently:
  keto, halogen, cyano, —$CH_2N(R^{13})(R^{14})$, —$N(R^{13})(R^{14})$, —$C(=O)O(R^{13})$, —$C(=O)(R^{11})$, —$OC(=O)(R^{13})$, —$O(R^{13})$, $C_2$–$C_6$ alkoxyalkyl, —$S(=O)_m(R^{13})$, —$NHC(=NH)NH(R^{13})$, —$C(=NH)NH(R^{13})$, —$C(=O)N(R^{13})(R^{14})$, —$N(R^{14})C(=O)(R^{13})$, =N—$O(R^{14})$, —$N(R^{14})C(=O)O(R^{14})$, —$OC(=O)N(R^{13})(R^{14})$, —$N(R^{13})C(=O)N(R^{13})(R^{14})$, —$N(R^{14})S(=O)_2N(R^{13})(R^{14})$, —$N(R^{14})S(=O)_2(R^{13})$, —$S(=O)_2N(R^{13})(R^{14})$, $C_1$–$C_4$ alkyl, $C_2$–$C_4$ alkenyl, $C_3$–$C_{10}$ cycloalkyl, $C_3$–$C_6$ cycloalkylmethylene, phenylmethyl, phenethyl, phenoxy, phenylmethoxy, nitro, $C_7$–$C_{10}$ arylalkyl, hydroxamic acid, hydrazide, oxime, boronic acid, sulfonamide, formyl, $C_3$–$C_6$ cycloalkoxy, $C_1$–$C_4$ alkyl substituted with —$N(R^{13})(R^{14})$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$OCH_2C(=O)O(R^{13})$, 2-(1-morpholino)ethoxy, azido, —$C(R^{14})=N—O(R^{14})$,
  a $C_5$–$C_{14}$ carbocyclic residue substituted with 0–5 $R^{32}$,
  a 5- to 10-membered heterocyclic ring system containing 1 to 4 heteroatoms independently selected from oxygen, nitrogen or sulfur, the heterocyclic ring system being substituted with 0–2 $R^{32}$ or
  1–3 amino acids, linked together via amide bonds, and linked to $R^{22}$ or $R^{23}$ via the amine or carboxylate terminus;

each $R^{32}$ when a substituent on carbon, is independently:
  phenethyl, phenoxy, $C_3$–$C_{10}$ cycloalkyl, $C_3$–$C_6$ cycloalkylmethylene, $C_7$–$C_{10}$ arylalkyl, hydrazide, oxime, $C_2$–$C_6$ alkoxyalkyl, methylenedioxy, ethylenedioxy, $C_1$–$C_4$ alkylcarbonyloxy, —$NHS(=O)_2(R^{14})$, phenylmethoxy, halogen, 2-(1-morpholino)ethoxy, —$C(=O)O(R^{13})$, hydroxamic acid, —$C(=O)N(R^{13})N(R^{13})(R^{14})$, cyano, boronic acid, sulfonamide, formyl, $C_3$–$C_6$ cycloalkoxy, $C_1$–$C_4$ haloalkyl, $C_1$–$C_4$ haloalkoxy, $C_2$–$C_4$ haloalkenyl, $C_2$–$C_4$ haloalkynyl, —$N(R^{13})(R^{14})$, —$C(R^{14})=N—O(R^{14})$, —$NO_2$, —$O(R^{13})$, —$N(R^{40})(R^{41})$, —$S(=O)_m(R^{13})$, —$S(=O)_mN(R^{13})(R^{14})$, —$C(=O)N(R^{13})(R^{14})$, —$OC(=O)N(R^{13})(R^{14})$, —$C(=O)(R^{11})$, —$OC(=O)(R^{11})$, —$OC(=O)O(R^{13})$, phenyl, —$C(=O)N(R^{13})$—($C_1$–$C_4$ alkyl)-$N(R^{13})(R^{14})$, —$C(=O)N(R^{40})(R^{41})$, —$C(=O)N(R^{13})C(R^{11})_2N(R^{13})(R^{14})$, —$C(=O)N(R^{13})C(R^{11})_2N(R^{13})NH(R^{14})$, —$C(=O)N(R^{13})C(R^{11})_2N(R^{13})C(=O)O(R^{13})$, —$C(=O)N(R^{13})$—($C_1$–$C_4$ alkyl)-$N(R^{13})C(=O)O(R^{13})$, —$C(=O)N(R^{13})$—($C_1$–$C_4$ alkyl)-$R^{11}$, —$C(=O)C(R^{11})_2N(R^{13})(R^{14})$, —$C(=O)C(R^{11})_2N(R^{13})NH(R^{14})$, —$C(=O)C(R^{11})_2N(R^{13})C(=O)O(R^{13})$, —$C(=O)$—($C_1$–$C_4$ alkyl)—$N(R^{13})(R^{14})$, —$C(=O)$—($C_1$–$C_4$ alkyl)—$N(R^{13})C(=O)O(R^{13})$,
  $C_1$–$C_4$ alkoxy substituted with 0–4 groups selected from: $R^{11}$, $C_3$–$C_6$ cycloalkyl, —$C(=O)O(R^{13})$, —$C(=O)N(R^{13})(R^{14})$, —$N(R^{13})(R^{14})$ or hydroxyl,
  $C_1$–$C_4$ alkyl substituted with 0–4 groups selected from: $R^{11}$, =$N(R^{14})$, =$NN(R^{13})C(=O)N(R^{13})(R^{14})$ or —$N(R^{13})(R^{14})$,
  $C_2$–$C_4$ alkenyl substituted with 0–4 $R^{11}$
  $C_2$–$C_4$ alkynyl substituted with 0–4 $R^{11}$
  a 5- or 6-membered heterocyclic ring containing from 1 to 4 heteroatoms independently selected from oxygen, nitrogen or sulfur,
  a 3- or 4-carbon aliphatic chain attached to an adjacent carbon on the ring to which it is appended, to form a fused 5- or 6-membered ring, the 5- or 6-membered ring being optionally substituted on the aliphatic carbons with halogen, $C_1-C_4$ alkyl, $C_1-C_4$ alkoxy, hydroxyl—$N(R^{13})(R^{14})$, or when $R^{32}$ is attached to a saturated carbon atom, $R^{32}$ may be =O or =S;

each $R^{32}$ when a substituent on nitrogen, is independently:
  phenyl, phenylmethyl, phenethyl, hydroxyl, $C_1-C_4$ hydroxyalkyl, $C_1-C_4$ alkoxy, $C_1-C_4$ alkyl, $C_3-C_6$cycloalkyl, $C_3-C_6$ cycloalkylmethylene, —$CH_2N(R^{13})(R^{14})$, —$N(R^{13})(R^{14})$, $C_2-C_6$alkoxyalkyl, $C_1-C_4$ haloalkyl, $C_1-C_4$alkoxycarbonyl, —C(=O)OH, $C_1-C_4$ alkylcarbonyloxy, $C_1-C_4$ alkylcarbonyl or —$C(R^{14})$=N—$O(R^{14})$;

$R^{40}$ is: hydrogen or $C_1-C_3$ alkyl;

$R^{41}$ is: —$C(=O)N(R^{13})(R^{14})$, —$C(=O)N(R^{13})NH(R^{14})$, —$C(=O)C(R^{11})_2N(R^{13})(R^{14})$, —$C(=O)C(R^{11})_2N(R^{13})NH(R^{14})$, —$C(=O)C(R^{11})_2N(R^{13})C(=O)O(R^{13})$, —C(=O)H, —$C(=O)(R^{11})$, —C(=O)—$(C_1-C_4$ alkyl)—$N(R^{13})(R^{14})$, —C(=O)—$(C_1-C_4$ alkyl)—$N(R^{13})C(=O)O(R^{13})$ or 1–3 amino acids linked together via amide bonds and linked to the N atom via the carboxylate terminus; and n is: 0, 1 or 2;

provided that:

$R^4$, $R^{4A}$, $R^7$ and $R^{7A}$ are not all hydrogen;

when $R^4$ and $R^{4A}$ are both hydrogen, $R^{22}$ is not hydrogen, and when $R^7$ and $R^{7A}$ are both hydrogen, $R^{23}$ is not hydrogen.

26. The method according to claim 25, wherein the direct alkylation of step (a) comprises treating a compound of Formula (IIa) with a base and an alkylating agent, where the alkylating agent has the Formula $R^{16}X^1$ wherein $R^{16}$ is:

$C_1-C_8$ alkyl substituted with 0–3 $R^{31}$ $C_2-C_8$ alkenyl substituted with 0–3 $R^{31}$ $C_2-C_8$ alkynyl substituted with 0–3 $R^{31}$ a $C_3-C_{14}$ carbocyclic ring system substituted with 0–5 $R^{31}$ or 0–5 $R^{32}$, or a 5- to 10-membered heterocyclic ring system containing 1 to 4 heteroatoms independently selected from oxygen, nitrogen or sulfur, the heterocyclic ring system being substituted with 0–2 $R^{32}$; and $X^1$ is a leaving group susceptible to displacement with an amino nitrogen.

27. The method according to claim 26, wherein the leaving group $X^1$ is halide, tosylate, mesylate or acetate.

28. The method according to claim 26, wherein the compound of Formula (IIa) and the alkylating agent of Formula $R^{16}X^1$ are contacted in a molar ratio of between about 1:0.9 and about 1:1.5.

29. The method according to claim 26, wherein the base is potassium carbonate, sodium carbonate, lithium carbonate, cesium carbonate, potassium bicarbonate or sodium bicarbonate.

30. The method according to claim 26, wherein the direct alkylation is conducted in the presence of a phase transfer agent.

31. The method according to claim 30, wherein the phase transfer agent is tetrabutylammonium iodide and potassium iodide.

32. The method according to claim 26, wherein the direct alkylation is conducted in a solvent selected from the group consisting of acetonitrile and tetrahydrofuran, and wherein the compound of Formula (IIa) is present in the solvent at a concentration of about 0.03 molar to about 3.0 molar, and wherein the base is potassium carbonate, and wherein about two equivalents of base are present for each equivalent of the compound of Formula (IIa).

33. The method according to claim 25, wherein the reductive amination of step (a) comprises reacting a compound of Formula (IIa) with a carbonyl compound to form an intermediate oxime, and reacting the intermediate oxime with a reducing agent to form a compound of Formula (IIb), wherein the carbonyl compound is $C_1-C_8$ alkane substituted with 0–3 $R^{31}$, $C_2-C_8$ alkene substituted with 0–3 $R^{31}$, $C_2-C_8$ alkyne substituted with 0–3 $R^{31}$, a $C_3-C_{14}$ carbocyclic ring substituted with 0–5 $R^{31}$ or 0–5 $R^{32}$, and a 5- to 10-membered heterocyclic ring containing 1 to 4 heteroatoms independently selected from oxygen, nitrogen or sulfur, the heterocyclic ring being substituted with 0–2 $R^{32}$, with the proviso that at least one methylene group (—$CH_2$—) is replaced with a carbonyl group (—C(=O)—).

34. The method according to claim 33, wherein the reducing agent is $NaBH_4$, lithium aluminum hydride ($LiAlH_4$), sodium cyanoborohydride ($NaBH_3CN$), borane complexes including $BH_3$.THF, $BH_3$.$SMe_2$, $BH_3$.amine including pyridine, and other borane compounds including BH $(OAc)_3$, BH $(O_2CCF_3)_2$, $NaBH(OAc)_3$, (t-butyl)$NH_2BH_3$, $LiBH(Et)_3$, $LiBH(t-butyl)_3$, $NaAlH_2$ $(O(CH_2)_2OCH_3)$, LiBH (sec-butyl)$_3$ or Zn $(BH_3CN)_2$.

35. The method according to claim 33, wherein the molar ratio of the carbonyl compound to the compound of Formula (IIa) is about 1:1.

36. The method according to claim 25, wherein the successive acylation and reduction of step (a) comprises reacting a compound of Formula (IIa) with an acylating agent of Formula $R^{17}(C=O)X^2$ to form an amide compound, and the amide compound is reacted with a reducing agent to form a compound of Formula (IIb), wherein $R^{17}$ is:

$C_1-C_7$ alkyl substituted with 0–3 $R^{31}$, $C_2-C_7$ alkenyl substituted with 0–3 $R^{31}$ $C_2-C_7$ alkynyl substituted with 0–3 $R^{31}$, or —$R^{31}$; and $X^2$ is a leaving group.

37. The method according to claim 36 wherein the leaving group $X^2$ is halide, —$OR^{17}$ or —OC(=O) $R^{17}$.

38. The method according to claim 36 wherein the molar ratio of the acylating agent to the compound of Formula (IIa) is about 1:1.

39. The method according to claim 36, wherein the reducing agent is lithium aluminum hydride ($LiAlH_4$), $BH_3$.THF, $BH_3$.$SMe_2$, $B_2H_6$, $NaBH_4$ and $MeSO_3H$ in DMSO, $(Bu)_4NBH_4$ in methylene chloride, $NaBH_4$-$TiCl_4$ in dimethoxyethane, $NiCl_2$ in methanol, heterogeneous catalytic hydrogenation with Cu chromite, Ba/Cu chromite, Raney nickel, Raney cobalt, or rhenium on carbon.

40. The method according to claim 25, wherein step (b) comprises reacting a compound of Formula (IIb) with either carbonyl diimidazole, thereby forming a cyclic urea of Formula (Ib) having Z=O, or thiocarbonyl diimidazole, thereby forming a cyclic urea of Formula (Ib) having Z=S.

41. The method according to claim 25, wherein the aqueous acid solution of step (c)(i) is an organic carboxylic acid.

42. The method according to claim 25, wherein the aqueous acid solution of step (c)(i) is an aqueous citric acid solution.

43. The method according to claim 25, wherein step (d) comprises treating the product of step (c)(ii) with an alkylating agent of Formula $R^{16}X^1$ in the presence of a base, wherein $R^{16}$ is:

$C_1$–$C_8$ alkyl substituted with 0–3 $R^{31}$,
$C_2$–$C_8$ alkenyl substituted with 0–3 $R^{31}$,
$C_2$–$C_8$ alkynyl substituted with 0–3 $R^{31}$,
a $C_3$–$C_{14}$ carbocyclic ring system substituted with 0–5 $R^{31}$ or 0–5 $R^{32}$ or
a 5- to 10-membered heterocyclic ring system containing 1 to 4 heteroatoms independently selected from oxygen, nitrogen or sulfur, the heterocyclic ring system being substituted with 0–2 $R^{32}$; and
$X^1$ is a leaving group.

44. The method according to claim 43, wherein the leaving group $X^1$ is halide, mesylate, tosylate or acetate.

45. The method according to claim 43, wherein the base is sodium hydride.

46. The method according to claim 43, wherein the molar ratio of the product of step (c)(ii) to the alkylating agent is about 1:1.

47. A method for preparing and purifying a cyclic urea compound of Formula (Ib) comprising the steps:

(a) converting a compound of Formula (IIa) to a compound of Formula (IIb) by any of direct alkylation, reductive amination, or successive acylation and reduction, (b) converting the compound of Formula (IIb) from step (a) to a product comprising a cyclic urea compound of Formula (Ib), (c) purifying the product of step (b) by
  (i) washing the product of step (b) with an aqueous acid solution, resulting in a washed product, and
  (ii) eluting the washed product of step (c)(i) through a bed of silica gel to produce a substantially pure compound of Formula (Ib)

wherein,
the compound of Formula (IIa) has the structure shown in Formula (II) with the proviso that $R^{22}$ and $R^{23}$ are hydrogen,
the compound of Formula (IIb) has the structure shown in Formula (II) with the proviso that only one of $R^{22}$ or $R^{23}$ is hydrogen,
the compound of Formula (Ib) has the structure shown in Formula (I) with the proviso that only one of $R^{22}$ or $R^{23}$ is hydrogen,
compound (I) has a Formula:

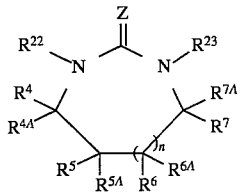
(I)

including a pharmaceutically acceptable salt or prodrug form thereof, and compound (II) has a Formula:

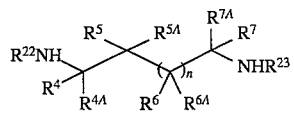
(II)

wherein, for each compound of Formula (I) and Formula (II):

each of $R^4$ and $R^7$ is independently:
  hydrogen, —O($R^{13}$), —S($R^{13}$), —C(=O)O($R^{13}$),
  $C_1$–$C_8$ alkyl substituted with 0–3 $R^{11}$,
  $C_2$–$C_8$ alkenyl substituted with 0–3 $R^{11}$,
  $C_2$–$C_8$ alkynyl substituted with 0–3 $R^{11}$,
  a $C_3$–$C_{14}$ carbocyclic ring system substituted with 0–3 $R^{11}$ or 0–3 $R^{12}$ or
  a 5- to 10-membered heterocyclic ring system containing 1 to 4 heteroatoms independently selected from oxygen, nitrogen or sulfur, the heterocyclic ring system being substituted with 0–2 $R^{12}$;

each of $R^{4A}$ and $R^{7A}$ is independently:
  hydrogen, —O($R^{13}$), —S($R^{13}$), —C(=O)O($R^{13}$),
  $C_1$–$C_4$ alkyl unsubstituted or substituted with halogen or $C_1$–$C_2$ alkoxy, or
  phenylmethyl unsubstituted or substituted with halogen or $C_1$–$C_2$ alkoxy;

$R^4$ and $R^{4A}$ can alternatively join to form a 5- to 7-membered carbocyclic ring substituted with 0–2 $R^{12}$;
$R^7$ and $R^{7A}$ can alternatively join to form a 5- to 7-membered carbocyclic ring substituted with 0–2 $R^{12}$;

each of $R^5$ and $R^{5A}$ is independently:
  hydrogen, halogen, —N($R^{20}$)$_2$, —S($R^{20}$), —O($R^{20}$) or
  $C_1$–$C_6$ alkyl substituted with 0–3 $R^{11}$;
$R^5$ and $R^{5A}$ can alternatively join together to form a =O, =S or a ketal ring;

each of $R^6$ and $R^{6A}$ is independently:
  hydrogen, halogen, —N($R^{20}$)$_2$, —S($R^{20}$), —O($R^{21}$) or
  $C_1$–$C_6$ alkyl substituted with 0–3 $R^{11}$;
$R^6$ and $R^{6A}$ can alternatively join together to form a =O, =S or a ketal ring;

$R^5$ and $R^6$ can alternatively join together to form an epoxide or aziridine ring; —OCH$_2$SCH$_2$O—, —OS(=O)O—, —OC(=O)O—, —OCH$_2$O—, —OC(=S)O—, —OC(=O)C(=O)O—, —OC(CH$_3$)$_2$O—, —OC((CH$_2$)$_3$NH$_2$)(CH$_3$)O—, —OC(OCH$_3$)(CH$_2$CH$_2$CH$_3$)O—, —OS(=O)$_2$O—, —NHC(=O)NH—, —OC(=O)NH—, —NHC(=O)O—, —NHCH$_2$O—, —OCH$_2$ NH—, —NHC(=S)O—, —OC(=S)NH—, —OS(=O)NH—, —NHS(=O)O—, —NHC(=O)C(=O)O—, —OC(=O)C(=O)NH—, —NHC(=O)C(=O)NH—, —NHC(CH$_3$)$_2$O—, —OC(CH$_3$)$_2$NH— or any group that, when administered to a mammalian subject as part of a compound of Formula (I), cleaves to form a compound having two free hydroxyl groups, or two free amino groups, or one free hydroxyl group and one free amino group;

each $R^{11}$ is independently:
  hydrogen, keto, halogen, cyano, phenylmethyl, phenethyl, methylenedioxy, ethylenedioxy, hydroxamic acid, hydrazide, boronic acid, sulfonamide, azido, formyl, phenoxy, phenylmethoxy, nitro, —CH$_2$N($R^{13}$)($R^{14}$), —N($R^{13}$)($R^{14}$), —OCH$_2$C(=O)OH, —C(=O)O($R^{13}$), —OC(=O)($R^{13}$), —O($R^{13}$), $C_2$–$C_6$ alkoxyalkyl, —S(=O)$_m$($R^{13}$), —NHC(=NH)NH($R^{13}$), —C(=NH)NH($R^{13}$), —C(=O)N($R^{13}$)($R^{14}$), —N($R^{14}$)C(=O)($R^{13}$), =N—O($R^{14}$), —N($R^{14}$)C(=O)O($R^{14}$), —OC(=O)N($R^{13}$)($R^{14}$), —N($R^{13}$)C(=O)N($R^{13}$)($R^{14}$), —C($R^{14}$)=N—O($R^{14}$), —N($R^{14}$) S(=O)$_2$N($R^{13}$)($R^{14}$), —N($R^{14}$)S(=O)$_2$($R^{13}$), —S(=O)$_2$N($R^{13}$)($R^{14}$), $C_1$–$C_4$ alkyl, $C_2$–$C_4$ alkenyl, $C_3$–$C_{10}$ cycloalkyl, $C_3$–$C_6$ cycloalkylmethylene, $C_7$–$C_{10}$ arylalkyl, $C_3$–$C_6$ cycloalkoxy, $C_1$–$C_4$ alkyl substituted with —N($R^{13}$)($R^{14}$), $C_1$–$C_4$ hydroxyalkyl, $C_1$–$C_4$ haloalkyl, $C_1$–$C_4$ haloalkoxy, $C_1$–$C_4$ alkoxycarbonyl, $C_1C_4$ alkylcarbonyloxy, $C_1C_4$ alkylcarbonyl, $C_1$–$C_4$ alkylcarbonylamino, 2-(1-morpholino)ethoxy, —($C_1$–$C_3$ alkyl) aryl substituted with 0–2 $R^{12}$, a $C_5$–$C_{14}$ carbocyclic residue substituted with 0–3 $R^{12}$, or a 5- to 10-membered heterocyclic ring system containing 1 to 4 heteroatoms independently selected from oxygen, nitrogen or sulfur, the heterocyclic ring system being substituted with 0–3 $R^{12}$; and 1–3 amino acids linked together via amide bonds, and linked to $R^4$ $R^7$ $R^{20}$ or $R^{21}$ via the amine or carboxylate terminus;

m is: 0, 1 or 2;

each $R^{11A}$ is independently:
  H, keto, halogen, cyano, —$CH_2NH_2$, —$NH_2$, —C(=O)OH, —OC(=O)($C_1$–$C_3$ alkyl), —OH, $C_2$–$C_6$ alkoxyalkyl, —C(=O)$NH_2$, —OC(=O)$NH_2$, —NHC(=O)$NH_2$, —S(=O)$_2NH_2$, $C_1$–$C_4$ alkyl, $C_2$–$C_4$ alkenyl, $C_3$–$C_{10}$ cycloalkyl, $C_3$–$C_6$ cycloalkylmethylene, benzyl, phenethyl, phenoxy, benzyloxy, nitro, $C_7$–$C_{10}$ arylalkyl, hydroxamic acid, hydrazide, boronic acid, $C_3$–$C_6$ cycloalkoxy, $C_1$–$C_4$ alkyl substituted with —$NH_2$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —OCH$_2$C(=O)OH, 2-(1-morpholino)ethoxy, azido, aryl($C_1$–$C_3$ alkyl), a $C_5$–$C_{14}$ carbocyclic residue, or a 5- to 10-membered heterocyclic ring system containing 1 to 4 heteroatoms independently selected from oxygen, nitrogen or sulfur;

each $R^{12}$ when a substituent on carbon, is independently:
  phenyl, phenylmethyl, phenethyl, phenoxy, phenylmethoxy, halogen, hydroxy, nitro, cyano, $C_1$–$C_4$ alkyl, $C_3$–$C_6$ cycloalkyl, $C_3$–$C_6$ cycloalkylmethylene, $C_7$–$C_{10}$ arylalkyl, $C_1$–$C_4$ alkoxy, —C(=O)OH, hydroxamic acid, hydrazide, boronic acid, sulfonamide, formyl, $C_3$–$C_6$ cycloalkoxy, —O($R^{13}$), $C_1$–$C_4$ alkyl substituted with —N($R^{13}$)($R^{14}$), —N($R^{13}$)($R^{14}$), $C_2$–$C_6$ alkoxyalkyl, $C_1$–$C_4$ hydroxyalkyl, methylenedioxy, ethylenedioxy, $C_1$–$C_4$ haloalkyl, $C_1$–$C_4$haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —S(=O)$_m$($R^{13}$), —S(=O)$_2$N($R^{13}$)($R^{14}$), —NHS(=O)$_2$ ($R^{14}$), —OCH$_2$C(=O)OH, 2-(1-morpholino)ethoxy, —C($R^{14}$)=N—O($R^{14}$), a 5- to 10-membered heterocyclic ring containing from 1 to 4 heteroatoms independently selected from oxygen, nitrogen or sulfur, the heterocyclic ring system being substituted with 0–3 $R^{15}$, a 3- or 4-carbon aliphatic chain attached to an adjacent carbon on the ring to which it is appended to form a fused 5- or 6-membered ring, the 5- or 6-membered ring being optionally substituted on any of the aliphatic carbons with halogen, $C_1$–$C_4$ alkyl, $C_1$–$C_4$ alkoxy, hydroxy, —N($R^{13}$)($R^{14}$), or when $R^{12}$ is a substituent on a saturated carbon atom, $R^{12}$ may alternatively be =O or =S;

each $R^{12}$ when a substituent on nitrogen, is independently:
  phenyl, phenylmethyl, phenethyl, hydroxy, $C_1$–$C_4$ hydroxyalkyl, $C_1$–$C_4$ alkoxy, $C_1$–$C_4$ alkyl, $C_3$–$C_6$cycloalkyl, $C_3$–$C_6$ cycloalkylmethylene, —CH$_2$N($R^{13}$)($R^{14}$), —N($R^{13}$)($R^{14}$), $C_2$–$C_6$ alkoxyalkyl, $C_1$–$C_4$ haloalkyl, $C_1$–$C_4$ alkoxycarbonyl, —C(=O)OH, $C_1$–$C_4$ alkylcarbonyloxy, $C_1$–$C_4$ alkylcarbonyl or —C($R^{14}$)=N—O ($R^{14}$);

each $R^{13}$ is independently:
  hydrogen,
  phenyl substituted with 0–3 $R^{11A}$,
  phenylmethyl substituted with 0–3 $R^{11A}$,
  $C_1$–$C_6$ alkyl substituted with 0–3 $R^{11A}$,
  $C_2$–$C_4$ alkenyl substituted with 0–3 $R^{11A}$,
  $C_1$–$C_6$ alkylcarbonyl substituted with 0–3 $R^{11A}$,
  $C_1$–$C_6$ alkoxycarbonyl substituted with 0–3 $R^{11A}$,
  $C_1$–$C_6$ alkylaminocarbonyl substituted with 0–3 $R^{11A}$,
  $C_3$–$C_6$ alkoxyalkyl substituted with 0–3 $R^{11A}$,
  an amine protecting group when $R^{13}$ is bonded to N, or
  a hydroxy protecting group when $R^{13}$ is bonded to O;

each $R^{14}$ is independently:
  hydrogen, hydroxy, trifluoromethyl, $C_1$–$C_6$ alkoxy, $C_2$–$C_6$ alkenyl, phenylmethyl, amino,
  $C_1$–$C_6$ alkyl substituted with 0–3 groups selected from hydroxy, $C_1$–$C_4$ alkoxy, halogen or amino,
  an amine protecting group when $R^{14}$ is bonded to N, or
  a hydroxy protecting group when $R^{14}$ is bonded to O;

$R^{13}$ and $R^{14}$ can alternatively join to form:
  —(CH$_2$)$_4$—, —(CH$_2$)$_5$—, —CH$_2$CH$_2$N($R^{15}$)CH$_2$CH$_2$— or —CH$_2$CH$_2$OCH$_2$CH$_2$—;

$R^{15}$ is: hydrogen or methyl;

each of $R^{20}$ and $R^{21}$ is independently:
  hydrogen,
  $C_1$–$C_6$ alkyl substituted with 0–3 $R^{11}$,
  $C_3$–$C_6$ alkoxyalkyl substituted with 0–3 $R^{11}$,
  $C_1$–$C_6$ alkylcarbonyl substituted with 0–3 $R^{11}$
  $C_1$–$C_6$ alkoxycarbonyl substituted with 0–3 $R^{11}$,
  $C_1$–$C_6$ alkylaminocarbonyl substituted with 0–3 $R^{11}$
  benzoyl substituted with 0–3 $R^{12}$,
  phenoxycarbonyl substituted with 0–3 $R^{12}$,
  phenylaminocarbonyl substituted with 0–3 $R^{12}$,
  or any group that, when administered to a mammalian subject as part of a compound of Formula (I), cleaves to form a free hydroxyl, free amino or free sulfhydryl;

each of $R^{22}$ and $R^{23}$ is independently:
  hydrogen,
  $C_1$–$C_8$ alkyl substituted with 0–3 $R^{31}$,
  $C_2$–$C_8$ alkenyl substituted with 0–3 $R^{31}$,
  $C_2$–$C_8$ alkynyl substituted with 0–3 $R^{31}$,
  a $C_3$–$C_{14}$ carbocyclic ring system substituted with 0–5 $R^{31}$ or 0–5 $R^{32}$, or
  a 5- to 10-membered heterocyclic ring system containing 1 to 4 heteroatoms independently selected from oxygen, nitrogen or sulfur, the heterocyclic ring system being substituted with 0–2 $R^{32}$;

alternatively, $R^{22}$ can join with $R^4$ or $R^{44}$ to form a 5- or 6-membered fused heterocyclic ring or carbocyclic ring substituted with 0–2 $R^{12}$, the heterocyclic ring containing 1–3 heteroatoms independently selected from nitrogen, sulfur or oxygen;

alternatively, $R^{23}$ can join with $R^7$ or $R^{7A}$ to form a 5- or 6-membered fused heterocyclic ring or carbocyclic ring substituted with 0–2 $R^{12}$ the heterocyclic ring containing 1–3 heteroatoms independently selected from nitrogen, sulfur or oxygen;

alternatively, $R^{22}$ or $R^{23}$ can join with $R^5$ or $R^6$ to form a 0- to 7- membered bridge to form a carbocyclic or heterocyclic ring, said bridge being substituted with 0–2 $R^{12}$ and the bridge containing 0–3 heteroatoms independently selected from nitrogen, sulfur or oxygen;

alternatively, the atoms to which $R^{22}$ and $R^{4A}$ are appended may be joined together with a double bond;

alternatively, the atoms to which $R^{23}$ and $R^{7A}$ are appended may be joined together with a double bond;

Z is: O or S;

each $R^{31}$ is independently:

keto, halogen, cyano, —CH$_2$N(R$^{13}$)(R$^{14}$), —N(R$^{13}$)(R$^{14}$), —C(=O)O(R$^{13}$), —C(=O)(R$^{11}$), —OC(=O)(R$^{13}$), —O(R$^{13}$), C$_2$–C$_6$ alkoxyalkyl, —S(=O)$_m$(R$^{13}$), —NHC(=NH)NH(R$^{13}$), —C(=NH)NH(R$^{13}$), —C(=O)N(R$^{13}$)(R$^{14}$), —N(R$^{14}$)C(=O)(R$^{13}$), =N—O(R$^{14}$), —N(R$^{14}$)C(=O)O(R$^{14}$), —OC(=O)N(R$^{13}$)(R$^{14}$), —N(R$^{13}$)C(=O)N(R$^{13}$)(R$^{14}$), —N(R$^{14}$)S(=O)$_2$N(R$^{13}$)(R$^{14}$), —N(R$^{14}$)S(=O)$_2$(R$^{13}$), —S(=O)$_2$N(R$^{13}$)(R$^{14}$), C$_1$–C$_4$ alkyl, C$_2$–C$_4$ alkenyl, C$_3$–C$_{10}$ cycloalkyl, C$_3$–C$_6$ cycloalkylmethylene, phenylmethyl, phenethyl, phenoxy, phenylmethoxy, nitro, C$_7$–C$_{10}$ arylalkyl, hydroxamic acid, hydrazide, oxime, boronic acid, sulfonamide, formyl, C$_3$–C$_6$ cycloalkoxy, C$_1$–C$_4$ alkyl substituted with —N(R$^{13}$)(R$^{14}$), C$_1$–C$_4$ hydroxyalkyl, methylenedioxy, ethylenedioxy, C$_1$–C$_4$ haloalkyl, C$_1$–C$_4$ haloalkoxy, C$_1$–C$_4$ alkoxycarbonyl, C$_1$–C$_4$ alkylcarbonyloxy, C$_1$–C$_4$ alkylcarbonyl, C$_1$–C$_4$ alkylcarbonylamino, —OCH$_2$C(=O)O(R$^{13}$), 2-(1-morpholino)ethoxy, azido, —C(R$^{14}$)=N—O(R$^{14}$), a C$_5$–C$_{14}$ carbocyclic residue substituted with 0–5 R$^{32}$ a 5- to 10-membered heterocyclic ring system containing 1 to 4 heteroatoms independently selected from oxygen, nitrogen or sulfur, the heterocyclic ring system being substituted with 0–2 R$^{32}$ or 1–3 amino acids, linked together via amide bonds, and linked to R$^{22}$ or R$^{23}$ via the amine or carboxylate terminus;

each $R^{32}$ when a substituent on carbon, is independently:

phenethyl, phenoxy, C$_3$–C$_{10}$ cycloalkyl, C$_3$–C$_6$ cycloalkylmethylene, C$_7$–C$_{10}$ arylalkyl, hydrazide, oxime, C$_2$–C$_6$ alkoxyalkyl, methylenedioxy, ethylenedioxy, C$_1$–C$_4$ alkylcarbonyloxy, —NHS(=O)$_2$ (R$^{14}$), phenylmethoxy, halogen, 2-(1-morpholino)ethoxy, —C(=O)O(R$^{13}$), hydroxamic acid, —C(=O)N(R$^{13}$)N(R$^{13}$)(R$^{14}$), cyano, boronic acid, sulfonamide, formyl, C$_3$–C$_6$ cycloalkoxy, C1—C$_4$ haloalkyl, C$_1$–C$_4$ haloalkoxy, C$_2$–C$_4$ haloalkenyl, C$_2$–C$_4$ haloalkynyl, —N(R$^{13}$)(R$^{14}$), —C(R$^{14}$)=N—O (R$^{14}$), —NO$_2$, —O(R$^{13}$), —N(R$^{40}$)(R$^{41}$), —S(=O)$_m$(R$^{13}$), —S(=O)$_m$N(R$^{13}$)(R$^{14}$), —C(=O)N(R$^{13}$)(R$^{14}$), —OC(=O)N(R$^{13}$)(R$^{14}$), —C(=O)(R$^{11}$), —OC(=O)(R$^{11}$), —OC(=O)O(R$^{13}$), phenyl, —C(=O)N(R$^{13}$)—(C$_1$–C$_4$ alkyl)-N(R$_{13}$)(R$^{14}$), —C(=O)N(R$^{40}$)(R$^{41}$), —C(=O)N(R$^{13}$)C(R$^{11}$)$_2$N(R$^{13}$)(R$^{14}$), —C(=O)N(R$^{13}$)C(R$^{11}$)$_2$N(R$^{13}$)NH(R$^{14}$), —C(=O)N(R$^{13}$)C(R$^{11}$)$_2$N(R$^{13}$)C(=O)O(R$^{13}$), —C(=O)N(R$^{13}$)—(C$_1$–C$_4$ alkyl)-N(R$_{13}$)C(=O)O(R$^{13}$), —C(=O)N(R$^{13}$)—(C$_1$–C$_4$ alkyl)-R$^{11}$, —C(=O)C(R$^{11}$)$_2$N(R$^{13}$)(R$^{14}$), —C(=O)C(R$^{11}$)$_2$N(R$^{13}$)NH(R$^{14}$), —C(=O)C(R$^{11}$)$_2$N(R$^{13}$)C(=O)O(R$^{13}$), —C(=O)—(C$_1$–C$_4$ alkyl)—N(R$^{13}$)(R$^{14}$), —C(=O)—(C$_1$–C$_4$ alkyl) —N(R$^{13}$)C(=O)O(R$^{13}$), C$_1$–C$_4$ alkoxy substituted with 0–4 groups selected from: R$^{11}$, C$_3$–C$_6$ cycloalkyl, —C(=O)O(R$^{13}$), —C(=O)N(R$^{13}$)(R$^{14}$), —N(R$^{13}$)(R$^{14}$) or hydroxyl, C$_1$–C$_4$ alkyl substituted with 0–4 groups selected from: R$^{11}$ =N(R$^{14}$), =NN(R$^{13}$)C(=O)N(R$^{13}$)(R$^{14}$) or —N(R$^{13}$)(R$^{14}$), C$_2$–C$_4$ alkenyl substituted with 0–4 R$^{11}$, C$_2$–C$_4$ alkynyl substituted with 0–4 R$^{11}$, a 5- or 6-membered heterocyclic ring containing from 1 to 4 heteroatoms independently selected from oxygen, nitrogen or sulfur, a 3- or 4-carbon aliphatic chain attached to an adjacent carbon on the ring to which it is appended, to form a fused 5- or 6-membered ring, the 5- or 6-membered ring being optionally substituted on the aliphatic carbons with halogen, C$_1$–C$_4$ alkyl, C$_1$–C$_4$ alkoxy, hydroxyl—N(R$^{13}$)(R$^{14}$), or when $R^{32}$ is attached to a saturated carbon atom, $R^{32}$ may be =O or =S;

each $R^{32}$, when a substituent on nitrogen, is independently:

phenyl, phenylmethyl, phenethyl, hydroxyl, C$_1$–C$_4$ hydroxyalkyl, C$_1$–C$_4$ alkoxy, C$_1$–C$_4$ alkyl, C$_3$–C$_6$ cycloalkyl, C$_3$–C$_6$ cycloalkylmethylene, —CH$_2$N(R$^{13}$)(R$^{14}$), —N(R$^{13}$)(R$^{14}$), C$_2$–C$_6$ alkoxyalkyl, C$_1$–C$_4$ haloalkyl, C$_1$–C$_4$ alkoxycarbonyl, —C(=O)OH, C$_1$–C$_4$ alkylcarbonyloxy, C$_1$–C$_4$ alkylcarbonyl or —C(R$^{14}$)=N—O(R$^{14}$);

$R^{40}$ is: hydrogen or C$_1$–C$_3$ alkyl;

$R^{41}$ is: —C(=O)N(R$^{13}$)(R$^{14}$), —C(=O)N(R$^{13}$)NH(R$^{14}$), —C(=O)C(R$^{11}$)$_2$N(R$^{13}$)(R$^{14}$), —C(=O)C(R$^{11}$)$_2$N(R$^{13}$)NH (R$^{14}$), —C(=O)C(R$^{11}$)$_2$N(R$^{13}$)C(=O)O(R$^{13}$), —C(=O)H, —C(=O)(R$^{11}$), —C(=O)—(C$_1$–C$_4$ alkyl)—N(R$^{13}$)(R$^{14}$), C(=O)—(C$_1$–C$_4$ alkyl)—N(R$^{13}$)C(=O)O(R$^{13}$) or 1–3 amino acids linked together via amide bonds and linked to the N atom via the carboxylate terminus; and n is: 0, 1 or 2;

provided that:

$R^4$, $R^{4A}$, $R^7$ and $R^{7A}$ are not all hydrogen;

when $R^4$ and $R^{4A}$ are both hydrogen, $R^{22}$ is not hydrogen, and when $R^7$ and $R^{7A}$ are both hydrogen, $R^{23}$ is not hydrogen.

48. The method according to claim 47, wherein the direct alkylation of step (a) comprises treating a compound of Formula (IIa) with a base and an alkylating agent, where the alkylating agent has the Formula R$^{16}$X$^1$, wherein R$^{16}$ is:

C$_1$–C$_8$ alkyl substituted with 0–3 R$^{31}$,

C$_2$–C$_8$ alkenyl substituted with 0–3 R$^{31}$,

C$_2$–C$_8$ alkynyl substituted with 0–3 R$^{31}$, a C$_3$–C$_{14}$ carbocyclic ring system substituted with 0–5 R$^{31}$ or 0–5 R$^{32}$, or a 5- to 10-membered heterocyclic ring system containing 1 to 4 heteroatoms independently selected from oxygen, nitrogen or sulfur, the heterocyclic ring system being substituted with 0–2 R$^{32}$; and X$^1$ is a leaving group susceptible to displacement with an amino nitrogen.

49. The method according to claim 48, wherein the leaving group is halide, tosylate, mesylate or acetate.

50. The method according to claim 48, wherein the compound of Formula (IIa) and the alkylating agent of Formula R$^{16}$X$^1$ are contacted in a molar ratio of between about 1:0.9 and about 1:1.5.

51. The method according to claim 48, wherein the base is potassium carbonate, sodium carbonate, lithium carbonate, cesium carbonate, potassium bicarbonate or sodium bicarbonate.

52. The method according to claim 48, wherein the direct alkylation is conducted in the presence of a phase transfer agent.

53. The method according to claim 52, wherein the phase transfer agent is tetrabutylammonium iodide and potassium iodide.

54. The method according to claim 48, wherein the direct alkylation is conducted in a solvent selected from the group consisting of acetonitrile and tetrahydrofuran, and wherein the compound of Formula (IIa) is present in the solvent at a concentration of about 0.03 molar to about 3.0 molar, and wherein the base is potassium carbonate, and wherein about two equivalents of base are present for each equivalent of the compound of Formula (IIa).

55. The method according to claim 47, wherein the reductive amination of step (a) comprises reacting a compound of Formula (IIa) with a carbonyl compound to form an intermediate oxime, and reacting the intermediate oxime with a reducing agent to form a compound of Formula (IIb), wherein the carbonyl compound is $C_1$–$C_8$ alkane substituted with 0–3 $R^{31}$, $C_2$–$C_8$ alkene substituted with 0–3 $R^{31}$, $C_2$–$C_8$ alkyne substituted with 0–3 $R^{31}$, a $C_3$–$C_{14}$ carbocyclic ring substituted with 0–5 $R^{31}$ or 0–5 $R^{32}$, and a 5- to 10-membered heterocyclic ring containing 1 to 4 heteroatoms independently selected from oxygen, nitrogen or sulfur, the heterocyclic ring being substituted with 0–2 $R^{32}$, with the proviso that at least one methylene group (—$CH_2$—) is replaced with a carbonyl group (—C(=O)—).

56. The method according to claim 55, wherein the reducing agent is $NaBH_4$, lithium aluminum hydride ($LiAlH_4$), sodium cyanoborohydride ($NaBH_3CN$), borane complexes including $BH_3$.THF, $BH_3$.SMe$_2$, $BH_3$.amine including pyridine, and other borane compounds including BH(OAc)$_3$, BH(O$_2$CCF$_3$)$_2$, NaBH(OAc)$_3$, (t-butyl)NH$_2$BH$_3$, LiBH(Et)$_3$, LiBH(t-butyl)$_3$, NaAlH$_2$(O(CH$_2$)$_2$OCH$_3$), LiBH (sec-butyl)$_3$ or Zn (BH$_3$CN)$_2$.

57. The method according to claim 55, wherein the molar ratio of the carbonyl compound to the compound of Formula (IIa) is about 1:1.

58. The method according to claim 47, wherein the successive acylation and reduction of step (a) comprises reacting a compound of Formula (IIa) with an acylating agent of Formula $R^{17}(C=O)X^2$ to form an amide compound, and the amide compound is reacted with a reducing agent to form a compound of Formula (IIb), wherein $R^{17}$ is:

$C_1$–$C_7$ alkyl substituted with 0–3 $R^{31}$, $C_2$–$C_7$ alkenyl substituted with 0–3 $R^{31}$, $C_2$–$C_7$ alkynyl substituted with 0–3 $R^{31}$ or —$R^{31}$; and $X^2$ is a leaving group.

59. The method according to claim 58 wherein the leaving group $X^2$ is halide, —$OR^{17}$ or —OC(=O) $R^{17}$.

60. The method according to claim 58 wherein the molar ratio of the acylating agent to the compound of Formula (IIa) is about 1:1.

61. The method according to claim 58, wherein the reducing agent is lithium aluminum hydride (LiAlH$_4$), BH$_3$.THF, BH$_3$.SMe$_2$, B$_2$H$_6$, NaBH$_4$ and MeSO$_3$H in DMSO, (Bu)$_4$NBH$_4$ in methylene chloride, NaBH$_4$—TiCl$_4$ in dimethoxyethane, NiCl$_2$ in methanol, heterogeneous catalytic hydrogenation with Cu chromite, Ba/Cu chromite, Raney nickel, Raney cobalt, or rhenium on carbon.

62. The method according to claim 47, wherein step (b) comprises reacting a compound of Formula (IIb) with either carbonyl diimidazole, thereby forming a cyclic urea of Formula (Ib) having Z=O, or thiocarbonyl diimidazole, thereby forming a cyclic urea of Formula (Ib) having Z=S.

63. The method according to claim 47, wherein the aqueous acid solution of step (c)(i) is an aqueous hydrochloric acid, nitric acid, phosphoric acid or citric acid solution.

64. The method according to claim 47, wherein the aqueous acid solution of step (c)(i) is an aqueous citric acid solution.

65. A method for preparing and purifying a cyclic urea compound of Formula (Ib) comprising the steps:

(a) converting a compound of Formula (IIb) to a product comprising a cyclic urea compound of Formula (Ib), (b) purifying the product of step (a) by
 (i) washing the product of step (a) with an aqueous acid solution, resulting in a washed product, and
 (ii) eluting the product of step (b)(i) through a bed of silica gel to produce a substantially pure compound of Formula (Ib), wherein, the compound of Formula (IIb) has the structure shown in Formula (II) with the proviso that only one of $R^{22}$ and $R^{23}$ is hydrogen, the compound of Formula (Ib) has the structure shown in Formula (I) with the proviso that only one of $R^{22}$ and $R^{23}$ is hydrogen, compound (I) has a Formula:

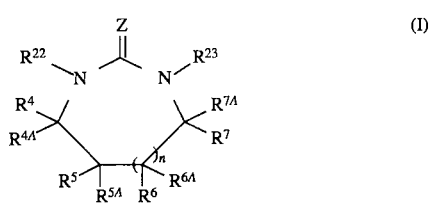

including a pharmaceutically acceptable salt or prodrug form thereof, and compound (II) has a Formula:

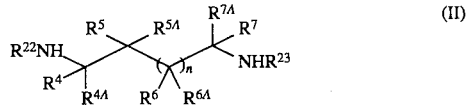

wherein for each compound of Formula (I) and Formula (II): each of $R^4$ and $R^7$ is independently:

hydrogen, —O($R^{13}$), —S($R^{13}$), —C(=O)O($R^{13}$), $C_1$–$C_8$ alkyl substituted with 0–3 $R^{11}$, $C_2$–$C_8$ alkenyl substituted with 0–3 $R^{11}$, $C_2$–$C_8$ alkynyl substituted with 0–3 $R^{11}$, a $C_3$–$C_{14}$ carbocyclic ring system substituted with 0–3 $R^{11}$ or 0–3 $R^{12}$ or a 5- to 10-membered heterocyclic ring system containing 1 to 4 heteroatoms independently selected from oxygen, nitrogen or sulfur, the heterocyclic ring system being substituted with 0–2 $R^{12}$;

each of $R^{4A}$ and $R^{7A}$ is independently:

hydrogen, —O($R^{13}$), —S($R^{13}$), —C(=O)O($R^{13}$), $C_1$–$C_4$ alkyl unsubstituted or substituted with halogen or $C_1$–$C_2$ alkoxy, or phenylmethyl unsubstituted or substituted with halogen or $C_1$–$C_2$ alkoxy;

$R^4$ and $R^{4A}$ can alternatively join to form a 5- to 7-membered carbocyclic ring substituted with 0–2 $R^{12}$;

$R^7$ and $R^{7A}$ can alternatively join to form a 5- to 7-membered carbocyclic ring substituted with 0–2 $R^{12}$;

each of $R^5$ and $R^{5A}$ is independently:

hydrogen, halogen, —N($R^{20}$)$_2$, —S($R^{20}$), —O($R^{20}$) or $C_1$–$C_6$ alkyl substituted with 0–3 $R^{11}$;

$R^5$ and $R^{5A}$ can alternatively join together to form a =O, =S or a ketal ring;

each of $R^6$ and $R^{6A}$ is independently:
hydrogen, halogen, —N($R^{20}$)$_2$, —S($R^{20}$), —O($R^{21}$) or $C_1$–$C_6$ alkyl substituted with 0–3 $R^{11}$;

$R^6$ and $R^{6A}$ can alternatively join together to form a =O, =S or a ketal ring;

$R^5$ and $R^6$ can alternatively join together to form an epoxide or aziridine ring; —OCH$_2$SCH$_2$O—, —OS(=O)O—, —OC(=O)O—, —OCH$_2$O—, —OC(=S)O—, —OC(=O)C(=O)O—, —OC(CH$_3$)$_2$O—, —OC((CH$_2$)$_3$NH$_2$)(CH$_3$)O—, —OC(OCH$_3$)(CH$_2$CH$_2$CH$_3$)O—, —OS(=O)$_2$O—, —NHC(=O)NH—, —OC(=O)NH—, —NHC(=O)O—, —NHCH$_2$O—, —OCH$_2$NH—, —NHC(=S)O—, —OC(=S)NH—, —OS(=O)NH—, —NHS(=O)O—, —NHC(=O)C(=O)O—, —OC(=O)C(=O)NH—, —NHC(=O)C(=O)NH—, —NHC(CH$_3$)$_2$O—, —OC(CH$_3$)$_2$NH— or any group that, when administered to a mammalian subject as part of a compound of Formula (I), cleaves to form a compound having two free hydroxyl groups, or two free amino groups, or one free hydroxyl group and one free amino group;

each $R^{11}$ is independently:
hydrogen, keto, halogen, cyano, phenylmethyl, phenethyl, methylenedioxy, ethylenedioxy, hydroxamic acid, hydrazide, boronic acid, sulfonamide, azido, formyl, phenoxy, phenylmethoxy, nitro, —CH$_2$N($R^{13}$)($R^{14}$), —N($R^{13}$)($R^{14}$), —OCH$_2$C(=O)OH, —C(=O)O($R^{13}$), —OC(=O)($R^{13}$), —O($R^{13}$), $C_2$–$C_6$ alkoxyalkyl, —S(=O)$_m$($R^{13}$), —NHC(=NH)NH($R^{13}$), —C(=NH)NH ($R^{13}$), —C(=O)N($R^{13}$)($R^{14}$), $R^{14}$)C(=O)($R^{13}$), =N—O($R^{14}$), —N —N($R^{14}$)C(=O)O($R^{14}$), —OC(=O)N($R^{13}$)($R^{14}$), —N($R^{13}$)C(=O)N($R^{13}$)($R^{14}$), —C($R^{14}$)=N—O($R^{14}$), —N($R^{14}$)S(=O)$_2$N($R^{13}$)($R^{14}$), —N($R^{14}$)S(=O)$_2$($R^{13}$), —S(=O)$_2$N($R^{13}$)($R^{14}$), $C_1$–$C_4$ alkyl, $C_2$–$C_4$ alkenyl, $C_3$–$C_{10}$ cycloalkyl, $C_3$–$C_6$ cycloalkylmethylene, $C_7$–$C_{10}$ arylalkyl, $C_3$–$C_6$ cycloalkoxy, $C_1$–$C_4$ alkyl substituted with —N($R^{13}$)($R^{14}$), $C_1$–$C_4$ hydroxyalkyl, $C_1$–$C_4$ haloalkyl, $C_1$–$C_4$haloalkoxy, $C_1$–$C_4$ alkoxycarbonyl, $C_1$–$C_4$alkylcarbonyloxy, $C_1$–$C_4$ alkylcarbonyl, $C_1$–$C_4$ alkylcarbonylamino, 2-(1-morpholino)ethoxy, -($C_1$–$C_3$ alkyl) aryl substituted with 0–2 $R^{12}$ a $C_5$–$C_{14}$ carbocyclic residue substituted with 0–3 $R^{12}$ or a 5- to 10-membered heterocyclic ring system containing 1 to 4 heteroatoms independently selected from oxygen, nitrogen or sulfur, the heterocyclic ring system being substituted with 0–3 $R^{12}$; and 1–3 amino acids linked together via amide bonds, and linked to $R^4$ $R^7$ $R^{20}$, or $R^{21}$ via the amine or carboxylate terminus;

m is: 0, 1 or 2;

each $R^{11A}$ is independently:
H, keto, halogen, cyano, —CH$_2$NH$_2$, —NH$_2$, —C(=O)OH, —OC(=O)($C_1$–$C_3$ alkyl), —OH, $C_2$–$C_6$ alkoxyalkyl, —C(=O)NH$_2$, —OC(=O)NH$_2$, —NHC(=O)NH$_2$, —S(=O)$_2$NH$_2$, $C_1$–$C_4$ alkyl, $C_2$–$C_4$ alkenyl, $C_3$–$C_{10}$ cycloalkyl, $C_3$–$C_6$ cycloalkylmethylene, benzyl, phenethyl, phenoxy, benzyloxy, nitro, $C_7$–$C_{10}$ arylalkyl, hydroxamic acid, hydrazide, boronic acid, $C_3$–$C_6$ cycloalkoxy, $C_1$–$C_4$ alkyl substituted with —NH$_2$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —OCH$_2$C(=O)OH, 2-(1-morpholino)ethoxy, azido, aryl ($C_1$–$C_3$ alkyl), a $C_5$–$C_{14}$ carbocyclic residue, or a 5- to 10-membered heterocyclic ring system containing 1 to 4 heteroatoms independently selected from oxygen, nitrogen or sulfur;

each $R^{12}$ when a substituent on carbon, is independently:
phenyl, phenylmethyl, phenethyl, phenoxy, phenylmethoxy, halogen, hydroxy, nitro, cyano, $C_1$–$C_4$ alkyl, $C_3$–$C_6$ cycloalkyl, $C_3$–$C_6$ cycloalkylmethylene, $C_7$–$C_{10}$ arylalkyl, $C_1$–$C_4$ alkoxy, —C(=O)OH, hydroxamic acid, hydrazide, boronic acid, sulfonamide, formyl, $C_3$–$C_6$ cycloalkoxy, —O($R^{13}$), $C_1$–$C_4$ alkyl substituted with —N($R^{13}$)($R^{14}$), —N($R^{13}$)($R^{14}$), $C_2$–$C_6$ alkoxyalkyl, $C_1$–$C_4$ hydroxyalkyl, methylenedioxy, ethylenedioxy, $C_1$–$C_4$ haloalkyl, $C_1$–$C_4$haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —S(=O)$_m$($R^{13}$), —S(=O)$_2$N($R^{13}$)($R^{14}$), —NHS(=O)$_2$($R^{14}$), —OCH$_2$C(=O)OH, 2-(1-morpholino)ethoxy, —C($R^{14}$)=N—O($R^{14}$), a 5- to 10-membered heterocyclic ring containing from 1 to 4 heteroatoms independently selected from oxygen, nitrogen or sulfur, the heterocyclic ring system being substituted with 0–3 $R^{15}$, a 3- or 4-carbon aliphatic chain attached to an adjacent carbon on the ring to which it is appended to form a fused 5- or 6-membered ring, the 5- or 6-membered ring being optionally substituted on any of the aliphatic carbons with halogen, $C_1$–$C_4$ alkyl, $C_1$–$C_4$ alkoxy, hydroxy, —N($R^{13}$)($R^{14}$), or when $R^{12}$ is a substituent on a saturated carbon atom, $R^{12}$ may alternatively be =O or =S;

each $R^{12}$ when a substituent on nitrogen, is independently:
phenyl, phenylmethyl, phenethyl, hydroxy, $C_1$–$C_4$ hydroxyalkyl, $C_1$–$C_4$ alkoxy, $C_1$–$C_4$ alkyl, $C_3$–$C_6$cycloalkyl, $C_3$–$C_6$ cycloalkylmethylene, —CH$_2$N($R^{13}$)($R^{14}$), —N($R^{13}$)($R^{14}$), $C_2$–$C_6$ alkoxyalkyl, $C_1$–$C_4$ haloalkyl, $C_1$–$C_4$alkoxycarbonyl, —C(=O)OH, $C_1$–$C_4$ alkylcarbonyloxy, $C_1$–$C_4$ alkylcarbonyl or —C($R^{14}$)=N—O($R^{14}$);

each $R^{13}$ is independently:
hydrogen,
phenyl substituted with 0–3 $R^{11A}$,
phenylmethyl substituted with 0–3 $R^{11A}$,
$C_1$–$C_6$ alkyl substituted with 0–3 $R^{11A}$,
$C_2$–$C_4$ alkenyl substituted with 0–3 $R^{11A}$,
$C_1$–$C_6$ alkylcarbonyl substituted with 0–3 $R^{11A}$,
$C_1$–$C_6$ alkoxycarbonyl substituted with 0–3 $R^{11A}$,
$C_1$–$C_6$ alkylaminocarbonyl substituted with 0–3 $R^{11A}$,
$C_3$–$C_6$ alkoxyalkyl substituted with 0–3 $R^{11A}$,
an amine protecting group when $R^{13}$ is bonded to N, or
a hydroxy protecting group when $R^{13}$ is bonded to O;

each $R^{14}$ is independently:
hydrogen, hydroxy, trifluoromethyl, $C_1$–$C_6$ alkoxy, $C_2$–$C_6$ alkenyl, phenylmethyl, amino,
$C_1$–$C_6$ alkyl substituted with 0–3 groups selected from hydroxy, $C_1$–$C_4$ alkoxy, halogen or amino,
an amine protecting group when $R^{14}$ is bonded to N, or
a hydroxy protecting group when $R^{14}$ is bonded to O;

$R^{13}$ and $R^{14}$ can alternatively join to form:
—(CH$_2$)$_4$—, —(CH$_2$)$_5$—, —CH$_2$CH$_2$N($R^{15}$)CH$_2$CH$_2$— or —CH$_2$CH$_2$OCH$_2$CH$_2$—;

$R^{15}$ is: hydrogen or methyl;

each of $R^{20}$ and $R^{21}$ is independently:
- hydrogen,
- $C_1$–$C_6$ alkyl substituted with 0–3 $R^{11}$,
- $C_3$–$C_6$ alkoxyalkyl substituted with 0–3 $R^{11}$,
- $C_1$–$C_6$ alkylcarbonyl substituted with 0–3 $R^{11}$,
- $C_1$–$C_6$ alkoxycarbonyl substituted with 0–3 $R^{11}$,
- $C_1$–$C_6$ alkylaminocarbonyl substituted with 0–3 $R^{11}$
- benzoyl substituted with 0–3 $R^{12}$,
- phenoxycarbonyl substituted with 0–3 $R^{12}$,
- phenylaminocarbonyl substituted with 0–3 $R^{12}$,
- or any group that, when administered to a mammalian subject as part of a compound of Formula (I), cleaves to form a free hydroxyl, free amino or free sulfhydryl;

each of $R^{22}$ and $R^{23}$ is independently:
- hydrogen,
- $C_1$–$C_8$ alkyl substituted with 0–3 $R^{31}$,
- $C_2$–$C_8$ alkenyl substituted with 0–3 $R^{31}$,
- $C_2$–$C_8$ alkynyl substituted with 0–3 $R^{31}$,
- a $C_3$–$C_{14}$ carbocyclic ring system substituted with 0–5 $R^{31}$ or 0–5 $R^{32}$ or
- a 5- to 10-membered heterocyclic ring system containing 1 to 4 heteroatoms independently selected from oxygen, nitrogen or sulfur, the heterocyclic ring system being substituted with 0–2 $R^{32}$;

alternatively, $R^{22}$ can join with $R^4$ or $R^{4A}$ to form a 5- or 6-membered fused heterocyclic ring or carbocyclic ring substituted with 0–2 $R^{12}$, the heterocyclic ring containing 1–3 heteroatoms independently selected from nitrogen, sulfur or oxygen;

alternatively, $R^{23}$ can join with $R^7$ or $R^{7A}$ to form a 5- or 6-membered fused heterocyclic ring or carbocyclic ring substituted with 0–2 $R^{12}$, the heterocyclic ring containing 1–3 heteroatoms independently selected from nitrogen, sulfur or oxygen;

alternatively, $R^{22}$ or $R^{23}$ can join with $R^5$ or $R^6$ to form a 0- to 7- membered bridge to form a carbocyclic or heterocyclic ring, said bridge being substituted with 0–2 $R^{12}$ and the bridge containing 0–3 heteroatoms independently selected from nitrogen, sulfur or oxygen;

alternatively, the atoms to which $R^{22}$ and $R^{4A}$ are appended may be joined together with a double bond;

alternatively, the atoms to which $R^{23}$ and $R^{7A}$ are appended may be joined together with a double bond;

Z is: O or S;

each $R^{31}$ is independently:
- keto, halogen, cyano, —$CH_2N(R^{13})(R^{14})$, —$N(R^{13})(R^{14})$, —$C(=O)O(R^{13})$, —$C(=O)(R^{11})$, —$OC(=O)(R^{13})$, —$O(R^{13})$, $C_2$–$C_6$ alkoxyalkyl, —$S(=O)_m(R^{13})$, —$NHC(=NH)NH(R^{13})$, —$C(=NH)NH(R^{13})$, —$C(=O)N(R^{13})(R^{14})$, —$N(R^{14})C(=O)(R^{13})$, =$N$—$O(R^{14})$, —$N(R^{14})C(=O)O(R^{14})$, —$OC(=O)N(R^{13})(R^{14})$, —$N(R^{13})C(=O)N(R^{13})(R^{14})$, —$N(R^{14})S(=O)_2N(R^{13})(R^{14})$, —$N(R^{14})S(=O)_2(R^{13})$, —$S(=O)_2N(R^{13})(R^{14})$, $C_1$–$C_4$ alkyl, $C_2$–$C_4$ alkenyl, $C_3$–$C_{10}$ cycloalkyl, $C_3$–$C_6$ cycloalkylmethylene, phenylmethyl, phenethyl, phenoxy, phenylmethoxy, nitro, $C_7$–$C_{10}$ arylalkyl, hydroxamic acid, hydrazide, oxime, boronic acid, sulfonamide, formyl, $C_3$–$C_6$ cycloalkoxy, $C_1$–$C_4$ alkyl substituted with —$N(R^{13})(R^{14})$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$OCH_2C(=O)O(R^{13})$, 2-(1-morpholino)ethoxy, azido, —$C(R^{14})=N$—$O(R^{14})$,
- a $C_5$–$C_{14}$ carbocyclic residue substituted with 0–5 $R^{32}$,
- a 5- to 10-membered heterocyclic ring system containing 1 to 4 heteroatoms independently selected from oxygen, nitrogen or sulfur, the heterocyclic ring system being substituted with 0–2 $R^{32}$ or
- 1–3 amino acids, linked together via amide bonds, and linked to $R^{22}$ or $R^{23}$ via the amine or carboxylate terminus;

each $R^{32}$ when a substituent on carbon, is independently:
- phenethyl, phenoxy, $C_3$–$C_{10}$ cycloalkyl, $C_3$–$C_6$ cycloalkylmethylene, $C_7$–$C_{10}$ arylalkyl, hydrazide, oxime, $C_2$–$C_6$ alkoxyalkyl, methylenedioxy, ethylenedioxy, $C_1$–$C_4$ alkylcarbonyloxy, —$NHS(=O)_2(R^{14})$, phenylmethoxy, halogen, 2-(1-morpholino)ethoxy, —$C(=O)O(R^{13})$, hydroxamic acid, —$C(=O)N(R^{13})N(R^{13})(R^{14})$, cyano, boronic acid, sulfonamide, formyl, $C_3$–$C_6$ cycloalkoxy, $C_1$–$C_4$ haloalkyl, $C_1$–$C_4$ haloalkoxy, $C_2$–$C_4$ haloalkenyl, $C_2$–$C_4$ haloalkynyl, —$N(R^{13})(R^{14})$, —$C(R^{14})=N$—$O(R^{14})$, —$NO_2$, —$O(R^{13})$, —$N(R^{40})(R^{41})$, —$S(=O)_m(R^{13})$, —$S(=O)_mN(R^{13})(R^{14})$, —$C(=O)N(R^{13})(R^{14})$, —$OC(=O)N(R^{13})(R^{14})$, —$C(=O)(R^{11})$, —$OC(=O)(R^{11})$, —$OC(=O)O(R^{13})$, phenyl, —$C(=O)N(R^{13})$—$(C_1$–$C_4$ alkyl)-$N(R^{13})(R^{14})$, —$C(=O)N(R^{40})(R^{41})$, —$C(=O)N(R^{13})C(R^{11})_2N(R^{13})(R^{14})$, —$C(=O)N(R^{13})C(R^{11})_2N(R^{13})NH(R^{14})$, —$C(=O)N(R^{13})C(R^{11})_2N(R^{13})C(=O)O(R^{13})$, —$C(=O)N(R^{13})$—$(C_1$–$C_4$ alkyl)-$N(R^{13})C(=O)O(R^{13})$, —$C(=O)N(R^{13})$—$(C_1$–$C_4$ alkyl)-$R^{11}$, —$C(=O)C(R^{11})_2N(R^{13})(R^{14})$, —$C(=O)C(R^{11})_2N(R^{13})NH(R^{14})$, —$C(=O)C(R^{11})_2N(R^{13})C(=O)O(R^{13})$, —$C(=O)$—$(C_1$–$C_4$ alkyl)—$N(R^{13})(R^{14})$, —$C(=O)$—$(C_1$–$C_4$ alkyl) —$N(R^{13})C(=O)O(R^{13})$,
- $C_1$–$C_4$ alkoxy substituted with 0–4 groups selected from: $R^{11}$ $C_3$–$C_6$ cycloalkyl, —$C(=O)O(R^{13})$, —$C(=O)N(R^{13})(R^{14})$, —$N(R^{13})(R^{14})$ or hydroxyl,
- $C_1$–$C_4$ alkyl substituted with 0–4 groups selected from: $R^{11}$ =$N(R^{14})$, =$NN(R^{13})C(=O)N(R^{13})(R^{14})$ or —$N(R^{13})(R^{14})$,
- $C_2$–$C_4$ alkenyl substituted with 0–4 $R^{11}$,
- $C_2$–$C_4$ alkynyl substituted with 0–4 $R^{11}$,
- a 5- or 6-membered heterocyclic ring containing from 1 to 4 heteroatoms independently selected from oxygen, nitrogen or sulfur,
- a 3- or 4-carbon aliphatic chain attached to an adjacent carbon on the ring to which it is appended, to form a fused 5- or 6-membered ring, the 5- or 6-membered ring being optionally substituted on the aliphatic carbons with halogen, $C_1$–$C_4$ alkyl, $C_1$–$C_4$ alkoxy, hydroxyl—$N(R^{13})(R^{14})$, or
- when $R^{32}$ is attached to a saturated carbon atom, $R^{32}$ may be =O or =S;

each $R^{32}$ when a substituent on nitrogen, is independently:
- phenyl, phenylmethyl, phenethyl, hydroxyl, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethylene, —$CH_2N(R^{13})(R^{14})$, —$N(R^{13})(R^{14})$, $C_2$–$C_6$ alkoxyalkyl, $C_1$–$C_4$ haloalkyl, $C_1$–$C_4$ alkoxycarbonyl, —$C(=O)OH$, $C_1$–$C_4$ alkylcarbonyloxy, $C_1$–$C_4$ alkylcarbonyl or —$C(R^{14})=N$—$O(R^{14})$;

$R^{40}$ is: hydrogen or $C_1$–$C_3$ alkyl;

$R^{41}$ is: —C(=O)N($R^{13}$)($R^{14}$), —C(=O)N($R^{13}$)NH($R^{14}$), —C(=O)C($R^{11}$)$_2$N($R^{13}$)($R^{14}$), —C(=O)C($R^{11}$)$_2$N($R^{13}$)NH($R^{14}$), —C(=O)C($R^{11}$)$_2$N($R^{13}$)C(=O)O($R^{13}$), —C(=O) H, —C(=O)($R^{11}$), —C(=O)—($C_1$–$C_4$ alkyl)—N($R^{13}$)($R^{14}$), —C(=O)—($C_1$–$C_4$ alkyl)—N($R^{13}$)C(=O)O($R^{13}$) or 1–3 amino acids linked together via amide bonds and linked to the N atom via the carboxylate terminus; and n is: 0, 1 or 2;
provided that:

$R^4$, $R^{4A}$, $R^7$ and $R^{7A}$ are not all hydrogen;

when $R^4$ and $R^{4A}$ are both hydrogen, $R^{22}$ is not hydrogen, and when $R^7$ and $R^{7A}$ are both hydrogen, $R^{23}$ is not hydrogen.

66. The method according to claim 65, wherein step (a) comprises reacting a compound of Formula (IIb) with either carbonyl diimidazole, thereby forming a cyclic urea of Formula (Ib) having Z=O, or thiocarbonyl diimidazole, thereby forming a cyclic urea of Formula (Ib) having Z=S.

67. The method according to claim 65, wherein the aqueous acid solution of step (b)(i) is an aqueous hydrochloric acid, nitric acid, phosphoric acid or citric acid solution.

68. The method according to claim 65, wherein the aqueous acid solution of step (b)(i) is an aqueous citric acid solution.

69. A method for converting a compound of Formula (IIa) to a compound of Formula (IIb) by any of direct alkylation, reductive amination, or successive acylation and reduction, wherein, the compound of Formula (IIa) has the structure shown in Formula (II) with the proviso that $R^{22}$ and $R^{23}$ are hydrogen, the compound of Formula (IIb) has the structure shown in Formula (II) with the proviso that only one of $R^{22}$ or $R^{23}$ is hydrogen, compound (II) has a Formula:

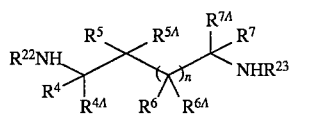

(II)

wherein, each of $R^4$ and $R^7$ is independently:

hydrogen, —O($R^{13}$), —S($R^{13}$), —C(=O)O($R^{13}$), $C_1$–$C_8$ alkyl substituted with 0–3 $R^{11}$, $C_2$–$C_8$ alkenyl substituted with 0–3 $R^{11}$, $C_2$–$C_8$ alkynyl substituted with 0–3 $R^{11}$, a $C_3$–$C_{14}$ carbocyclic ring system substituted with 0–3 $R^{11}$ or 0–3 $R^{12}$ or a 5- to 10-membered heterocyclic ring system containing 1 to 4 heteroatoms independently selected from oxygen, nitrogen or sulfur, the heterocyclic ring system being substituted with 0–2 $R^{12}$;

each of $R^{4A}$ and $R^{7A}$ is independently:

hydrogen, —O($R^{13}$), —S($R^{13}$), —C(=O)O($R^{13}$), $C_1$–$C_4$ alkyl unsubstituted or substituted with halogen or $C_1$–$C_2$ alkoxy, or phenylmethyl unsubstituted or substituted with halogen or $C_1$–$C_2$ alkoxy;

$R^4$ and $R^{4A}$ can alternatively join to form a 5- to 7-membered carbocyclic ring substituted with 0–2 $R^{12}$;

$R^7$ and $R^{7A}$ can alternatively join to form a 5- to 7-membered carbocyclic ring substituted with 0–2 $R^{12}$;

each of $R^5$ and $R^{5A}$ is independently:

hydrogen, halogen, —N($R^{20}$)$_2$, —S($R^{20}$), —O($R^{20}$) or $C_1$–$C_6$ alkyl substituted with 0–3 $R^{11}$;

$R^5$ and $R^{5A}$ can alternatively join together to form a =O, =S or a ketal ring;

each of $R^6$ and $R^{6A}$ is independently:

hydrogen, halogen, —N($R^{20}$)$_2$, —S($R^{20}$), —O($R^{21}$) or $C_1$–$C_6$ alkyl substituted with 0–3 $R^{11}$;

$R^6$ and $R^{6A}$ can alternatively join together to form a =O, =S or a ketal ring;

$R^5$ and $R^6$ can alternatively join together to form an epoxide or aziridine ring; —OCH$_2$SCH$_2$O—, —OS(=O)O—, —OC(=O)O—, —OCH$_2$O—, —OC(=S)O—, —OC(=O)C(=O)O—, —OC(CH$_3$)$_2$O—, —OC((CH$_2$)$_3$NH$_2$)(CH$_3$)O—, —OC(OCH$_3$)(CH$_2$CH$_2$CH$_3$)O—, —OS(=O)$_2$O—, —NHC(=O)NH—, —OC(=O)NH—, —NHC(=O)O—, —NHCH$_2$O—, —OCH$_2$NH—, —NHC(=S)O—, —OC(=S)NH—, —OS(=O)NH—, —NHS(=O)O—, —NHC(=O)C(=O)O—, —OC(=O)C(=O)NH—, —NHC(=O)C(=O)NH—, —NHC(CH$_3$)$_2$O—, —OC(CH$_3$)$_2$NH— or any group that, when administered to a mammalian subject as part of a compound of Formula (I), cleaves to form a compound having two free hydroxyl groups, or two free amino groups, or one free hydroxyl group and one free amino group;

each $R^{11}$ is independently:

hydrogen, keto, halogen, cyano, phenylmethyl, phenethyl, methylenedioxy, ethylenedioxy, hydroxamic acid, hydrazide, boronic acid, sulfonamide, azido, formyl, phenoxy, phenylmethoxy, nitro, —CH$_2$N($R^{13}$)($R^{14}$), —N($R^{13}$)($R^{14}$), —OCH$_2$C(=O)OH, —C(=O)O($R^{13}$), —OC(=O)($R^{13}$), —O($R^{13}$), $C_2$–$C_6$ alkoxyalkyl, —S(=O)$_m$($R^{13}$), —NHC(=NH)NH($R^{13}$), —C(=NH)NH($R^{13}$), —C(=O)N($R^{13}$)($R^{14}$), —N($R^{14}$)C(=O)($R^{13}$), =N—O($R^{14}$), —N($R^{14}$)C(=O)O($R^{14}$), —OC(=O)N($R^{13}$)($R^{14}$), —N($R^{13}$)C(=O)N($R^{13}$)($R^{14}$), —C($R^{14}$)=N—O($R^{14}$), —N($R^{14}$)S(=O)$_2$N($R^{13}$)($R^{14}$), —N($R^{14}$)S(=O)$_2$($R^{13}$), —S(=O)$_2$N($R^{13}$)($R^{14}$), $C_1$–$C_4$ alkyl, $C_2$–$C_4$ alkenyl, $C_3$–$C_{10}$ cycloalkyl, $C_3$–$C_6$ cycloalkylmethylene, $C_7$–$C_{10}$ arylalkyl, $C_3$–$C_6$ cycloalkoxy, $C_1$–$C_4$ alkyl substituted with —N($R^{13}$)($R^{14}$), $C_1$–$C_4$ hydroxyalkyl, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, 2-(1-morpholino)ethoxy, —($C_1$–$C_3$ alkyl) aryl substituted with 0–2 $R^{12}$, a $C_5$–$C_{14}$ carbocyclic residue substituted with 0–3 $R^{12}$ or a 5- to 10-membered heterocyclic ring system containing 1 to 4 heteroatoms independently selected from oxygen, nitrogen or sulfur, the heterocyclic ring system being substituted with 0–3 $R^{12}$; and 1–3 amino acids linked together via amide bonds, and linked to $R^4$ $R^7$ $R^{20}$ or $R^{21}$ via the amine or carboxylate terminus;

m is: 0, 1 or 2;

each $R^{11A}$ is independently:

H, keto, halogen, cyano, —CH$_2$NH$_2$, —NH$_2$, —C(=O)OH, —OC(=O)($C_1$–$C_3$ alkyl), —OH, $C_2$–$C_6$ alkoxyalkyl, —C(=O)NH$_2$, —OC(=O)NH$_2$, —NHC(=O)NH$_2$, —S(=O)$_2$NH$_2$, $C_1$–$C_4$ alkyl, $C_2$–$C_4$ alkenyl, $C_3$–$C_{10}$ cycloalkyl, $C_3$–$C_6$ cycloalkylmethylene, benzyl, phenethyl, phenoxy, benzyloxy, nitro, $C_7$–$C_{10}$ arylalkyl, hydroxamic acid, hydrazide, boronic acid, $C_3$–$C_6$ cycloalkoxy, $C_1$–$C_4$ alkyl substituted with —$NH_2$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$OCH_2C(=O)OH$, 2-(1-morpholino)ethoxy, azido, aryl ($C_1$–$C_3$ alkyl), a $C_5$–$C_{14}$ carbocyclic residue, or a 5- to 10-membered heterocyclic ring system containing 1 to 4 heteroatoms independently selected from oxygen, nitrogen or sulfur;

each $R^{12}$ when a substituent on carbon, is independently:

phenyl, phenylmethyl, phenethyl, phenoxy, phenylmethoxy, halogen, hydroxy, nitro, cyano, $C_1$–$C_4$ alkyl, $C_3$–$C_6$ cycloalkyl, $C_3$–$C_6$ cycloalkylmethylene, $C_7$–$C_{10}$ arylalkyl, $C_1$–$C_4$ alkoxy, —$C(=O)OH$, hydroxamic acid, hydrazide, boronic acid, sulfonamide, formyl, $C_3$–$C_6$ cycloalkoxy, —$O(R^{13})$, $C_1$–$C_4$ alkyl substituted with —$N(R^{13})(R^{14})$, —$N(R^{13})(R^{14})$, $C_2$–$C_6$ alkoxyalkyl, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —$S(=O)_m(R^{13})$, —$S(=O)_2N(R^{13})(R^{14})$, —$NHS(=O)_2(R^{14})$, —$OCH_2C(=O)OH$, 2-(1-morpholino)ethoxy, —$C(R^{14})=N$—$O(R^{14})$, a 5- to 10-membered heterocyclic ring containing from 1 to 4 heteroatoms independently selected from oxygen, nitrogen or sulfur, the heterocyclic ring system being substituted with 0–3 $R^{15}$, a 3- or 4-carbon aliphatic chain attached to an adjacent carbon on the ring to which it is appended to form a fused 5- or 6-membered ring, the 5- or 6-membered ring being optionally substituted on any of the aliphatic carbons with halogen, $C_1$–$C_4$ alkyl, $C_1$–$C_4$ alkoxy, hydroxy, —$N(R^{13})(R^{14})$, or when $R^{12}$ is a substituent on a saturated carbon atom, $R^{12}$ may alternatively be =O or =S;

each $R^{12}$ when a substituent on nitrogen, is independently:

phenyl, phenylmethyl, phenethyl, hydroxy, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethylene, —$CH_2N(R^{13})(R^{14})$, —$N(R^{13})(R^{14})$, $C_2$–$C_6$ alkoxyalkyl, $C_1$–$C_4$ haloalkyl, $C_1$–$C_4$ alkoxycarbonyl, —$C(=O)OH$, $C_1$–$C_4$ alkylcarbonyloxy, $C_1$–$C_4$ alkylcarbonyl or —$C(R^{14})=N$—$O(R^{14})$;

each $R^{13}$ is independently:

hydrogen, phenyl substituted with 0–3 $R^{11A}$, phenylmethyl substituted with 0–3 $R^{11A}$, $C_1$–$C_6$ alkyl substituted with 0–3 $R^{11A}$, $C_2$–$C_4$ alkenyl substituted with 0–3 $R^{11A}$, $C_1$–$C_6$ alkylcarbonyl substituted with 0–3 $R^{11A}$, $C_1$–$C_6$ alkoxycarbonyl substituted with 0–3 $R^{11A}$, $C_1$–$C_6$ alkylaminocarbonyl substituted with 0–3 $R^{11A}$, $C_3$–$C_6$ alkoxyalkyl substituted with 0–3 $R^{11A}$, an amine protecting group when $R^{13}$ is bonded to N, or a hydroxy protecting group when $R^{13}$ is bonded to O;

each $R^{14}$ is independently:

hydrogen, hydroxy, trifluoromethyl, $C_1$–$C_6$ alkoxy, $C_2$–$C_6$ alkenyl, phenylmethyl, amino, $C_1$–$C_6$ alkyl substituted with 0–3 groups selected from hydroxy, $C_1$–$C_4$ alkoxy, halogen or amino, an amine protecting group when $R^{14}$ is bonded to N, or a hydroxy protecting group when $R^{14}$ is bonded to O;

$R^{13}$ and $R^{14}$ can alternatively join to form:

—$(CH_2)_4$—, —$(CH_2)_5$—, —$CH_2CH_2N(R^{15})CH_2CH_2$— or —$CH_2CH_2OCH_2CH_2$—;

$R^{15}$ is: hydrogen or methyl;

each of $R^{20}$ and $R^{21}$ is independently:

hydrogen, $C_1$–$C_6$ alkyl substituted with 0–3 $R^{11}$, $C_3$–$C_6$ alkoxyalkyl substituted with 0–3 $R^{11}$, $C_1$–$C_6$ alkylcarbonyl substituted with 0–3 $R^{11}$, $C_1$–$C_6$ alkoxycarbonyl substituted with 0–3 $R^{11}$, $C_1$–$C_6$ alkylaminocarbonyl substituted with 0–3 $R^{11}$, benzoyl substituted with 0–3 $R^{12}$, phenoxycarbonyl substituted with 0–3 $R^{12}$, phenylaminocarbonyl substituted with 0–3 $R^{12}$, or any group that, when administered to a mammalian subject as part of a compound of Formula (I), cleaves to form a free hydroxyl, free amino or free sulfhydryl;

each of $R^{22}$ and $R^{23}$ is independently:

hydrogen, $C_1$–$C_8$ alkyl substituted with 0–3 $R^{31}$, $C_2$–$C_8$ alkenyl substituted with 0–3 $R^{31}$, $C_2$–$C_8$ alkynyl substituted with 0–3 $R^{31}$, a $C_3$–$C_{14}$ carbocyclic ring system substituted with 0–5 $R^{31}$ or 0–5 $R^{32}$, or a 5- to 10-membered heterocyclic ring system containing 1 to 4 heteroatoms independently selected from oxygen, nitrogen or sulfur, the heterocyclic ring system being substituted with 0–2 $R^{32}$;

alternatively, $R^{22}$ can join with $R^4$ or $R^{4A}$ to form a 5- or 6-membered fused heterocyclic ring or carbocyclic ring substituted with 0–2 $R^{12}$, the heterocyclic ring containing 1–3 heteroatoms independently selected from nitrogen, sulfur or oxygen;

alternatively, $R^{23}$ can join with $R^7$ or $R^{7A}$ to form a 5- or 6-membered fused heterocyclic ring or carbocyclic ring substituted with 0–2 $R^{12}$, the heterocyclic ring containing 1–3 heteroatoms independently selected from nitrogen, sulfur or oxygen;

alternatively, $R^{22}$ or $R^{23}$ can join with $R^5$ or $R^6$ to form a 0- to 7- membered bridge to form a carbocyclic or heterocyclic ring, said bridge being substituted with 0–2 $R^{12}$ and the bridge containing 0–3 heteroatoms independently selected from nitrogen, sulfur or oxygen;

alternatively, the atoms to which $R^{22}$ and $R^{4A}$ are appended may be joined together with a double bond;

alternatively, the atoms to which $R^{23}$ and $R^{7A}$ are appended may be joined together with a double bond;

Z is: O or S;

each $R^{31}$ is independently:

keto, halogen, cyano, —$CH_2N(R^{13})(R^{14})$, —$N(R^{13})(R^{14})$, —$C(=O)O(R^{13})$, —$C(=O)(R^{11})$, —$OC(=O)(R^{13})$, —$O(R^{13})$, $C_2$–$C_6$ alkoxyalkyl, —$S(=O)_m(R^{13})$, —$NHC(=NH)NH(R^{13})$, —$C(=NH)NH(R^{13})$, —$C(=O)N(R^{13})(R^{14})$, —$N(R^{14})C(=O)(R^{13})$, =N—$O(R^{14})$, —$N(R^{14})C(=O)O(R^{14})$, —$OC(=O)N(R^{13})(R^{14})$, —$N(R^{13})C(=O)N(R^{13})(R^{14})$, —$N(R^{14})S(=O)_2N(R^{13})(R^{14})$, —$N(R^{14})S(=O)_2(R^{13})$, —$S(=O)_2N(R^{13})(R^{14})$, $C_1$–$C_4$ alkyl, $C_2$–$C_4$ alkenyl, $C_3$–$C_{10}$ cycloalkyl, $C_3$–$C_6$ cycloalkylmethylene, phenylmethyl, phenethyl, phenoxy, phenylmethoxy, nitro, $C_7$–$C_{10}$ arylalkyl, hydroxamic acid, hydrazide, oxime, boronic acid, sulfonamide, formyl, $C_3$–$C_6$ cycloalkoxy, $C_1$–$C_4$ alkyl substituted with —$N(R^{13})(R^{14})$, $C_1$–$C_4$ hydroxyalkyl, methylenedioxy, ethylenedioxy, $C_1$–$C_4$ haloalkyl, $C_1$–$C_4$ haloalkoxy, $C_1$–$C_4$ alkoxycarbonyl, $C_1$–$C_4$ alkylcarbonyloxy, $C_1$–$C_4$ alkylcarbonyl, $C_1$–$C_4$ alkylcarbonylamino, —OCH$_2$C(=O)O(R$^{13}$), 2-(1-morpholino)ethoxy, azido, —C(R$^{14}$)=N—O(R$^{14}$), a $C_5$–$C_{14}$ carbocyclic residue substituted with 0–5 R$^{32}$, a 5- to 10-membered heterocyclic ring system containing 1 to 4 heteroatoms independently selected from oxygen, nitrogen or sulfur, the heterocyclic ring system being substituted with 0–2 R$^{32}$, or 1–3 amino acids, linked together via amide bonds, and linked to R$^{22}$ or R$^{23}$ via the amine or carboxylate terminus;

each R$^{32}$, when a substituent on carbon, is independently:

phenethyl, phenoxy, $C_3$–$C_{10}$ cycloalkyl, $C_3$–$C_6$ cycloalkylmethylene, $C_7$–$C_{10}$ arylalkyl, hydrazide, oxime, $C_2$–$C_6$ alkoxyalkyl, methylenedioxy, ethylenedioxy, $C_1$–$C_4$ alkylcarbonyloxy, —NHS(=O)$_2$(R$^{14}$), phenylmethoxy, halogen, 2-(1-morpholino)ethoxy, —C(=O)O(R$^{13}$), hydroxamic acid, —C(=O)N(R$^{13}$)N(R$^{13}$)(R$^{14}$), cyano, boronic acid, sulfonamide, formyl, $C_3$–$C_6$ cycloalkoxy, $C_1$–$C_4$ haloalkyl, $C_1$–$C_4$ haloalkoxy, $C_2$–$C_4$ haloalkenyl, $C_2$–$C_4$ haloalkynyl, —N(R$^{13}$)(R$^{14}$), —C(R$^{14}$)=N—O(R$^{14}$), —NO$_2$, —O(R$^{13}$), —N(R$^{40}$)(R$^{41}$), —S(=O)$_m$(R$^{13}$), —S(=O)$_m$N(R$^{13}$)(R$^{14}$), —C(=O)N(R$^{13}$)(R$^{14}$), —OC(=O)N(R$^{13}$)(R$^{14}$), —C(=O)(R$^{11}$), —OC(=O)(R$^{11}$), —OC(=O)O(R$^{13}$), phenyl, —C(=O)N(R$^{13}$)—($C_1$–$C_4$ alkyl)-N(R$^{13}$)(R$^{14}$), —C(=O)N(R$^{40}$)(R$^{41}$), —C(=O)N(R$^{13}$)C(R$^{11}$)$_2$N(R$^{13}$)(R$^{14}$), —C(=O)N(R$^{13}$)C(R$^{11}$)$_2$N(R$^{13}$)NH(R$^{14}$), —C(=O)N(R$^{13}$)C(R$^{11}$)$_2$N(R$^{13}$)C(=O)O(R$^{13}$), —C(=O)N(R$^{13}$)—($C_1$–$C_4$ alkyl)—N(R$^{13}$)C(=O)O(R$^{13}$), —C(=O)N(R$^{13}$)—($C_1$–$C_4$ alkyl)—R$^{11}$, —C(=O)C(R$^{11}$)$_2$N(R$^{13}$)(R$^{14}$), —C(=O)C(R$^{11}$)$_2$N(R$^{13}$)NH(R$^{14}$), —C(=O)C(R$^{11}$)$_2$N(R$^{13}$)C(=O)O(R$^{13}$), —C(=O)—($C_1$–$C_4$ alkyl) —N(R$^{13}$)(R$^{14}$), —C(=O)—($C_1$–$C_4$ alkyl) —N(R$^{13}$)C(=O)O(R$^{13}$), $C_1$–$C_4$ alkoxy substituted with 0–4 groups selected from: R$^{11}$, $C_3$–$C_6$ cycloalkyl, —C(=O)O(R$^{13}$), —C(=O)N(R$^{13}$)(R$^{14}$), —N(R$^{13}$)(R$^{14}$) or hydroxyl, $C_1$–$C_4$ alkyl substituted with 0–4 groups selected from: R$^{11}$, =N(R$^{14}$), =NN(R$^{13}$)C(=O)N(R$^{13}$)(R$^{14}$) or —N(R$^{13}$)(R$^{14}$), $C_2$–$C_4$ alkenyl substituted with 0–4 R$^{11}$, $C_2$–$C_4$ alkynyl substituted with 0–4 R$^{11}$, a 5- or 6-membered heterocyclic ring containing from 1 to 4 heteroatoms independently selected from oxygen, nitrogen or sulfur, a 3- or 4-carbon aliphatic chain attached to an adjacent carbon on the ring to which it is appended, to form a fused 5- or 6-membered ring, the 5- or 6-membered ring being optionally substituted on the aliphatic carbons with halogen, $C_1$–$C_4$ alkyl, $C_1$–$C_4$ alkoxy, hydroxyl —N(R$^{13}$)(R$^{14}$), or when R$^{32}$, is attached to a saturated carbon atom, R$^{32}$ may be =O or =S;

each R$^{32}$ when a substituent on nitrogen, is independently:

phenyl, phenylmethyl, phenethyl, hydroxyl, $C_1$–$C_4$ hydroxyalkyl, $C_1$–$C_4$ alkoxy, $C_1$–$C_4$ alkyl, $C_3$–$C_6$ cycloalkyl, $C_3$–$C_6$ cycloalkylmethylene, —CH$_2$N(R$^{13}$)(R$^{14}$), —N(R$^{13}$)(R$^{14}$), $C_2$–$C_6$ alkoxyalkyl, $C_1$–$C_4$ haloalkyl, $C_1$–$C_4$ alkoxycarbonyl, —C(=O)OH, $C_1$–$C_4$ alkylcarbonyloxy, $C_1$–$C_4$ alkylcarbonyl or —C(R$^{14}$)=N—O(R$^{14}$));

R$^{40}$ is: hydrogen or $C_1$–$C_3$ alkyl;

R$^{41}$ is: —C(=O)N(R$^{13}$)(R$^{14}$), —C(=O)N(R$^{13}$)NH(R$^{14}$), —C(=O)C(R$^{11}$)$_2$N(R$^{13}$)(R$^{14}$), —C(=O)C(R$^{11}$)$_2$N(R$^{13}$)NH(R$^{14}$), —C(=O)C(R$^{11}$)$_2$N(R$^{13}$)C(=O)O(R$^{13}$), —C(=O) H, —C(=O)(R$^{11}$), —C(=O)—($C_1$–$C_4$ alkyl)—N(R$^{13}$)(R$^{14}$), —C(=O)—($C_1$–$C_4$ alkyl)—N(R$^{13}$)C(=O)O(R$^{13}$) or 1–3 amino acids linked together via amide bonds and linked to the N atom via the carboxylate terminus; and n is: 0, 1 or 2;

provided that:

R$^4$, R$^{4A}$, R$^7$ and R$^{7A}$ are not all hydrogen;

when R$^4$ and R$^{4A}$ are both hydrogen, R$^{22}$ is not hydrogen, and when R$^7$ and R$^{7A}$ are both hydrogen, R$^{23}$ is not hydrogen.

70. The method according to claim 69, wherein the direct alkylation comprises treating a compound of Formula (IIa) with a base and an alkylating agent, where the alkylating agent has the Formula R$^{16}$X$^1$, wherein R$^{16}$ is:

$C_1$–$C_8$ alkyl substituted with 0–3 R$^{31}$, $C_2$–$C_8$ alkenyl substituted with 0–3 R$^{31}$, $C_2$–$C_8$ alkynyl substituted with 0–3 R$^{31}$, a $C_3$–$C_{14}$ carbocyclic ring system substituted with 0–5 R$^{31}$ or 0–5 R$^{32}$, or a 5- to 10-membered heterocyclic ring system containing 1 to 4 heteroatoms independently selected from oxygen, nitrogen or sulfur, the heterocyclic ring system being substituted with 0–2 R$^{32}$; and X$^1$ is a leaving group susceptible to displacement with an amino nitrogen.

71. The method according to claim 70, wherein the leaving group X$^1$ is halide, tosylate, mesylate or acetate.

72. The method according to claim 70, wherein the compound of Formula (IIa) and the alkylating agent of Formula R$^{16}$X$^1$ are contacted in a molar ratio of between about 1:0.9 and about 1:1.5.

73. The method according to claim 70, wherein the base is potassium carbonate, sodium carbonate, lithium carbonate, cesium carbonate, potassium bicarbonate or sodium bicarbonate.

74. The method according to claim 70, wherein the direct alkylation is conducted in the presence of a phase transfer agent.

75. The method according to claim 74, wherein the phase transfer agent is tetrabutylammonium iodide and potassium iodide.

76. The method according to claim 70, wherein the direct alkylation is conducted in a solvent selected from the group consisting of acetonitrile and tetrahydrofuran, and wherein the compound of Formula (IIa) is present in the solvent at a concentration of about 0.03 molar to about 3.0 molar, and wherein the base is potassium carbonate, and wherein about two equivalents of base are present for each equivalent of the compound of Formula (IIa).

77. The method according to claim 69, wherein the reductive amination comprises reacting a compound of Formula (IIa) with a carbonyl compound to form an intermediate oxime, and reacting the intermediate oxime with a reducing agent to form a compound of Formula (IIb), wherein the carbonyl compound is $C_1$–$C_8$ alkane substituted with 0–3 R$^{31}$, $C_2$–$C_8$ alkene substituted with 0–3 R$^{31}$, $C_2$–$C_8$ alkyne substituted with 0–3 $R^{31}$, a $C_3$–$C_{14}$ carbocyclic ring substituted with 0–5 $R^{31}$ or 0–5 $R^{32}$, and a 5- to 10-membered heterocyclic ring containing 1 to 4 heteroatoms independently selected from oxygen, nitrogen or sulfur, the heterocyclic ring being substituted with 0–2 $R^{32}$, with the proviso that at least one methylene group (—$CH_2$—) is replaced with a carbonyl group (—C(=O)—).

78. The method according to claim 77, wherein the reducing agent is $NaBH_4$, lithium aluminum hydride ($LiAlH_4$), sodium cyanoborohydride ($NaBH_3CN$), borane complexes including $BH_3$.THF, $BH_3$.$SMe_2$, $BH_3$.amine including pyridine, and other borane compounds including $BH(OAc)_3$, $BH(O_2CCF_3)_2$, $NaBH(OAc)_3$, (t-butyl)$NH_2BH_3$, $LiBH(Et)_3$, $LiBH(t-butyl)_3$, $NaAlH_2(O(CH_2)_2OCH_3)$, $LiBH(sec-butyl)_3$ or $Zn(BH_3CN)_2$.

79. The method according to claim 77, wherein the molar ratio of the carbonyl compound to the compound of Formula (IIa) is about 1:1.

80. The method according to claim 69, wherein the successive acylation and reduction comprises reacting a compound of Formula (IIa) with an acylating agent of Formula $R^{17}(C=O) X^2$ to form an amide compound, and the amide compound is reacted with a reducing agent to form a compound of Formula (IIb), wherein $R^{17}$ is:

$C_1$–$C_7$ alkyl substituted with 0–3 $R^{31}$, $C_2$–$C_7$ alkenyl substituted with 0–3 $R^{31}$, $C_2$–$C_7$ alkynyl substituted with 0–3 $R^{31}$, or —$R^{31}$; and $X^2$ is a leaving group.

81. The method according to claim 80 wherein the leaving group $X^2$ is halide, —$OR^{17}$ or —OC(=O) $R^{17}$.

82. The method according to claim 80 wherein the molar ratio of the acylating agent to the compound of Formula (IIa) is about 1:1.

83. The method according to claim 80, wherein the reducing agent is lithium aluminum hydride ($LiAlH_4$), $BH_3$.THF, $BH_3$.$SMe_2$, $B_2H_6$, $NaBH_4$ and $MeSO_3H$ in DMSO, $(Bu)_4NBH_4$ in methylene chloride, $NaBH_4$-$TiCl_4$ in dimethoxyethane, $NiCl_2$ in methanol, heterogeneous catalytic hydrogenation with Cu chromite, Ba/Cu chromite, Raney nickel, Raney cobalt, or rhenium on carbon.

* * * * *